United States Patent
Salahieh et al.

(10) Patent No.: US 7,748,389 B2
(45) Date of Patent: Jul. 6, 2010

(54) LEAFLET ENGAGEMENT ELEMENTS AND METHODS FOR USE THEREOF

(75) Inventors: Amr Salahieh, Saratoga, CA (US); Brian D. Brandt, Santa Clara, CA (US); Robert A. Gleshlider, San Francisco, CA (US); Dwight P. Morejohn, Davis, CA (US); Tom Saul, El Granada, CA (US)

(73) Assignee: Sadra Medical, Inc., Los Gatos, CA (US)

( * ) Notice: Subject to any disclaimer, the term of this patent is extended or adjusted under 35 U.S.C. 154(b) by 1211 days.

(21) Appl. No.: 10/972,287

(22) Filed: Oct. 21, 2004

(65) Prior Publication Data

US 2005/0137698 A1 Jun. 23, 2005

Related U.S. Application Data

(63) Continuation-in-part of application No. 10/746,240, filed on Dec. 23, 2003, now abandoned.

(51) Int. Cl.
*A61F 2/24* (2006.01)

(52) U.S. Cl. .................. 128/898; 623/1.26; 623/2.14

(58) Field of Classification Search ............. 623/1.28, 623/1.24, 1.26, 2.1, 2.12, 2.13, 2.14, 2.15, 623/2.16, 2.17, 2.18, 2.19, 2.38, 2.39, 2.4
See application file for complete search history.

(56) References Cited

U.S. PATENT DOCUMENTS

| | | | |
|---|---|---|---|
| 3,334,629 A | 8/1967 | Cohn | |
| 3,409,013 A | 11/1968 | Berry | |
| 3,540,431 A | 11/1970 | Mobin-Uddin | |
| 3,628,535 A | 12/1971 | Ostrowsky et al. | |
| 3,642,004 A | 2/1972 | Osthagen et al. | |
| 3,657,744 A | 4/1972 | Ersek | |
| 3,671,979 A | 6/1972 | Moulopoulos | |
| 3,795,246 A | 3/1974 | Sturgeon | |
| 3,839,741 A | 10/1974 | Haller | |
| 3,868,956 A | 3/1975 | Alfidi et al. | |
| 3,874,388 A | 4/1975 | King et al. | |
| 4,056,854 A | 11/1977 | Boretos et al. | |

(Continued)

FOREIGN PATENT DOCUMENTS

EP 0409929 B1 4/1997

(Continued)

OTHER PUBLICATIONS

Salahieh, et al., U.S. Appl. No. 11/531,980, "Externally expandable heart valve anchor and method," filed Sep. 14, 2006.

(Continued)

*Primary Examiner*—Corrine M McDermott
*Assistant Examiner*—Rebecca Straszheim
(74) *Attorney, Agent, or Firm*—Shay Glenn LLP

(57) ABSTRACT

The present invention relates to apparatus for methods for endovascularly replacing a patient's heart valve. The apparatus includes an expandable anchor with leaflet engagement elements on the proximal end of the anchor and a replacement valve. The leaflet engagement elements can be used to prevent distal migration and insure proper positioning of the apparatus.

8 Claims, 49 Drawing Sheets

U.S. PATENT DOCUMENTS

| | | |
|---|---|---|
| 4,106,129 A | 8/1978 | Carpentier et al. |
| 4,233,690 A | 11/1980 | Akins |
| 4,291,420 A | 9/1981 | Reul |
| 4,326,306 A | 4/1982 | Poler |
| 4,423,809 A | 1/1984 | Mazzocco |
| 4,425,908 A | 1/1984 | Simon |
| 4,501,030 A | 2/1985 | Lane |
| 4,580,568 A | 4/1986 | Gianturco |
| 4,602,911 A | 7/1986 | Ahmadi et al. |
| 4,610,688 A | 9/1986 | Silvestrini et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | DiPisa, Jr. |
| 4,665,906 A | 5/1987 | Jervis |
| 4,710,192 A | 12/1987 | Liotta et al. |
| 4,733,665 A | 3/1988 | Palmaz |
| 4,755,181 A | 7/1988 | Igoe |
| 4,796,629 A | 1/1989 | Grayzel |
| 4,819,751 A | 4/1989 | Shimada et al. |
| 4,834,755 A | 5/1989 | Silvestrini et al. |
| 4,856,516 A | 8/1989 | Hillstead |
| 4,865,600 A | 9/1989 | Carpentier et al. |
| 4,872,874 A | 10/1989 | Taheri |
| 4,909,252 A | 3/1990 | Goldberger |
| 4,917,102 A | 4/1990 | Miller et al. |
| 4,954,126 A | 9/1990 | Wallsten |
| 4,986,830 A | 1/1991 | Owens et al. |
| 4,994,077 A | 2/1991 | Dobben |
| 5,002,559 A | 3/1991 | Tower |
| 5,064,435 A | 11/1991 | Porter |
| 5,161,547 A | 11/1992 | Tower |
| 5,163,953 A | 11/1992 | Vince |
| 5,209,741 A | 5/1993 | Spaeth |
| 5,217,483 A | 6/1993 | Tower |
| 5,258,042 A | 11/1993 | Mehta |
| 5,332,402 A * | 7/1994 | Teitelbaum ................ 623/2.42 |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,425,762 A | 6/1995 | Muller |
| 5,431,676 A | 7/1995 | Dubrul et al. |
| 5,443,495 A | 8/1995 | Buscemi et al. |
| 5,443,499 A | 8/1995 | Schmitt |
| 5,476,506 A * | 12/1995 | Lunn ......................... 623/1.28 |
| 5,476,510 A | 12/1995 | Eberhardt et al. |
| 5,507,767 A | 4/1996 | Maeda et al. |
| 5,545,133 A | 8/1996 | Burns et al. |
| 5,545,211 A | 8/1996 | An et al. |
| 5,549,665 A | 8/1996 | Vesely et al. |
| 5,554,185 A | 9/1996 | Block et al. |
| 5,575,818 A | 11/1996 | Pinchuk |
| 5,645,559 A | 7/1997 | Hachtman et al. |
| 5,662,671 A | 9/1997 | Barbut et al. |
| 5,667,523 A | 9/1997 | Bynon et al. |
| 5,674,277 A | 10/1997 | Freitag |
| 5,695,498 A | 12/1997 | Tower |
| 5,713,953 A | 2/1998 | Vallana et al. |
| 5,720,391 A | 2/1998 | Dohm et al. |
| 5,735,842 A | 4/1998 | Krueger et al. |
| 5,769,812 A | 6/1998 | Stevens et al. |
| 5,800,456 A | 9/1998 | Maeda et al. |
| 5,817,126 A | 10/1998 | Imran |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,840,081 A | 11/1998 | Andersen et al. |
| 5,843,158 A | 12/1998 | Lenker et al. |
| 5,855,597 A | 1/1999 | Jayaraman |
| 5,855,601 A | 1/1999 | Bessler et al. |
| 5,860,966 A | 1/1999 | Tower |
| 5,861,028 A | 1/1999 | Angell |
| 5,868,783 A | 2/1999 | Tower |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,907,893 A | 6/1999 | Zadno-Azizi et al. |
| 5,910,154 A | 6/1999 | Tsugita et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,070 A | 10/1999 | Bley et al. |
| 5,984,957 A | 11/1999 | Laptewicz, Jr. et al. |
| 5,984,959 A | 11/1999 | Robertson et al. |
| 5,993,469 A | 11/1999 | McKenzie et al. |
| 5,997,557 A | 12/1999 | Barbut et al. |
| 6,010,522 A | 1/2000 | Barbut et al. |
| 6,022,370 A | 2/2000 | Tower |
| 6,027,520 A | 2/2000 | Tsugita et al. |
| 6,027,525 A | 2/2000 | Suh et al. |
| 6,042,598 A | 3/2000 | Tsugita et al. |
| 6,042,607 A | 3/2000 | Williamson, IV et al. |
| 6,051,014 A | 4/2000 | Jang |
| 6,123,723 A | 9/2000 | Konya et al. |
| 6,142,987 A | 11/2000 | Tsugita |
| 6,146,366 A | 11/2000 | Schachar |
| 6,162,245 A | 12/2000 | Jayaraman |
| 6,165,200 A | 12/2000 | Tsugita et al. |
| 6,168,579 B1 | 1/2001 | Tsugita |
| 6,168,614 B1 | 1/2001 | Andersen et al. |
| 6,171,327 B1 | 1/2001 | Daniel et al. |
| 6,179,859 B1 | 1/2001 | Bates |
| 6,197,053 B1 | 3/2001 | Cosgrove et al. |
| 6,200,336 B1 | 3/2001 | Pavcnik et al. |
| 6,221,006 B1 | 4/2001 | Dubrul et al. |
| 6,221,091 B1 | 4/2001 | Khosravi |
| 6,221,096 B1 | 4/2001 | Aiba et al. |
| 6,231,544 B1 | 5/2001 | Tsugita et al. |
| 6,231,551 B1 | 5/2001 | Barbut |
| 6,241,757 B1 | 6/2001 | An et al. |
| 6,245,102 B1 | 6/2001 | Jayaraman |
| 6,258,114 B1 | 7/2001 | Konya et al. |
| 6,258,115 B1 | 7/2001 | Dubrul |
| 6,258,120 B1 | 7/2001 | McKenzie et al. |
| 6,270,513 B1 | 8/2001 | Tsugita et al. |
| 6,277,555 B1 | 8/2001 | Duran et al. |
| 6,309,417 B1 | 10/2001 | Spence et al. |
| 6,319,281 B1 | 11/2001 | Patel |
| 6,327,772 B1 | 12/2001 | Zadno-Azizi et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,348,063 B1 | 2/2002 | Yassour et al. |
| 6,352,708 B1 | 3/2002 | Duran et al. |
| 6,361,545 B1 | 3/2002 | Macoviak et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 * | 10/2002 | Bailey et al. ................ 623/1.24 |

| Patent/Pub No. | Date | Name |
|---|---|---|
| 6,468,303 B1 | 10/2002 | Amplatz et al. |
| 6,475,239 B1 | 11/2002 | Campbell et al. |
| 6,482,228 B1 | 11/2002 | Norred |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,537,297 B2 | 3/2003 | Tsugita et al. |
| 6,540,768 B1 | 4/2003 | Diaz et al. |
| 6,562,058 B2 | 5/2003 | Seguin et al. |
| 6,592,546 B1 | 7/2003 | Barbut et al. |
| 6,592,614 B2 | 7/2003 | Lenker et al. |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,652,571 B1 | 11/2003 | White et al. |
| 6,652,578 B2 | 11/2003 | Bailey et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,842 B1 | 3/2004 | Gifford et al. |
| 6,712,843 B2 | 3/2004 | Elliott |
| 6,714,842 B1 | 3/2004 | Ito |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,767,345 B2 | 7/2004 | St. Germain et al. |
| 6,773,454 B2 | 8/2004 | Wholey et al. |
| 6,776,791 B1 | 8/2004 | Stallings et al. |
| 6,790,229 B2 | 9/2004 | Berreklouw |
| 6,790,237 B2 | 9/2004 | Stinson |
| 6,821,297 B2 | 11/2004 | Snyders |
| 6,863,668 B2 | 3/2005 | Gillespie et al. |
| 6,887,266 B2 | 5/2005 | Williams et al. |
| 6,890,340 B2 | 5/2005 | Duane |
| 6,893,459 B1 | 5/2005 | Macoviak |
| 6,905,743 B1 | 6/2005 | Chen et al. |
| 6,911,036 B2 | 6/2005 | Douk et al. |
| 6,936,067 B2 | 8/2005 | Buchanan |
| 6,953,332 B1 | 10/2005 | Kurk et al. |
| 6,964,673 B2 | 11/2005 | Tsugita et al. |
| 6,969,395 B2 | 11/2005 | Eskuri et al. |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,979,350 B2 | 12/2005 | Moll et al. |
| 6,984,242 B2 | 1/2006 | Campbell et al. |
| 7,011,681 B2 | 3/2006 | Veseley |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,166,097 B2 | 1/2007 | Barbut |
| 7,175,653 B2 | 2/2007 | Gaber |
| 7,175,654 B2 | 2/2007 | Bonsignore et al. |
| 7,189,258 B2 | 3/2007 | Johnson et al. |
| 7,191,018 B2 | 3/2007 | Gielen et al. |
| 7,235,093 B2 | 6/2007 | Gregorich |
| 7,258,696 B2 | 8/2007 | Rabkin et al. |
| 7,374,560 B2 | 5/2008 | Ressemann et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044634 A1 | 11/2001 | Don Michael et al. |
| 2001/0044656 A1 | 11/2001 | Williamson et al. |
| 2002/0002396 A1 | 1/2002 | Fulkerson |
| 2002/0010489 A1 | 1/2002 | Grayzel et al. |
| 2002/0029981 A1 | 3/2002 | Nigam |
| 2002/0032480 A1 | 3/2002 | Spence et al. |
| 2002/0032481 A1 | 3/2002 | Gabbay |
| 2002/0052651 A1 | 5/2002 | Myers et al. |
| 2002/0055769 A1 | 5/2002 | Wang |
| 2002/0058995 A1 | 5/2002 | Stevens |
| 2002/0077696 A1 | 6/2002 | Zadno-Azizi et al. |
| 2002/0082609 A1 | 6/2002 | Green |
| 2002/0095173 A1 | 7/2002 | Mazzocchi et al. |
| 2002/0095209 A1 | 7/2002 | Zadno-Azizi et al. |
| 2002/0111674 A1 | 8/2002 | Chouinard et al. |
| 2002/0120328 A1 | 8/2002 | Pathak et al. |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0188341 A1 | 12/2002 | Elliott |
| 2002/0188344 A1 | 12/2002 | Bolea et al. |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 * | 2/2003 | Philipp et al. ............... 623/1.11 |
| 2003/0040771 A1 | 2/2003 | Hyodoh et al. |
| 2003/0040772 A1 | 2/2003 | Hyodoh et al. |
| 2003/0050694 A1 | 3/2003 | Yang et al. |
| 2003/0055495 A1 | 3/2003 | Pease et al. |
| 2003/0060844 A1 | 3/2003 | Borillo et al. |
| 2003/0070944 A1 | 4/2003 | Nigam |
| 2003/0109924 A1 | 6/2003 | Cribier |
| 2003/0109930 A1 | 6/2003 | Bluni et al. |
| 2003/0125795 A1 | 7/2003 | Pavcnik et al. |
| 2003/0130729 A1 * | 7/2003 | Paniagua et al. ........... 623/2.11 |
| 2003/0144732 A1 | 7/2003 | Cosgrove et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0199913 A1 | 10/2003 | Dubrul et al. |
| 2003/0199971 A1 | 10/2003 | Tower et al. |
| 2003/0199972 A1 | 10/2003 | Zadno-Azizi et al. |
| 2003/0208224 A1 | 11/2003 | Broome |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216774 A1 | 11/2003 | Larson |
| 2003/0229390 A1 | 12/2003 | Ashton et al. |
| 2003/0233117 A1 | 12/2003 | Adams et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza et al. |
| 2004/0073198 A1 | 4/2004 | Gilson et al. |

| | | | |
|---|---|---|---|
| 2004/0082904 A1 | 4/2004 | Houde et al. | |
| 2004/0082967 A1 | 4/2004 | Broome et al. | |
| 2004/0088045 A1 | 5/2004 | Cox | |
| 2004/0093016 A1 | 5/2004 | Root et al. | |
| 2004/0098022 A1 | 5/2004 | Barone | |
| 2004/0098099 A1 | 5/2004 | McCullagh et al. | |
| 2004/0098112 A1 | 5/2004 | DiMatteo et al. | |
| 2004/0111096 A1 | 6/2004 | Tu et al. | |
| 2004/0116951 A1 | 6/2004 | Rosengart | |
| 2004/0117004 A1 | 6/2004 | Osborne et al. | |
| 2004/0122468 A1 | 6/2004 | Yodfat et al. | |
| 2004/0127979 A1 | 7/2004 | Wilson et al. | |
| 2004/0133274 A1 | 7/2004 | Webler et al. | |
| 2004/0138694 A1 | 7/2004 | Tran et al. | |
| 2004/0138742 A1 | 7/2004 | Myers et al. | |
| 2004/0138743 A1 | 7/2004 | Myers et al. | |
| 2004/0153094 A1 | 8/2004 | Dunfee et al. | |
| 2004/0158277 A1 | 8/2004 | Lowe et al. | |
| 2004/0167565 A1 | 8/2004 | Beulke et al. | |
| 2004/0186563 A1 | 9/2004 | Lobbi | |
| 2004/0204755 A1 | 10/2004 | Robin | |
| 2004/0215331 A1 | 10/2004 | Chew et al. | |
| 2004/0215339 A1 | 10/2004 | Drasler et al. | |
| 2004/0225321 A1 | 11/2004 | Krolik et al. | |
| 2004/0254636 A1 | 12/2004 | Flagle et al. | |
| 2005/0033402 A1 | 2/2005 | Cully et al. | |
| 2005/0043711 A1 | 2/2005 | Corcoran et al. | |
| 2005/0075662 A1 | 4/2005 | Pedersen et al. | |
| 2005/0085841 A1 | 4/2005 | Eversull et al. | |
| 2005/0085842 A1 | 4/2005 | Eversull et al. | |
| 2005/0085843 A1 | 4/2005 | Opolski et al. | |
| 2005/0085890 A1 | 4/2005 | Rasmussen et al. | |
| 2005/0090846 A1 | 4/2005 | Pedersen et al. | |
| 2005/0096692 A1 | 5/2005 | Linder et al. | |
| 2005/0096734 A1 | 5/2005 | Majercak et al. | |
| 2005/0096735 A1 | 5/2005 | Hojeibane et al. | |
| 2005/0096736 A1 | 5/2005 | Osse et al. | |
| 2005/0096738 A1 | 5/2005 | Cali et al. | |
| 2005/0100580 A1 | 5/2005 | Osborne et al. | |
| 2005/0107822 A1 | 5/2005 | WasDyke | |
| 2005/0113910 A1 | 5/2005 | Paniagua et al. | |
| 2005/0137695 A1 | 6/2005 | Salahieh et al. | |
| 2005/0165352 A1 | 7/2005 | Henry et al. | |
| 2005/0165477 A1 | 7/2005 | Anduiza et al. | |
| 2005/0197694 A1 | 9/2005 | Pai et al. | |
| 2005/0197695 A1 | 9/2005 | Stacchino et al. | |
| 2005/0203614 A1 | 9/2005 | Forster | |
| 2005/0203615 A1 | 9/2005 | Forster | |
| 2005/0203616 A1 | 9/2005 | Cribier | |
| 2005/0203617 A1 | 9/2005 | Forster et al. | |
| 2005/0209580 A1 | 9/2005 | Freyman | |
| 2005/0228472 A1 | 10/2005 | Case et al. | |
| 2005/0251250 A1 | 11/2005 | Verhoeven et al. | |
| 2005/0251251 A1 | 11/2005 | Cribier | |
| 2005/0261759 A1 | 11/2005 | Lambrecht et al. | |
| 2005/0267560 A1 | 12/2005 | Bates | |
| 2005/0283231 A1 | 12/2005 | Haug et al. | |
| 2005/0283962 A1 | 12/2005 | Boudjemline | |
| 2006/0004439 A1 | 1/2006 | Spenser et al. | |
| 2006/0004442 A1 | 1/2006 | Spenser et al. | |
| 2006/0015168 A1 | 1/2006 | Gunderson | |
| 2006/0155312 A1 | 7/2006 | Levine et al. | |
| 2006/0259134 A1 | 11/2006 | Schwammenthal et al. | |
| 2008/0269878 A1 | 10/2008 | Iobbi | |
| 2008/0288054 A1 | 11/2008 | Pulnev et al. | |
| 2009/0054969 A1 | 2/2009 | Salahieh et al. | |
| 2009/0076598 A1 | 3/2009 | Salahieh et al. | |

FOREIGN PATENT DOCUMENTS

| | | | |
|---|---|---|---|
| EP | 1000590 A1 | 5/2000 | |
| EP | 1057459 | 12/2000 | |
| EP | 1057460 | 12/2000 | |
| EP | 0937439 B1 | 9/2003 | |
| EP | 1340473 | 9/2003 | |
| EP | 1356793 | 10/2003 | |
| EP | 1042045 B1 | 5/2004 | |
| EP | 0819013 | 6/2004 | |
| EP | 1589902 | 8/2004 | |
| EP | 1605871 | 9/2004 | |
| EP | 1229864 B1 | 4/2005 | |
| EP | 1430853 A3 | 6/2005 | |
| EP | 1059894 B1 | 7/2005 | |
| EP | 1551274 A2 | 7/2005 | |
| EP | 1551336 A1 | 7/2005 | |
| EP | 1078610 B1 | 8/2005 | |
| EP | 1562515 A1 | 8/2005 | |
| EP | 1576937 A2 | 9/2005 | |
| EP | 1582178 A2 | 10/2005 | |
| EP | 1582179 A2 | 10/2005 | |
| EP | 1469797 | 11/2005 | |
| EP | 1600121 A1 | 11/2005 | |
| EP | 1156757 B1 | 12/2005 | |
| EP | 1616531 | 1/2006 | |
| WO | WO 93/15693 | 8/1993 | |
| WO | WO 95/04556 | 2/1995 | |
| WO | WO 95/29640 | 11/1995 | |
| WO | WO 96/14032 | 5/1996 | |
| WO | WO 96/24306 A1 | 8/1996 | |
| WO | WO 98/36790 | 8/1998 | |
| WO | WO 98/50103 A1 | 11/1998 | |
| WO | WO 98/57599 A2 | 12/1998 | |
| WO | WO 99/44542 A2 | 9/1999 | |
| WO | WO 00/09059 | 2/2000 | |
| WO | WO 00/44308 | 8/2000 | |
| WO | WO 00/44313 | 8/2000 | |
| WO | WO 00/49970 A1 | 8/2000 | |
| WO | WO 00/67661 | 11/2000 | |
| WO | WO 01/05331 | 1/2001 | |
| WO | WO 01/08596 A1 | 2/2001 | |
| WO | WO 01/10320 A1 | 2/2001 | |
| WO | WO 01/10343 A1 | 2/2001 | |
| WO | WO 01/35870 | 5/2001 | |
| WO | WO 01/64137 | 9/2001 | |
| WO | WO 02/36048 | 5/2002 | |
| WO | WO 02/41789 A2 | 5/2002 | |
| WO | WO 02/100297 | 12/2002 | |
| WO | WO 03/003943 | 1/2003 | |
| WO | WO 03/003949 | 1/2003 | |
| WO | WO 03/011195 | 2/2003 | |
| WO | WO 03/015851 | 11/2003 | |
| WO | WO 2004/019811 | 3/2004 | |
| WO | WO 2004/023980 | 3/2004 | |
| WO | WO 2004/041126 | 5/2004 | |
| WO | WO 2005/084595 A1 | 9/2005 | |
| WO | WO 2005/087140 A1 | 9/2005 | |

OTHER PUBLICATIONS

Salahieh, et al., U.S. Appl. No. 11/532,019, "Methods and apparatus for endovascularly replacing heart valve," filed Sep. 14, 2006.

Fawzi, et al., U.S. Appl. No. 11/155,309, entitled "Apparatus and methods for intravascular embolic protection," filed Jun. 16, 2005.

Salahieh, et al., U.S. Appl. No. 11/232,441, entitled "Methods and apparatus for endovascular heart valve replacement comprising tissue grasping elements," filed Sep. 20, 2005.

Salahieh, et al., U.S. Appl. No. 11/232,444, entitled "Methods and apparatus for endovascular heart valve replacement comprising tissue grasping elements," filed Sep. 20, 2005.

Salahieh, et al., U.S. Appl. No. 11/274,889, entitled "Medical implant deployment tool," filed Nov. 14, 2005.

Salahieh, et al., U.S. Appl. No. 11/314,183, entitled "Medical Device Delivery," filed Dec. 20, 2005.

Salahieh, et al., U.S. Appl. No. 11/314,969, entitled "Methods And Apparatus For Performing Valvuloplasty," filed Dec. 20, 2005.

Haug, et al; U.S. Appl. No. 11/716,123, entitled "Methods and apparatus for endovascularly replacing a heart valve," filed Mar. 9, 2007.
Salahieh, et al; U.S. Appl. No. 11/706,549, entitled "Systems and Methods for Delivering a Medical Implant," filed Feb. 14, 2007.
Salahieh, et al; U.S. Appl. No. 11/732,906 entitled "Assessing the location and performance of replacement heart valves," filed Apr. 4, 2007.
Salahieh, et al., U.S. Appl. No. 11/275,913, entitled "Two-Part Package for Medical Implant," filed Feb. 2, 2006.
Boudjemline, Y. et al., "Percutaneious implantation of a biological valve in the aorta to treat aortic valve insufficiency—a sheep study", Med Sci.Monit. (2002) vol. 8, No. 4, pp. BR113-BR116.
Boudjemline, Y. et al., "Percutaneous Pulmonary Valve Replacement in a Large Right Ventricular Outflow Tract". J. of Am. College of Cardio. (2004) 43:6, 1082-1087.
Boudjemline, Y. et al., "Steps Toward Percutaneous Aortic Valve Replacement." Circulation (2002) 775-778.
Cribier, A. et al., "Early Experience with Percutaneous Transcatheter Implantation of Heart Valve Prosthesis for the Treatment of End-Stage Inoperable Patients with Calcific Aortic Stenosis". J. or Am. Coll. of Cardio. (2004) 43:4, 698-703.
Hijazi, Z.M., "Transcatheter Valve Replacement: A New Era of Percutaneous Cardiac Intervention Begins". J. of Am. College of Cardio. (2004) 43:6, 1088-1089.
Huber, C.H. et al., "Do valved stents compromise coronary flow?" European Journal of Cardio-thoracic Surgery, (2004) 25:754-759.
Stuart, M., "In Heart Valves, A Brave, New Non-Surgical World". Start-Up (2004) 9-17.
Vahanian, A. et al., "Percutaneous Approaches to Valvular Disease". Circulation (2004) 109, 1572-1579.
Andersen, H.R. et al. "Transluminal implantation of artificial heart valves. Description of a new expandable aortic valve and initial results with implantation by catheter technique in closed chest pigs." Euro. Heart J. 1992; 13:704-708.
Atwood, A. et al. "Insertion of Heart Valves by Catheterization." Project Supervised by Prof. S. Muftu of Northeaster University 2001-2002: 36-40.
Bodnar, E. et al. Replacement Cardiac Valves R Chapter 13: Extinct cardiac valve prostheses. Pergamon Publishing Corporation. New York, 1991: 307-322.
Boudjemline, Y. et al. "Percutaneous implantation of a valve in the descending aorta in lambs." Euro. Heart J. 2002; 23: 1045-1049.
Boudjemline, Y. et al. "Percutaneous valve insertion: A new approach?" J. of Thoracic and Cardio. Surg. 2003; 125(3): 741-743.

Cribier, A., et al. "Percutaneous Transcatheter Implantation of an Aortic Valve Prosthesis for Calcific Aortic Stenosis: First Human Case Description." Circulation. 2002; 106: 3006-3008.
Cribier, A., et al. "Percutaneous Transcatheter Implantation of an Aortic Valve Prosthesis for Calcific Aortic Stenosis: First Human Case." Percutaneous Valve Technologies, Inc. 2002: 16 pages.
Ferrari, M. et al. "Percutaneous transvascular aortic valve replacement with self expanding stent-valve device." Poster from the presentation given at SMIT 2000, 12th International Conference. Sep. 5, 2000.
Knudsen, L. L. et al. "Catheter-implanted prosthetic heart valves." Int'l J. of Art. Organs. 1993; 16(5): 253-262.
Kort, S. et al. "Minimally invasive aortic valve replacement: Echocardiographic and clinical results." Am. Heart J. 2001; 142(3): 476-481.
Love, C. et al. The Autogenous Tissue Heart Valve: Current Stat.f Journal of Cardiac Surgery. 1991; 6(4): 499-507.
Lutter, G. et al. "Percutaneous aortic valve replacement: An experimental study. I. Studies on implantation." J. of Thoracic and Cardio. Surg. 2002; 123(4): 768-776.
Moulopoulos, S. D. et al. "Catheter-Mounted Aortic Valves." Annals of Thoracic Surg. 1971; 11(5): 423-430.
Paniagua, D. et al. "Percutaneous heart valve in the chronic in vitro testing model." Circulation. 2002; 106: e51-e52.
Paniagua, D. et al. Heart Watch (2004). Texas Heart Institute. Spring, 2004 Edition: 8 pages.
Pavcnik, D. et al. "Percutaneous bioprosthetic veno valve: A long-term study in sheep." J. of Vascular Surg. 2002; 35(3): 598-603.
Phillips, S. J. et al. "A Temporary Catheter-Tip Aortic Valve: Hemodynamic Effects on Experimental Acute Aortic Insufficiency." Annals of Thoracic Surg. 1976; 21(2): 134-136.
Sochman, J. et al. "Percutaneous Transcatheter Aortic Disc Valve Prosthesis Implantation: A Feasibility Study." Cardiovasc. Intervent. Radiol. 2000; 23: 384-388.
Van Herwerden, L. A. et al., "Percutaneous valve implantation: back to the future?" Euro. Heart J. 2002; 23(18): 1415-1416.
Zhou, J. Q. et al. "Self-expandable valved stent of large size: off-bypass implantation in pulmonary position." Eur. J. Cardiothorac. 2003; 24: 212-216.
Salahieh, et al., U.S. Appl. No. 12/132,304 entitled "Low profile heart valve and delivery system," filed Jun. 3, 2008.
Haug et al.; U.S. Appl. No. 12/492,512 entitled "Everting Heart Valve," filed Jun. 26, 2009.

* cited by examiner

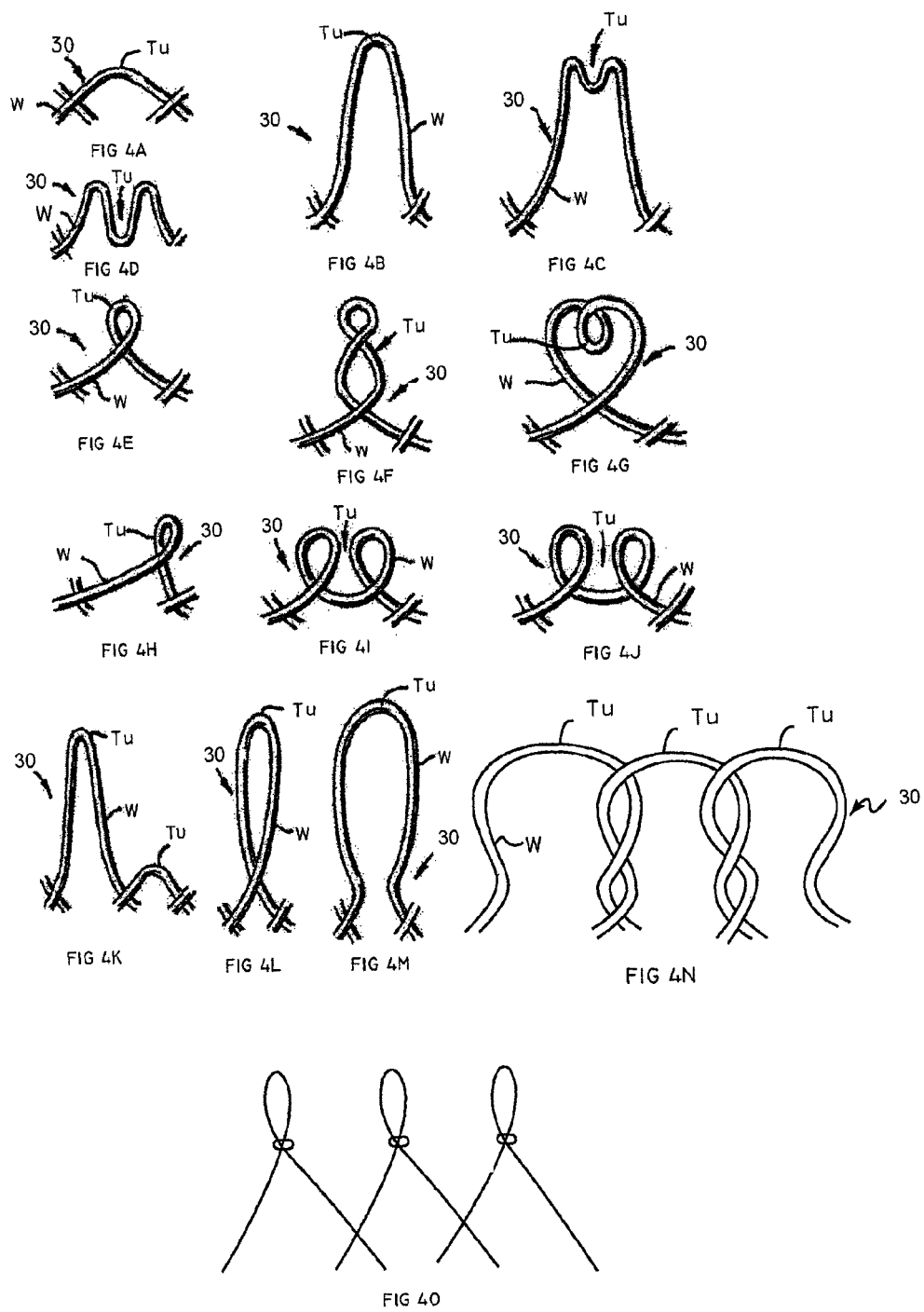

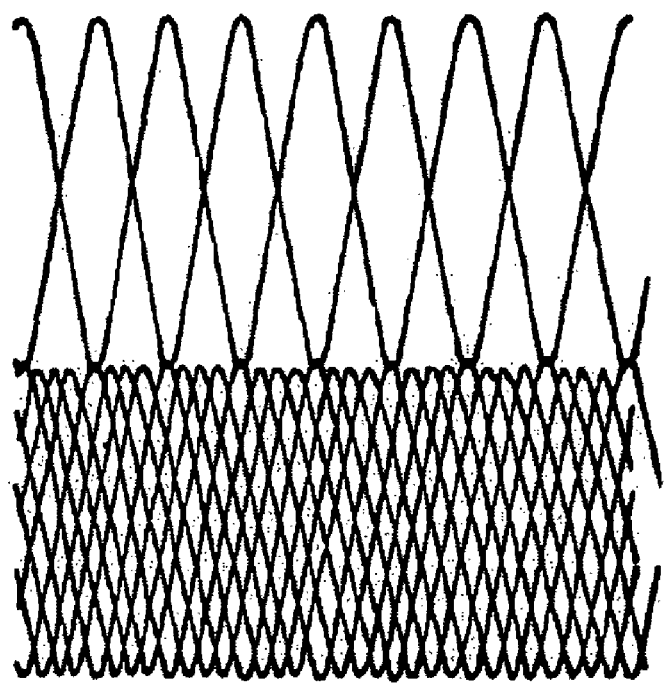
FIG IIA

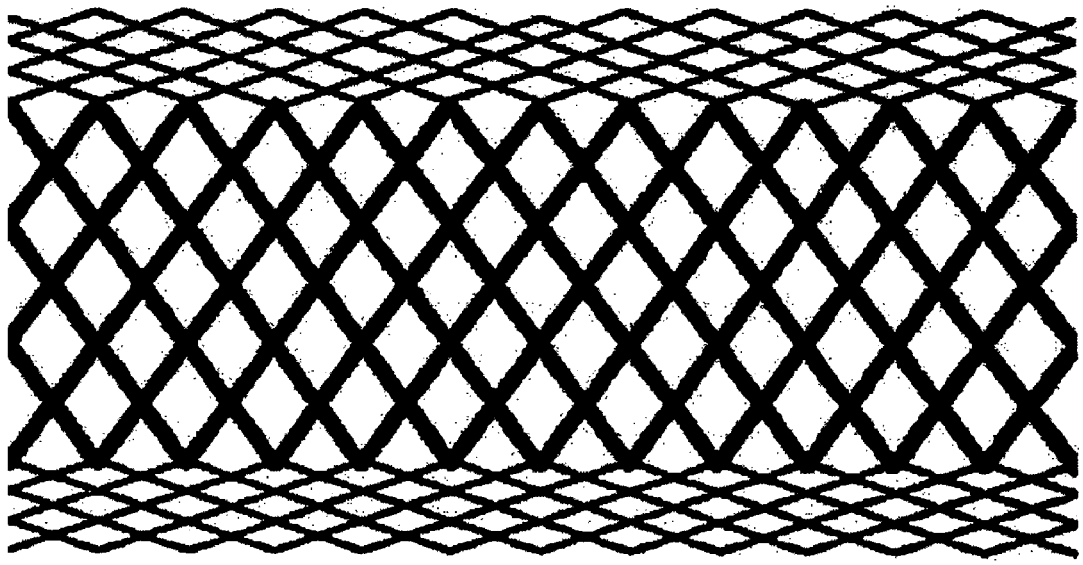
FIG IIB

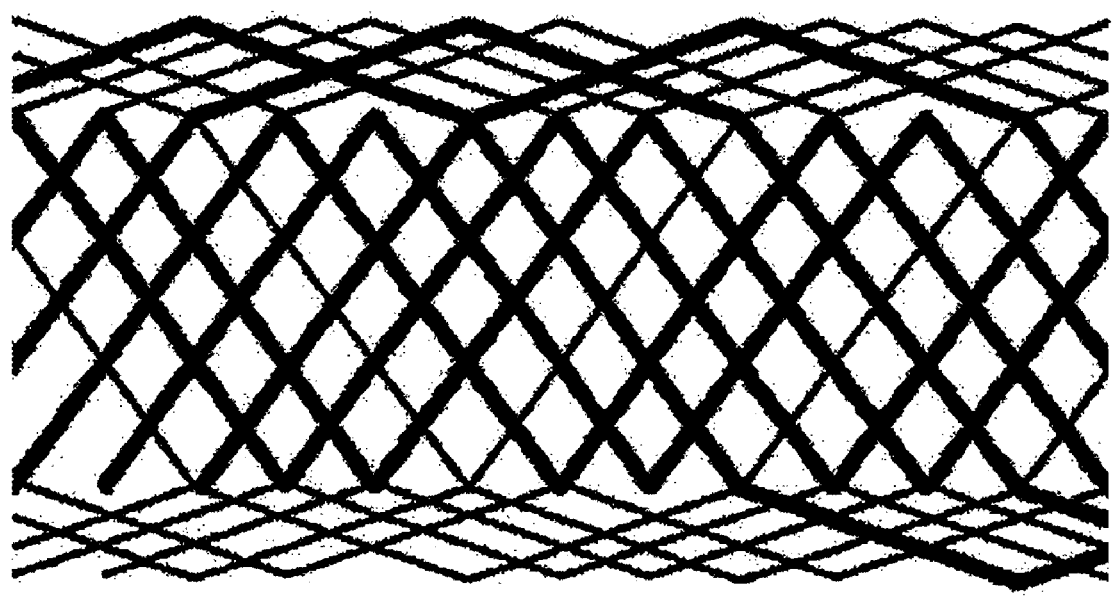
FIG IIC

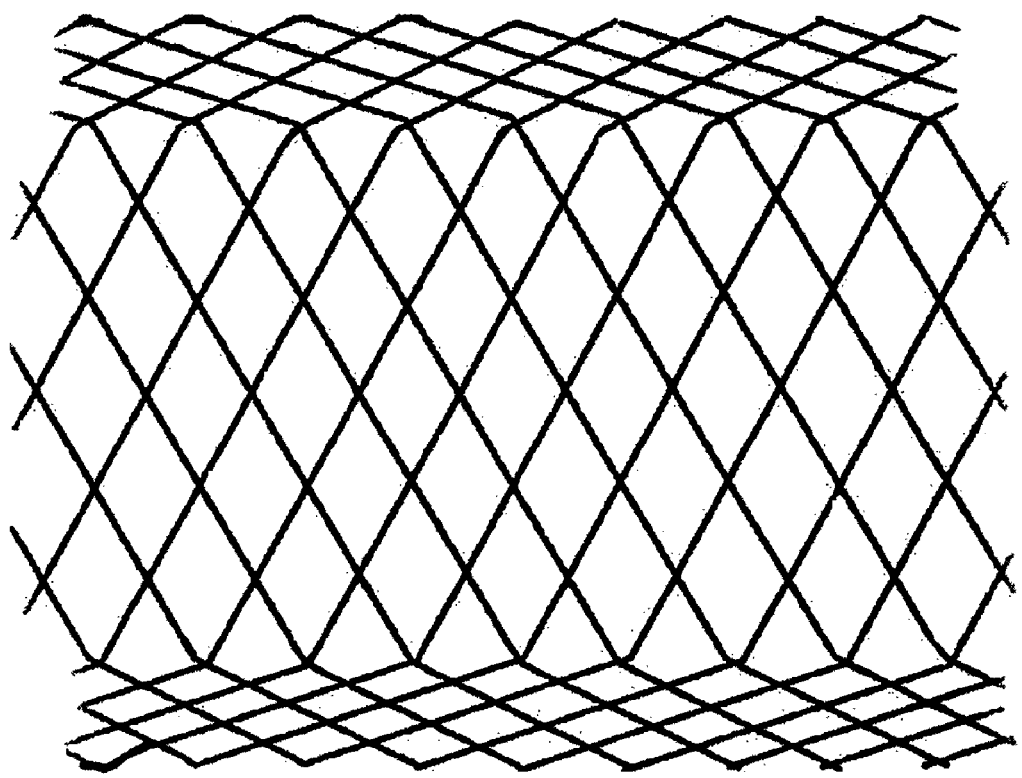
FIG IID

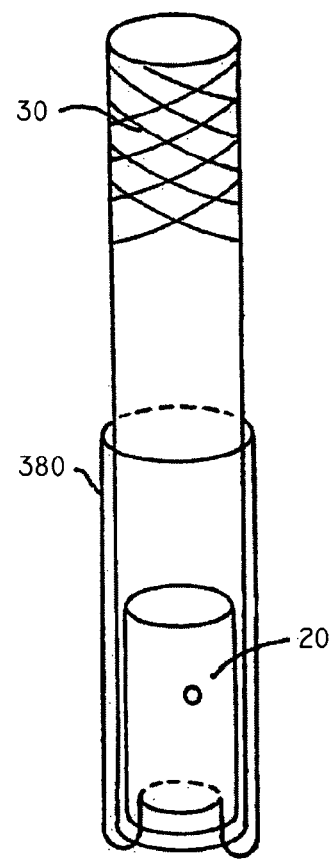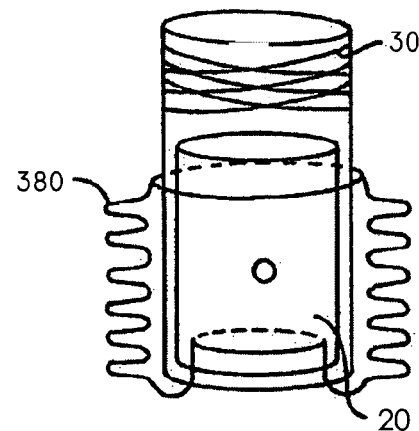
FIG 14A
FIG 14B
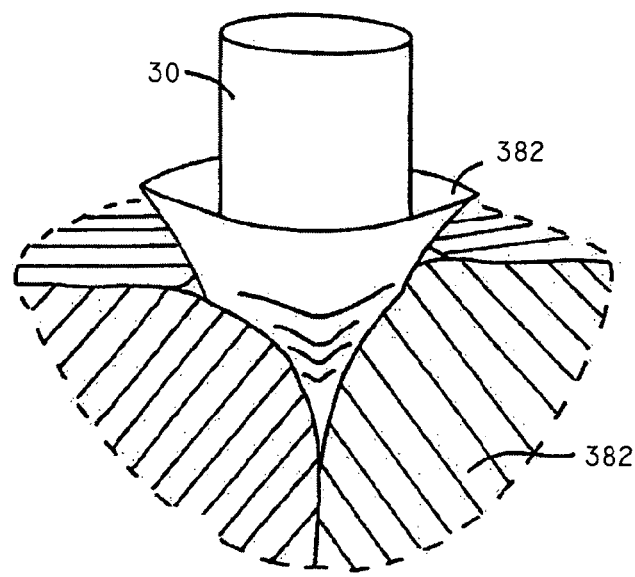
FIG 14C

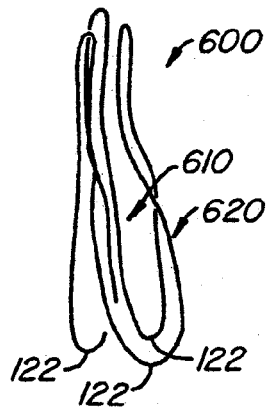
FIG. 20A
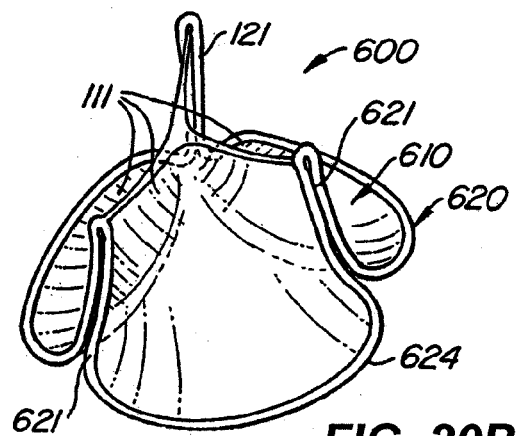
FIG. 20B
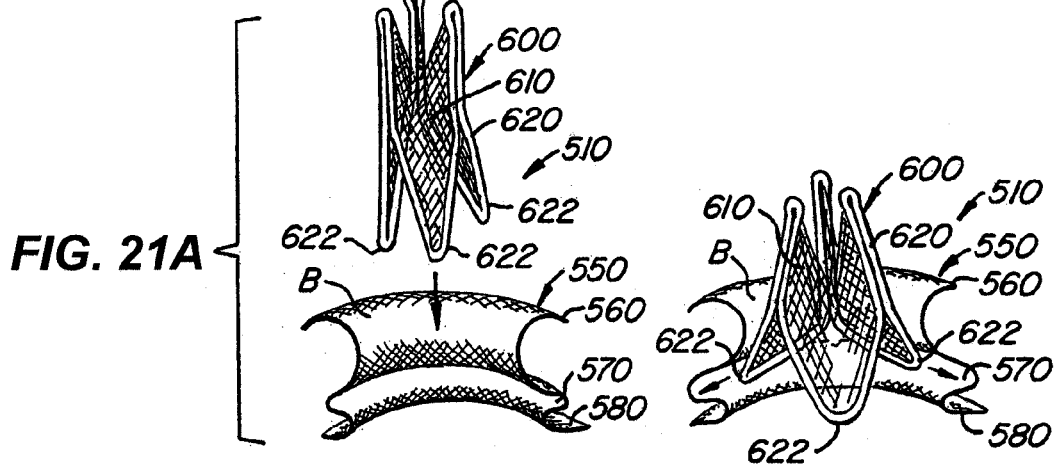
FIG. 21A
FIG. 21B
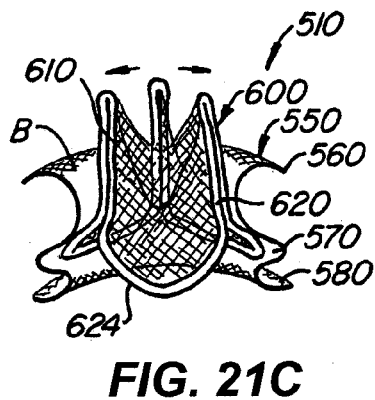
FIG. 21C
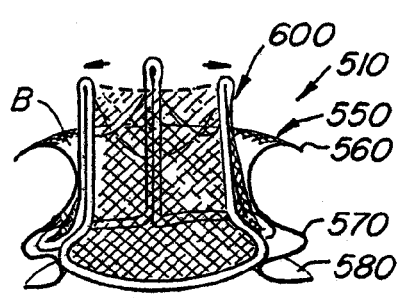
FIG. 21D

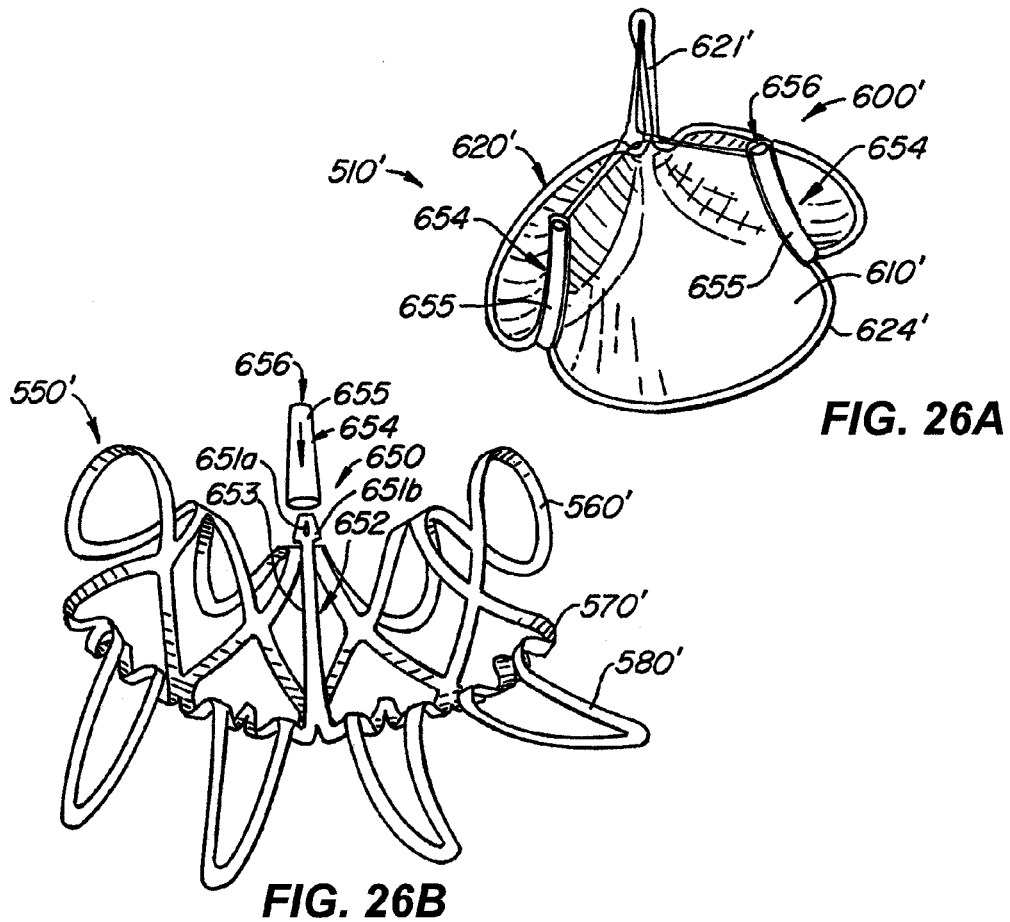
FIG. 26A
FIG. 26B
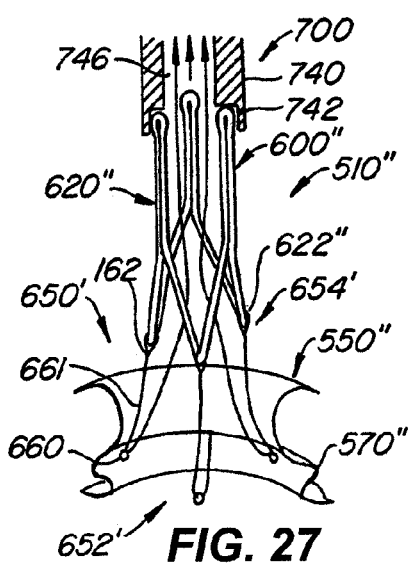
FIG. 27
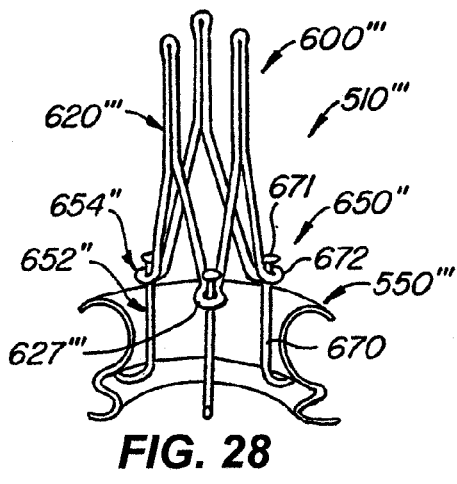
FIG. 28

LEAFLET ENGAGEMENT ELEMENTS AND METHODS FOR USE THEREOF

CROSS-REFERENCE

This application is a continuation-in-part application of application Ser. No. 10/746,240, filed Dec. 23, 2003 now abandoned, which is incorporated herein by reference in its entirety and to which application we claim priority under 35 USC §120.

BACKGROUND OF THE INVENTION

The present invention relates to methods and apparatus for endovascularly replacing a heart valve. More particularly, the present invention relates to methods and apparatus for endovascularly replacing a heart valve with a replacement valve using an expandable and retrievable anchor.

Heart valve surgery is used to repair or replace diseased heart valves. Valve surgery is an open-heart procedure conducted under general anesthesia. An incision is made through the patient's sternum (sternotomy), and the patient's heart is stopped while blood flow is rerouted through a heart-lung bypass machine.

Valve replacement may be indicated when there is a narrowing of the native heart valve, commonly referred to as stenosis, or when the native valve leaks or regurgitates. When replacing the valve, the native valve is excised and replaced with either a biologic or a mechanical valve. Mechanical valves require lifelong anticoagulant medication to prevent blood clot formation, and clicking of the valve often may be heard through the chest. Biologic tissue valves typically do not require such medication. Tissue valves may be obtained from cadavers or may be porcine or bovine, and are commonly attached to synthetic rings that are secured to the patient's heart.

Valve replacement surgery is a highly invasive operation with significant concomitant risk. Risks include bleeding, infection, stroke, heart attack, arrhythmia, renal failure, adverse reactions to the anesthesia medications, as well as sudden death. 2-5% of patients die during surgery.

Post-surgery, patients temporarily may be confused due to emboli and other factors associated with the heart-lung machine. The first 2-3 days following surgery are spent in an intensive care unit where heart functions can be closely monitored. The average hospital stay is between 1 to 2 weeks, with several more weeks to months required for complete recovery.

In recent years, advancements in minimally invasive surgery and interventional cardiology have encouraged some investigators to pursue percutaneous replacement of the aortic heart valve. However, the current devices suffer from several drawbacks.

First, many of the devices available today can become mispositioned with respect to the native valve. This is a critical drawback because improper positioning too far up towards the aorta risks blocking the coronary ostia of the patient. Furthermore, a misplaced stent/valve in the other direction (away from the aorta, closer to the ventricle) will impinge on the mitral apparatus and eventually wear through the leaflet as the leaflet continuously rubs against the edge of the stent/valve.

Moreover, some stent/valve devices simply crush the native valve leaflets against the heart wall and do not engage the leaflets in a manner that would provide positive registration of the device relative to the native position of the valve. This increases an immediate risk of blocking the coronary ostia, as well as a longer-term risk of migration of the device post-implantation.

Another drawback of the devices known today is that during implantation they may still require the patient to be on life support as the valve does not function for a portion of the procedure. This further complicates the implantation procedure.

Furtherstill, the stent comprises openings or gaps, thereby increasing a risk of improper seating of the valve within the stent and increasing the risk of paravalvular leaks. The interface between the stent and the native valve may additionally comprise gaps which again would increase the risks of paravalvular leaks.

In view of drawbacks associated with previously known techniques for endovascularly replacing a heart valve, it would be desirable to provide methods and apparatus that overcome those drawbacks.

SUMMARY OF THE INVENTION

One aspect of the invention provides an apparatus for endovascularly replacing a patient's heart valve. The apparatus includes: an expandable anchor and a replacement valve, wherein both are adapted for percutaneous delivery and deployment. The expandable anchor further includes a leaflet engagement element on its proximal end to engage the leaflets of the patient's heart valve. When the leaflets engagement element is engaged, the anchor is substantially distal to the coronary ostia of the patient. Moreover, once engaged, the leaflet engagement element prevents the distal movement of the anchor. In some embodiments, the leaflet engagement element is integral with the anchor or part of the anchor (especially when the anchor is an anchor braid). In other embodiments, the leaflet engagement element is attached to the proximal end of the anchor. In any of the embodiments herein, the anchor may be adapted for active foreshortening during deployment. Active foreshortening can occur by actuating the proximal and/or distal actuation elements of the anchor. The anchor herein may also be configured for locking and may include a locking element. The replacement valve of the apparatus herein is situated within the anchor and is adapted to permit blood flow and prevent blood backflow both during and after deployment.

Another aspect of the invention provides a method for endovascularly replacing a patient's heart valve. In some embodiments the method includes the steps of: endovascularly delivering an anchor comprising a leaflet engagement element on its proximal end and a replacement valve supported within the anchor to a vicinity of the heart valve in a collapsed delivery configuration; unsheathing the anchor allowing it to take a relaxed configuration intermediate between its sheathed and expanded configurations; expanding the anchor; and, engaging the leaflet engagement element with the native leaflets. The expanding step may further comprise actively foreshortening the anchor. Active foreshortening can include actuating proximal and/or distal actuation elements of the anchor. The method may also include the step of locking the anchor after it is in its deployed configuration. In some embodiments, when the anchor engages the patient's heart, the anchor is substantially distal to the coronary ostia.

In any of the embodiments herein, leaflet engagement element prevents the anchor from distally migrating at its proximal end.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A illustrates the apparatus in a collapsed delivery configuration within a delivery system. FIG. 1B illustrates the apparatus in an expanded configuration partially deployed from the delivery system.

FIGS. 4A-4O are schematic detail views illustrating end turns for a braided anchor.

FIGS. 11A-11D are schematic side views of various braided anchor configurations.

FIGS. 14A-14C illustrate an embodiment of a replacement heart valve and anchor in the undeployed and deployed configurations.

FIGS. 15A-H show yet another embodiment of a replacement heart valve, anchor and deployment system according to this invention.

FIGS. 20A-B show a replacement heart valve for use in a two-piece replacement heart valve and anchor embodiment of the invention.

FIGS. 21A-D show a method of coupling the anchor of FIG. 19 and the replacement heart valve of FIG. 20.

FIGS. 26A-B show another embodiment of a two-piece replacement heart valve and anchor according to this invention.

FIG. 27 shows yet another embodiment of a two-piece replacement heart valve and anchor according to this invention.

FIG. 28 shows yet another embodiment of a two-piece replacement heart valve and anchor according to this invention.

DETAILED DESCRIPTION OF THE INVENTION

The present invention relates to an apparatus and methods for endovascularly delivering and deploying an aortic prosthesis within a patient's native heart valve, referred to here out as "replacing" a patient's heart valve. The delivery system includes a sheath assembly, a multi-lumen shaft, and a guide wire for placing the apparatus endovascularly within a patient and a user control allowing manipulation of the aortic prosthesis. The apparatus includes an anchor and a replacement valve. The anchor and the replacement valve are adapted for percutaneous delivery and deployment within a patient's heart valve. In preferred embodiments, the anchor includes a leaflet engagement element and/or a seal inverting element situated on its proximal end. The leaflet engagement element is adapted for engaging the native leaflets of the patient's heart, or more preferably the proximal edge and/or the commissural attachments of the native leaflets. The leaflet engagement element need not extend all the way into the pocket or the distal end of the native leaflet. Preferred embodiments of the apparatus herein are depicted in FIGS. 1-14, which are discussed in more detail below.

Figure 1A:
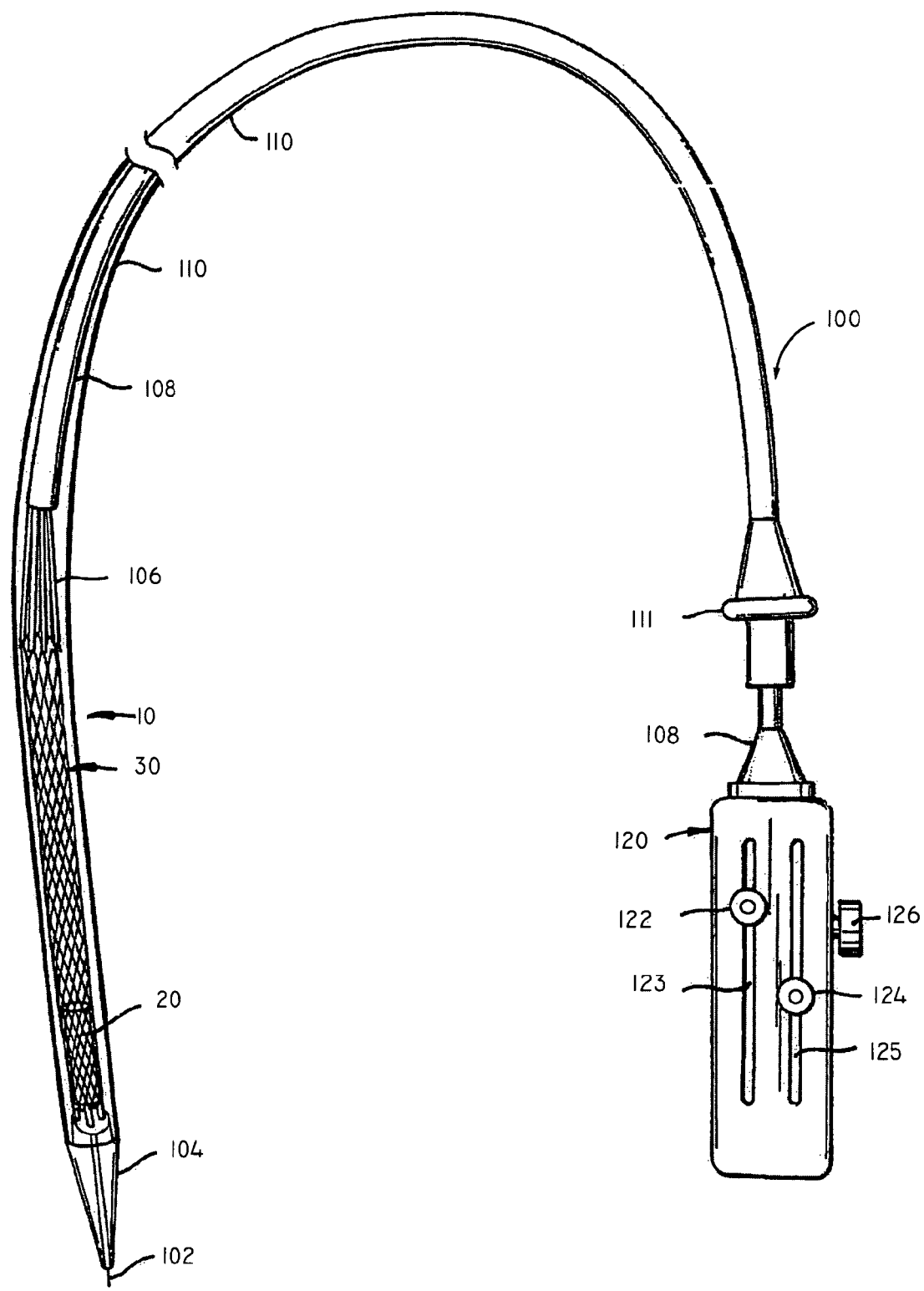
FIGS. 1A and 1B are schematic views of an anchor and valve apparatus in accordance with the present invention.
Figures 1B, 2:
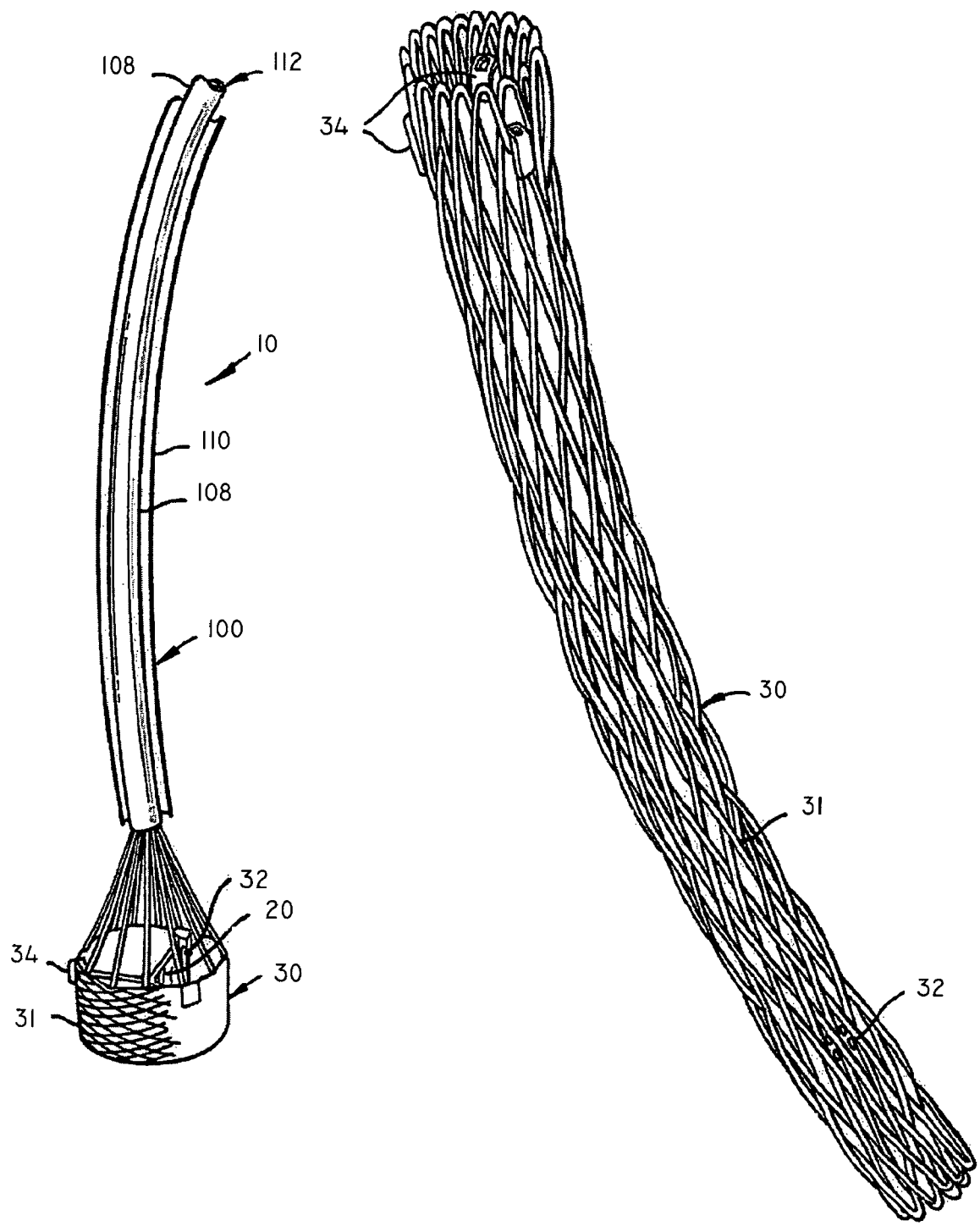
FIG. 2 illustrates an anchor of FIG. 1 in the collapsed delivery configuration with locking elements separated.

FIGS. 1A and 1B illustrate one embodiment of a delivery system and the apparatus of the present invention.

As illustrated by FIG. 1A, apparatus 10 may be collapsed for delivery within a delivery system 100. Delivery system 100 includes a guidewire 102, a nosecone 104, anchor actuation elements 106 (in this case fingers) coupled to a multi-lumen shaft 108, an external sheath 110 having a proximal handle 111, and a control handle 120. Delivery system 100 further comprises distal region control elements (not shown), comprised of or actuated by control wires 112, which pass through one or more lumens of shaft 108 and are reversibly coupled to posts 32 of anchor 30 for manipulating a distal region of apparatus 10. Thus, the distal region control elements may function as a distal actuation element.

The delivery system also comprises proximal region control elements comprised of or actuated by control wires 112 that pass through one or more lumens of shaft 108 and anchor actuation elements 106 to reversibly couple the control tubes to a proximal region of anchor 30. The control wires may comprise, for example, strands of suture, or metal or polymer wires. Control handle 120 is coupled to multi-lumen shaft 108. In some embodiments, these fingers and wires may be referred to as proximal actuation elements. A knob 122 disposed in slot 123 is coupled to the distal region control wires for controlling movement of the distal region of apparatus 10. Likewise, a knob 124 disposed in slot 125 is coupled to proximal region control wires 112 for control of the proximal region of apparatus 10. Handle 120 may also have a knob 126 for, e.g., decoupling the proximal and/or distal region control wires from apparatus 10, or for performing other control functions.

As illustrated by FIG. 1B, apparatus 10 comprises an anchor 30 and a replacement valve 20. Anchor 30 preferably comprises a braid. Such braid can have closed ends at either or both of its ends but preferably at least in its proximal end. Replacement valve 20 is preferably coupled to the anchor at posts 32 attached at distal region of the anchor. Post 32 therefore, may function as valve support and may be adapted to support the replacement valve within the anchor. In the embodiment shown, there are three posts, corresponding to the valve's three commissure attachments. The posts can be attached to braid portion of anchor 30. The posts can be attached to the braid's distal end, as shown in FIG. 2, central region, or proximal end. Replacement valve 20 can be composed of a metal, a synthetic material and/or may be derived from animal tissue. Replacement valve 20 is preferably configured to be secured within anchor 30.

In preferred embodiments, anchor 30 is collapsible and/or expandable and is formed from material such as Nitinol™, cobalt-chromium steel or stainless steel wire. More preferably, an anchor 30 is self-collapsing and/or self-expanding and is made out of shape memory material, such as Nitinol™. An anchor composed of shape memory material may self-expand to or toward its "at-rest" configuration. This "at rest" configuration of an anchor can be, for example its expanded configuration, its collapsed configuration, or a partially expanded configuration (between the collapsed configuration and the expanded configuration). In preferred embodiments, an anchor's at-rest configuration is between its collapsed configuration and its expanded configuration. Depending on the "at rest" diameter of the anchor and the diameter of the patient's anatomy at the chosen deployment location, the anchor may or may not self-expand to come into contact with the diameter of the patient's anatomy at that location.

Anchor 30 may be expanded to a fully deployed configuration from a partial deployed configuration (e.g., self-expanded configuration) by actively foreshortening anchor 30 during endovascular deployment. Active foreshortening is described in more detail in U.S. patent application Ser. No. 10/746,280, which is incorporated herein by reference in its entirety. During active foreshortening, the distal region of anchor 30 may be pulled proximally via a proximally directed force applied to posts 32 via a distal deployment system interface comprised of the distal system control elements. The distal deployment system interface is adapted to expand radially during application of a proximally directed force on the distal end of the anchor when opposed by a distally directed force applied to the proximal end of the anchor.

In some embodiments, actuating foreshortening of the apparatus involves applying a proximally directed force on a deployment system interface at the distal end of the anchor, while maintaining the proximal end of the anchor in the same location. In other embodiments, foreshortening of the apparatus involves applying a distally directed force on proximal end of the anchor (e.g., by applying a distally directed force on the anchor actuation elements).

Anchor actuation elements 106 (e.g., fingers, tubes, posts, and control wires connecting to posts) are preferably adapted to expand radially as the anchor expands radially and to contract radially as the anchor contracts radially. Furthermore, proximally or distally directed forces by the anchor actuation elements on one end of the anchor do not diametrically constrain the opposite end of the anchor. In addition, when a proximally or distally directed force is applied on the anchor by the anchor actuation elements, it is preferably applied without passing any portion of a deployment system through a center opening of the replacement valve. This arrangement enables the replacement valve to operate during deployment and before removal of the deployment system.

The distal deployment system interface may include control wires that are controlled, e.g., by control knob 122 of control handle 120. Similarly, the proximal regions of anchor 30 may be pushed distally via a proximal deployment system interface at the proximal end of the anchor. The proximal deployment system interface is adapted to permit deployment system to apply a distally directed force to the proximal end of anchor 30 through, e.g., fingers, which are controlled by, e.g., control knob 124 of control handle 120. The proximal deployment system interface may be further adapted to expand radially during application of a distally directed force on the proximal end of the anchor. Preferably, the proximal deployment system interface is adapted to permit deployment system to apply a distally directed force on the proximal end of the anchor system through a plurality of deployment system fingers or tubes 160. Such expansion optionally may be assisted via inflation of a balloon catheter (not shown) reversibly disposed within apparatus 10, as described in U.S. patent application Ser. No. 10/746,280.

Once anchor 30 is fully deployed, posts 32 and buckles 34 of anchor 30 may be used to lock and maintain the anchor in the deployed configuration. In one embodiment, the control wires attached to posts 32 are threaded through buckles 34 so that the proximally directed force exerted on posts 32 by the control wires during deployment pulls the proximal locking end of posts 32 toward and through buckles 34. Such lock optionally may be selectively reversible to allow for repositioning and/or retrieval of apparatus 10 during or post-deployment. Apparatus 10 may be repositioned or retrieved from the patient until the two-part locking mechanism of posts 32 and buckles 34 of anchor 30 have been actuated. When the lock is selectively reversible, the apparatus may be repositioned and/or retrieved as desired, e.g., even after actuation of the two-part locking mechanism. Once again, further details of this and other anchor locking structures may be found in U.S. patent application Ser. No. 10/746,280. Locking mechanisms used herein may also include a plurality of levels of locking wherein each level of locking results in a different amount of expansion. For example, the proximal end of the post can have multiple configurations for locking within the buckle wherein each configuration results in a different amount of anchor expansion. FIG. 2 illustrates a braided anchor of FIG. 1 in the collapsed delivery configuration with locking elements separated.

Figure 3:
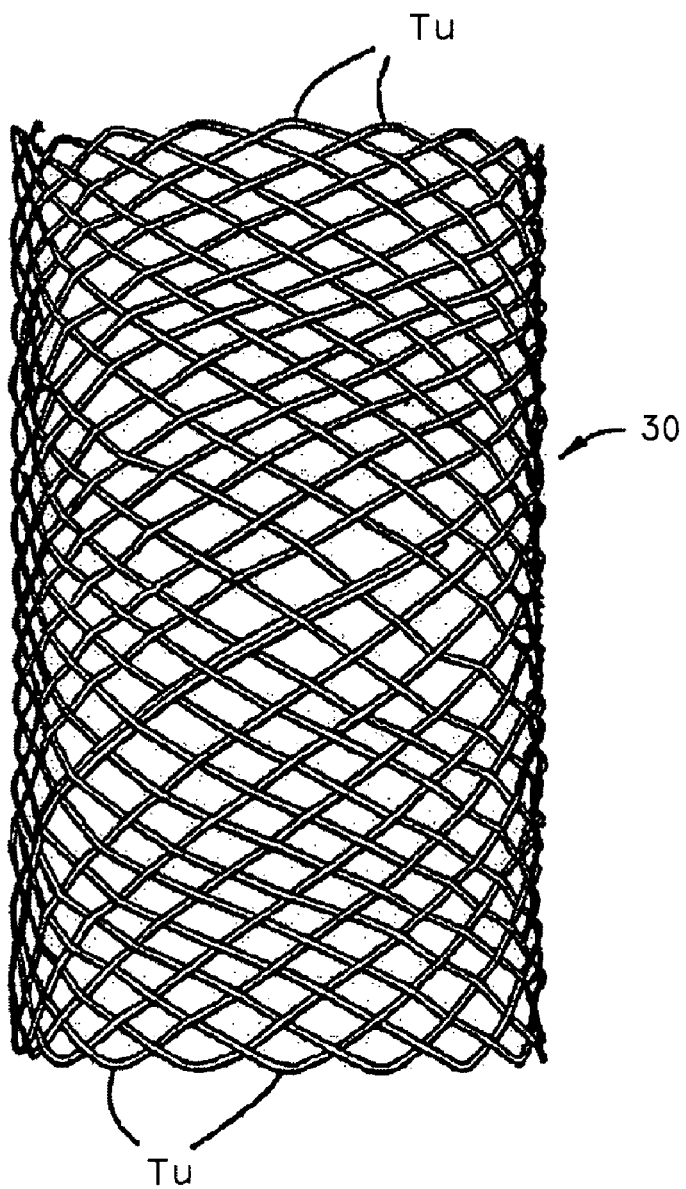
FIG. 3 illustrates a braided anchor of the present invention with closed end turns Tu.

FIG. 3 provides a detail view of a front side region of anchor braid 30 with closed end turns Tu. Anchor braid 30 includes various cells, some having an end turn (Tu). End turns can serve various functions. For example, end turns can be configured to reduce the sheathing force, to reduce stress within the braid during delivery and deployment, to prevent distal migration during expansion of the anchor, and/or to positively register the anchor against the native valve during deployment. In preferred embodiments, an end turn feature functions to prevent distal migration and to register the anchor by engaging the native leaflets. In preferred embodiments, the proximal end of an anchor comprises embodiments (Tu).

FIGS. 4A-4N provide multiple examples of edge cells having end turn feature. The end turn features disclosed and others known in the art may be used as leaflet engagement elements to engage the native heart leaflets with the anchor. The leaflet engagement elements are preferably integral with the anchor, or more preferably part of a braided anchor. The end turn features can occur at the proximal end, the distal end, or both proximal and distal ends of the anchor.

For example, FIG. 4A illustrates a detail view of a standard end turn Tu in an anchor braid resulting in a braid with substantially uniform cell size and shape.

FIG. 4B illustrates a turn that has been elongated to lengthen the distance over which forces concentrated in the turn may be distributed, resulting in an anchor braid having edge cells that are longer along the anchor axis than the other cells defined by the braid. This elongated turn feature may be formed by routing the wire of braid about outer posts and then heat setting the wire.

FIG. 4C illustrates an alternative anchor edge cell configuration, wherein the tip of the elongated wire turn may be bent out of a cylindrical shape defined by the braid of anchor braid 30. This may be achieved, for example, via a combination of routing of wire W within a fixture and then heat setting. Such a turn Tu in the anchor edge cells in FIG. 4C may reduce stress in some configurations without increasing height, and may also provide a lip for engaging the patient's native valve leaflets to facilitate proper positioning of apparatus 10 during deployment.

In FIG. 4D, a W-shaped turn feature has been formed at the wire turn, e.g., by routing the wire of anchor braid 30 about a central inner post and two flanking outer posts. As with the elongated braid cells of FIGS. 4B and 4C, the W-shape may better distribute stress about turn Tu.

The anchor edge cell configuration in FIG. 4E includes a loop formed in braid 30 at the turn, which may be formed by looping wire W around an inner or outer post.

FIG. 4F provides another alternative anchor edge cell configuration having a figure-eight shape. Such a shape may be formed, for example, by wrapping wire W about an inner post and an aligned outer post in a figure-eight fashion, and then heat setting the wire in the resultant shape.

In FIG. 4G, the edge cells of braid 30 include a heart-shaped configuration, which may be formed by wrapping the wire about an aligned inner and outer post in the desired manner.

In FIG. 4H, the edge cells of braid 30 have an asymmetric loop at turn Tu. The asymmetric loop will affect twisting of braid 30 during expansion and collapse of the braid, in addition to affecting stress concentration.

In FIG. 4I, the anchor edge cells have a double-looped turn configuration, e.g. via wrapping about two adjacent inner or outer posts. Additional loops may also be employed.

The double loop turn feature may be formed with a smooth transition between the loops, as in FIG. 4I, or may be heat set with a more discontinuous shape, as in FIG. 4J.

FIG. 4K illustrates that the edge cells of braid 30 may have multiple different configurations about the anchor's circumference. For example, the anchor edge cells shown in FIG. 4K have extended length cells as in FIG. 4B disposed adjacent to standard size edge cells, as in FIG. 4A.

The anchor edge cells of FIG. 4L have an extended turn configuration having an extended loop.

The anchor edge cells shown in FIG. 4M have an alternative extended configuration with a specified heat set profile.

In FIG. 4N, some or all anchor edge cells are interwoven. When interwoven, one or more edge cells may be shorter or longer than an adjacent edge cell. This permits one or more edge cells to extend into one or more leaflet pocket(s). For example, in FIG. 4N the middle Tu may be taller than the two adjacent edge cells thus permitting the edge cell to be situated within a leaflet pocket.

In any of the embodiments herein, edge cells may be wrapped using wire, string, or sutures, at a location where the wire overlaps after an end turn as is illustrated in FIG. 4O. This tied-end turn feature prevents cells from interlocking with each other during deployment.

The anchor and any of its features may be heat set at different configurations. For example, the anchor may be heat set ay its "at rest" configuration such that upon unsheathing it expands radially. The end turn features/leaflet engagement elements may be heat set at a different "at rest" configuration than the rest of the anchor. In preferred embodiment, end turn features are heat set to "flower" and then "evert" upon unsheathing.

The end turn features of FIG. 4 are provided only for the sake of illustration and should in no way be construed as limiting. Additional turn features within the scope of the present invention will apparent to those of skill in the art in view of FIG. 4. Furthermore, combinations of any such end turn features may be provided to achieve the desired characteristics of anchor 30.

Figure 5A:
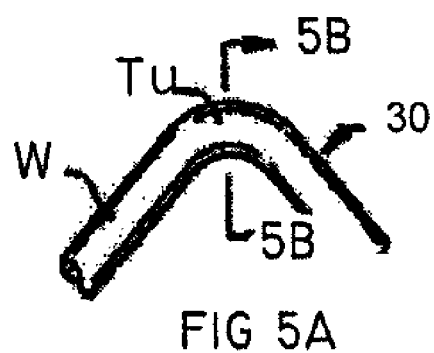
FIGS. 5A-5E illustrate additional features for end turns of a braided anchor.
Figure 5B:
Figure 5C:
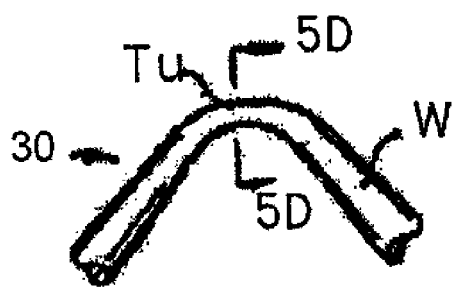

Referring now to FIGS. 5A-E, additional configurations for reducing stress concentration and/or circumferential stiffness of an anchor braid and/or leaflet engagement elements are illustrated. Such configurations can be used independently or in conjunction with other configurations disclosed herein. Such configurations are preferably used at the anchor's edges to locally reduce the cross-sectional area of substantially all cells or all cells in the anchor braid's edge (e.g., proximal and/or distal). As seen in FIGS. 5A and 5B, turns Tu in wire W typically may have a substantially continuous (e.g., round) cross-sectional profile. As seen in FIG. 5C, modifying the edge cell configuration by locally reducing the thickness or cross-sectional area of wire W at turn(s) Tu will reduce stress concentration within the wire at the turns and facilitate collapse and/or expansion of anchor braid 30 from the delivery to the deployed configurations. Furthermore, it is expected that such localized reduction in thickness or cross-sectional area will reduce a risk of kinking, fatigue or other failure at turns Tu.

Figure 5D:
Figure 5E:

In any of the embodiments herein, localized reduction of an anchor wire may be achieved via a localized etching and/or electropolishing process. Alternatively or additionally, localized grinding of the turns may be utilized. Additional processing techniques will be apparent to those of skill in the art. As seen in FIGS. 5D-5E, wire W may, for example, comprise an oval or rectangular cross-sectional profile, respectively, after localized reduction. The wire alternatively may comprise a round profile of reduced cross-sectional area (not shown). Additional profiles will be apparent. Localized reduction can take place at any time (e.g., before or after a braid is woven). Preferably, localized reduction occurs after weaving. However, in some embodiments, a wire of a given length may be etched or ground at preset segments and subsequently woven.

With reference now to FIGS. 6A-F, a method of endovascularly replacing a patient's diseased aortic valve is provided. The method involves endovascularly delivering an anchor/valve apparatus and properly positioning such apparatus via positive registration with the patient's native valve leaflets. Registration with the native valve leaflet preferably occurs using the leaflet engagement elements.

Figure 6A:
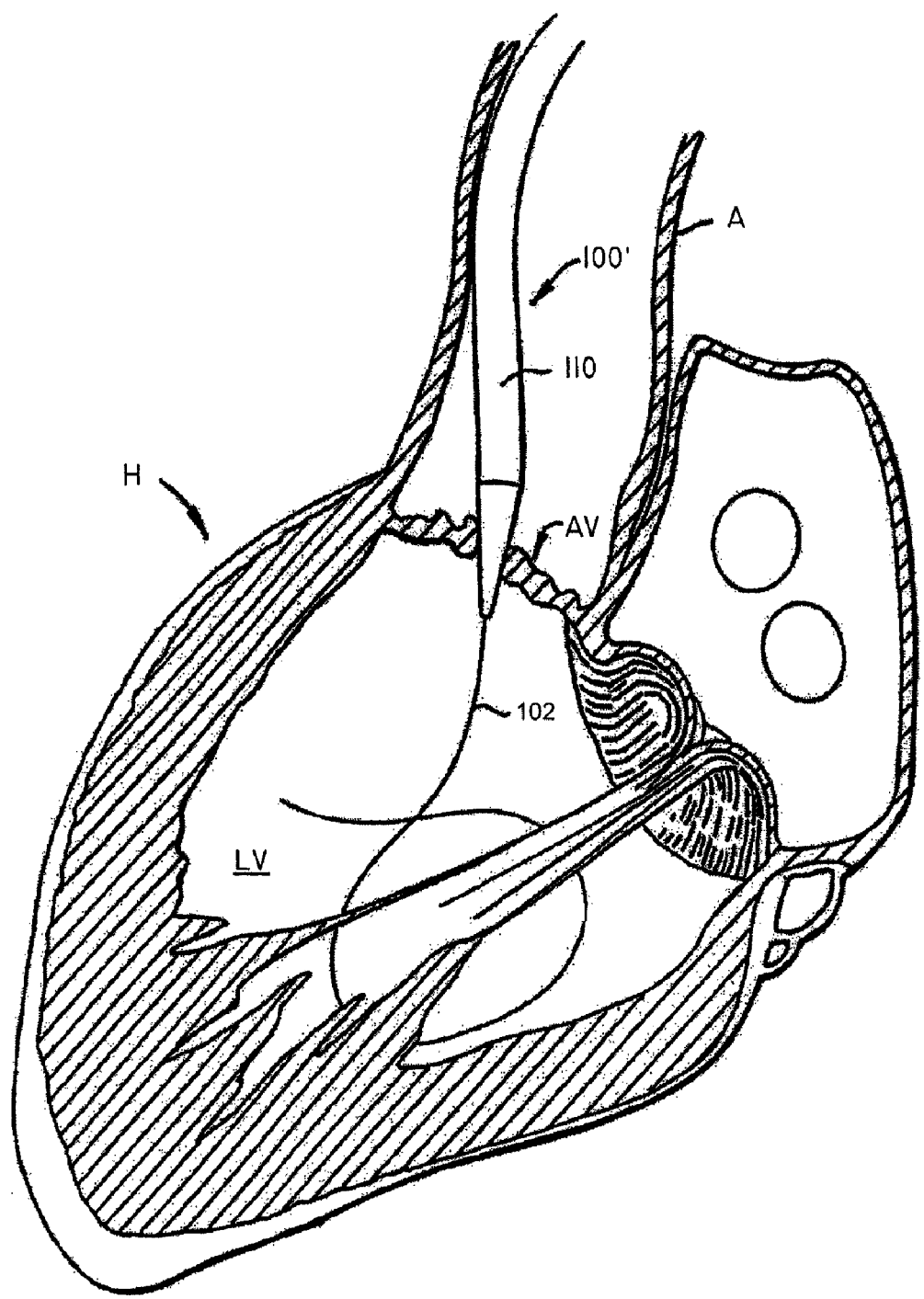
FIGS. 6A-6F illustrate deployment of an anchor with leaflet engagement elements on the deployment system.

In FIG. 6A, modified delivery system 100' delivers apparatus 10 to diseased aortic valve AV within sheath 110. Apparatus 10 is delivered in a collapsed delivery configuration.

Figure 6B:
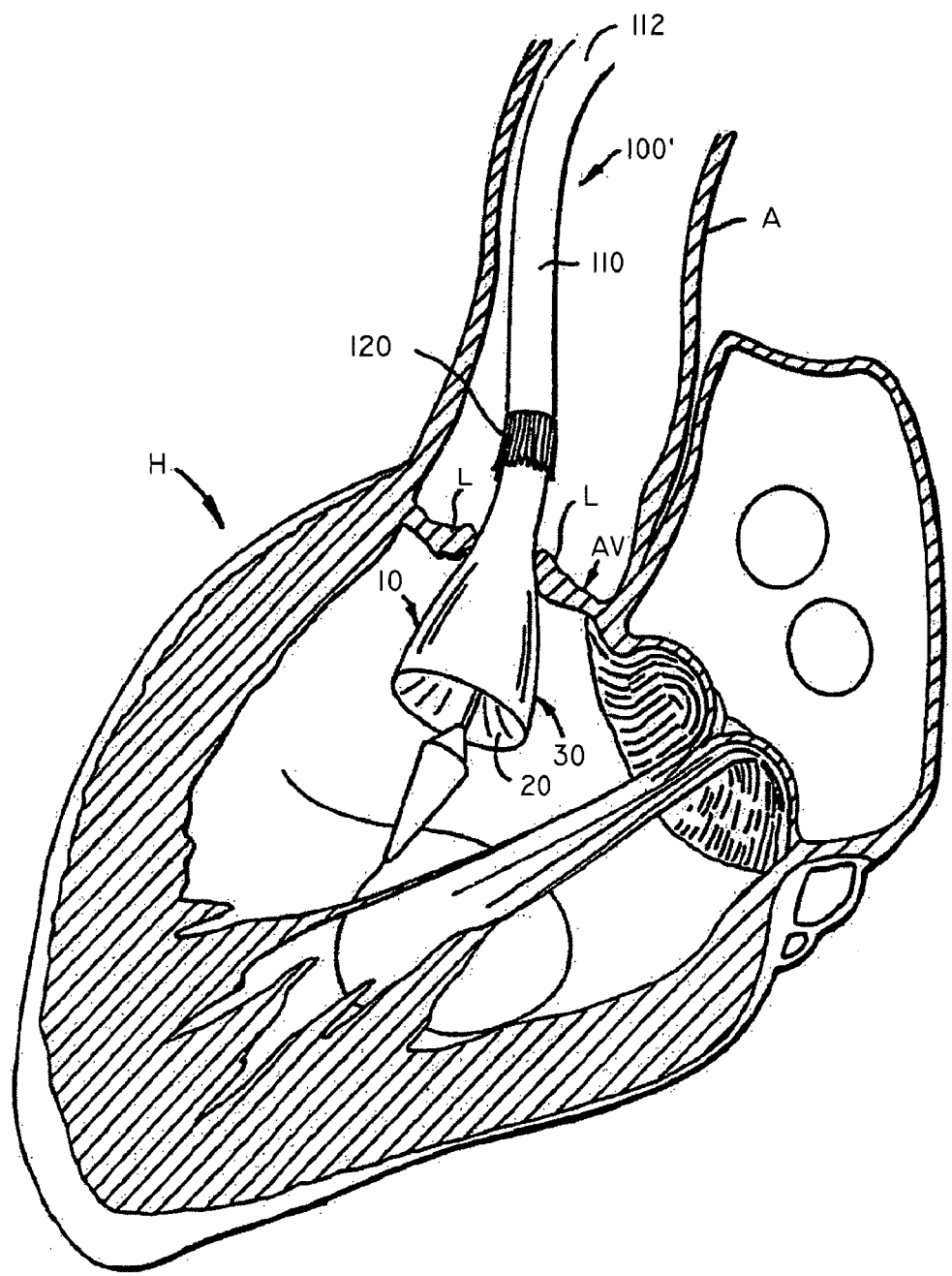
Figure 6C:
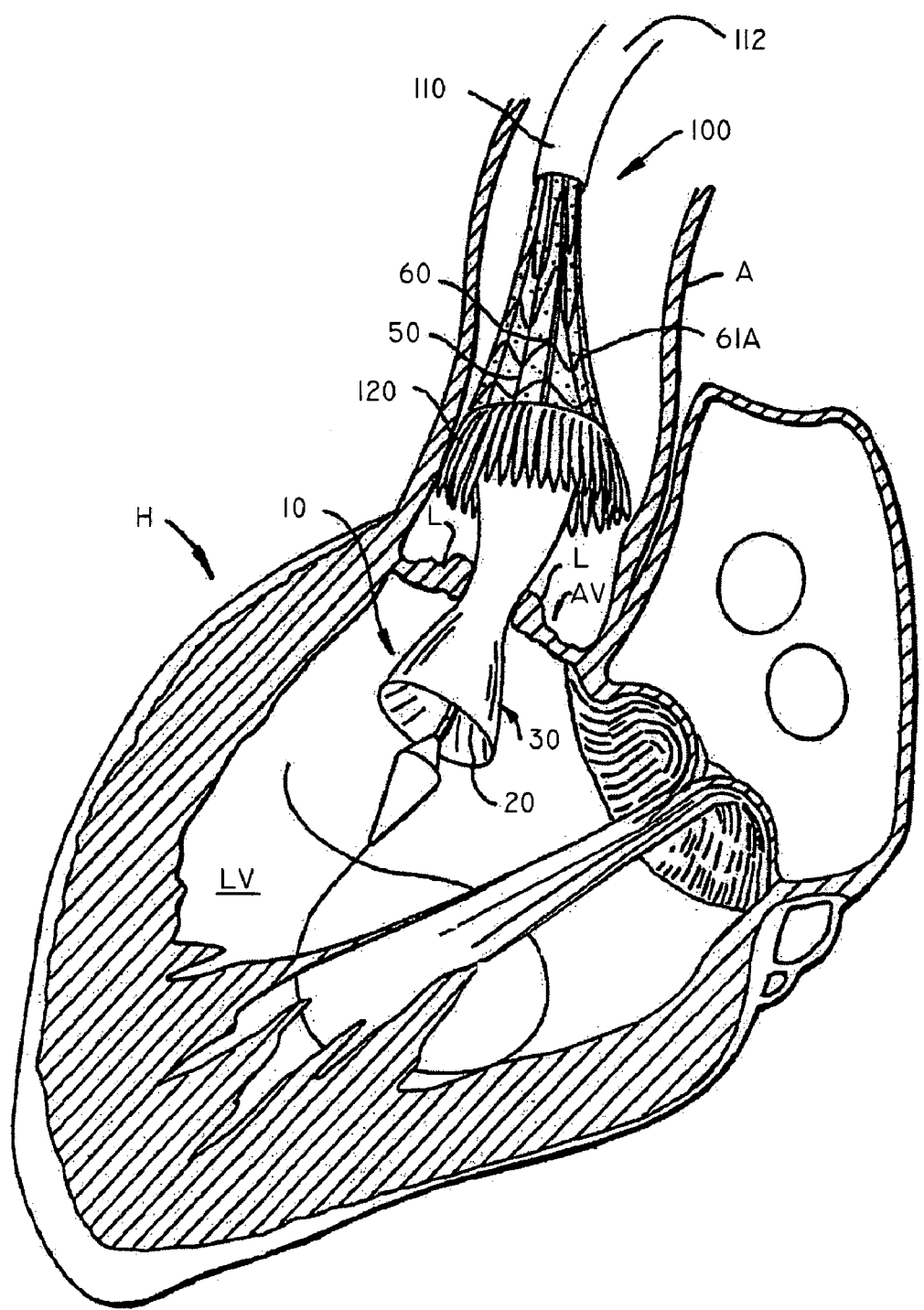

As seen in FIGS. 6B and 6C, apparatus 10 is deployed from lumen 112 of sheath 110, for example, under fluoroscopic guidance. Sheath 110 includes at its distal end leaflet engagement elements 120. Upon deployment, anchor 30 of apparatus 10 dynamically self-expands to a partially deployed configuration. This causes tubes 60 to also dynamically expand, as well as membrane filter (or braid) 61A and leaflet engagement elements 120. As when deployed via delivery system 100, deployment of apparatus 10 via delivery system 100' is fully reversible until locks 40 have been actuated.

Figure 7:
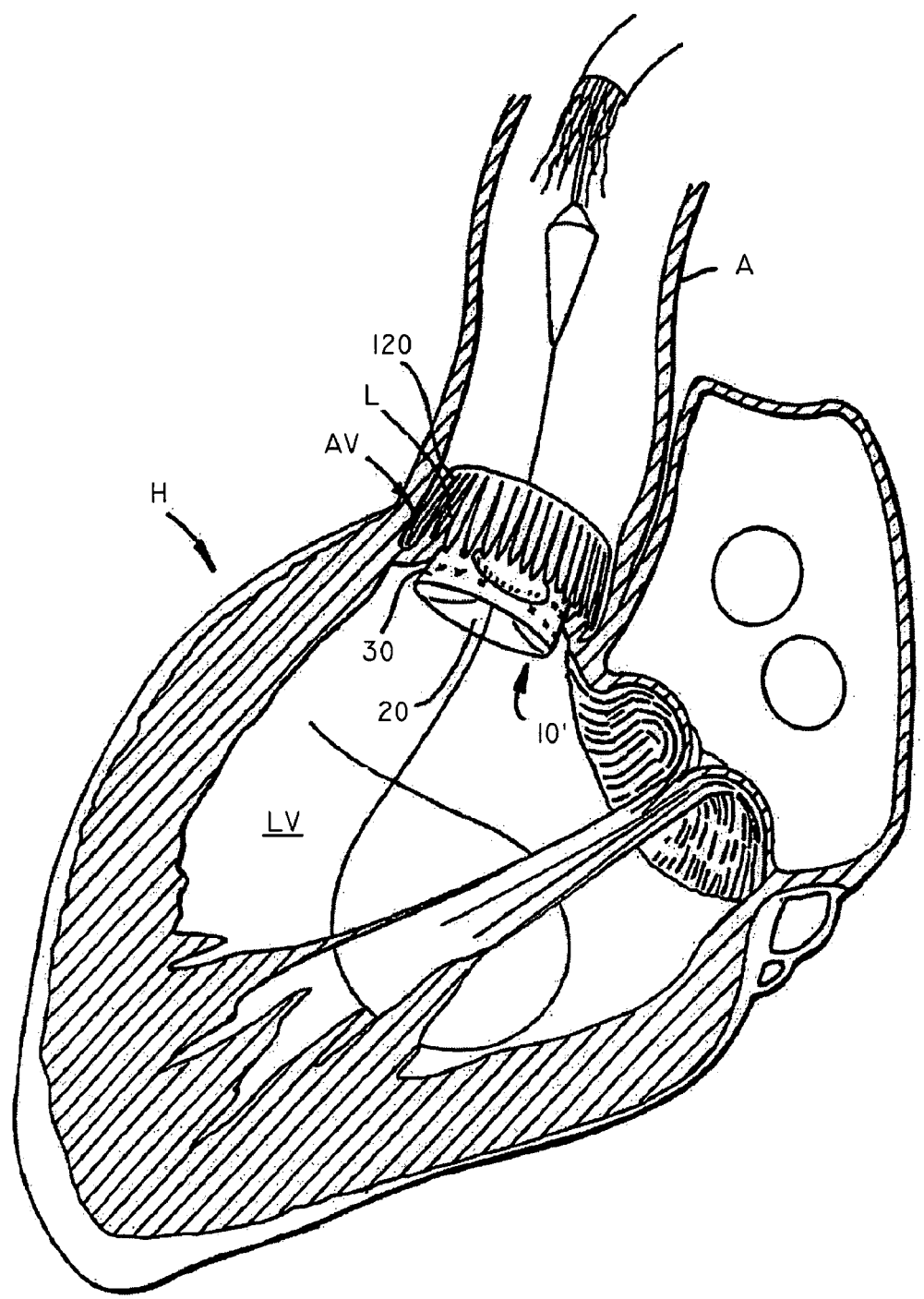
FIG. 7 illustrates a deployed anchor with leaflet engagement elements on the proximal end of the anchor.

Thus, delivery system 100' comprises leaflet engagement element 120, which preferably self-expands along with anchor 30. In preferred embodiments, the distal end of leaflet engagement elements 120 expands a greater radial distance than anchor 30. Moreover, engagement elements 120 may be disposed between tubes 60 of delivery system 100' and lip region 32 of anchor 30. However, leaflet engagement elements 120 may also be disposed on the proximal end of an anchor (as is illustrated in FIG. 7). Leaflet engagement elements 120 releasably engage the anchor. As seen in FIG. 6C, the leaflet engagement elements 120 are initially deployed proximal of the patient's native valve leaflets L. Apparatus 10 and element 120 then may be advanced/dynamically repositioned until engagement element positively registers against the leaflets, thereby ensuring proper positioning of apparatus 10. The leaflet engagement element engages with the proximal edges of the native valve leaflets and/or the commissural attachments. The leaflet engagement element need not extend all the way to the distal edge of the native leaflets (the leaflet pockets). In preferred embodiments, a leaflet engagement element length is less than about 20 mm, more preferably less than about 15 mm, or more preferably less than about 10 mm. Once leaflet engagement element 120 is registered against the native valve leaflets and/or commissural attachments, apparatus 10 deploys substantially distal to the coronary ostia of the heart.

In any of the embodiments herein, delivery system 100' can include filter structure 61A (e.g., filter membrane or braid) as part of push tubes 60 to act as an embolic protection element. Emboli can be generated during manipulation and placement of anchor from either diseased native leaflet or surrounding aortic tissue and can cause blockage. Arrows 61B in FIG. 6C show blood flow through filter structure 61A where blood is allowed to flow but emboli is trapped in the delivery system and removed with it at the end of the procedure.

Figure 6D:
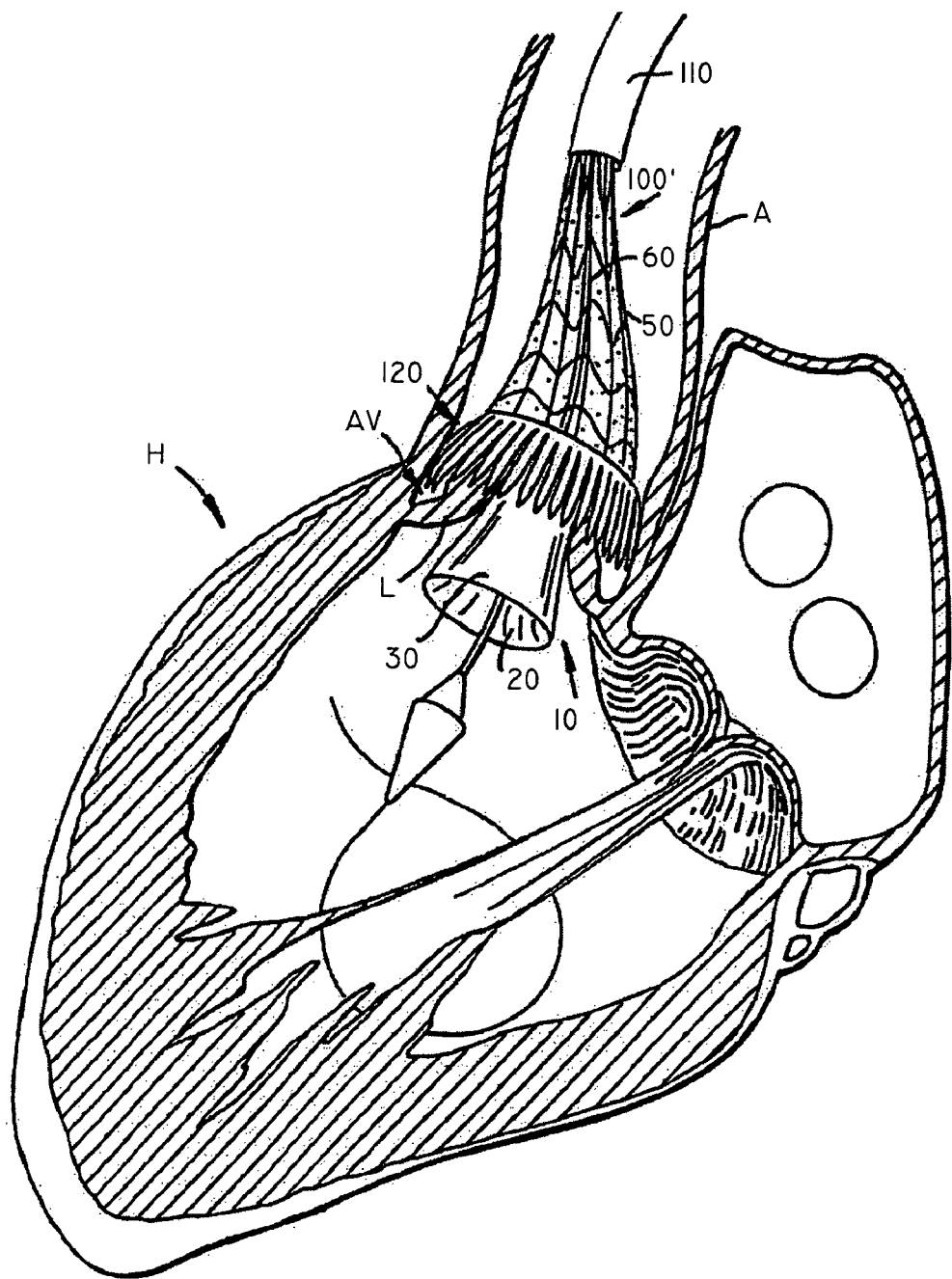
Figure 6E:
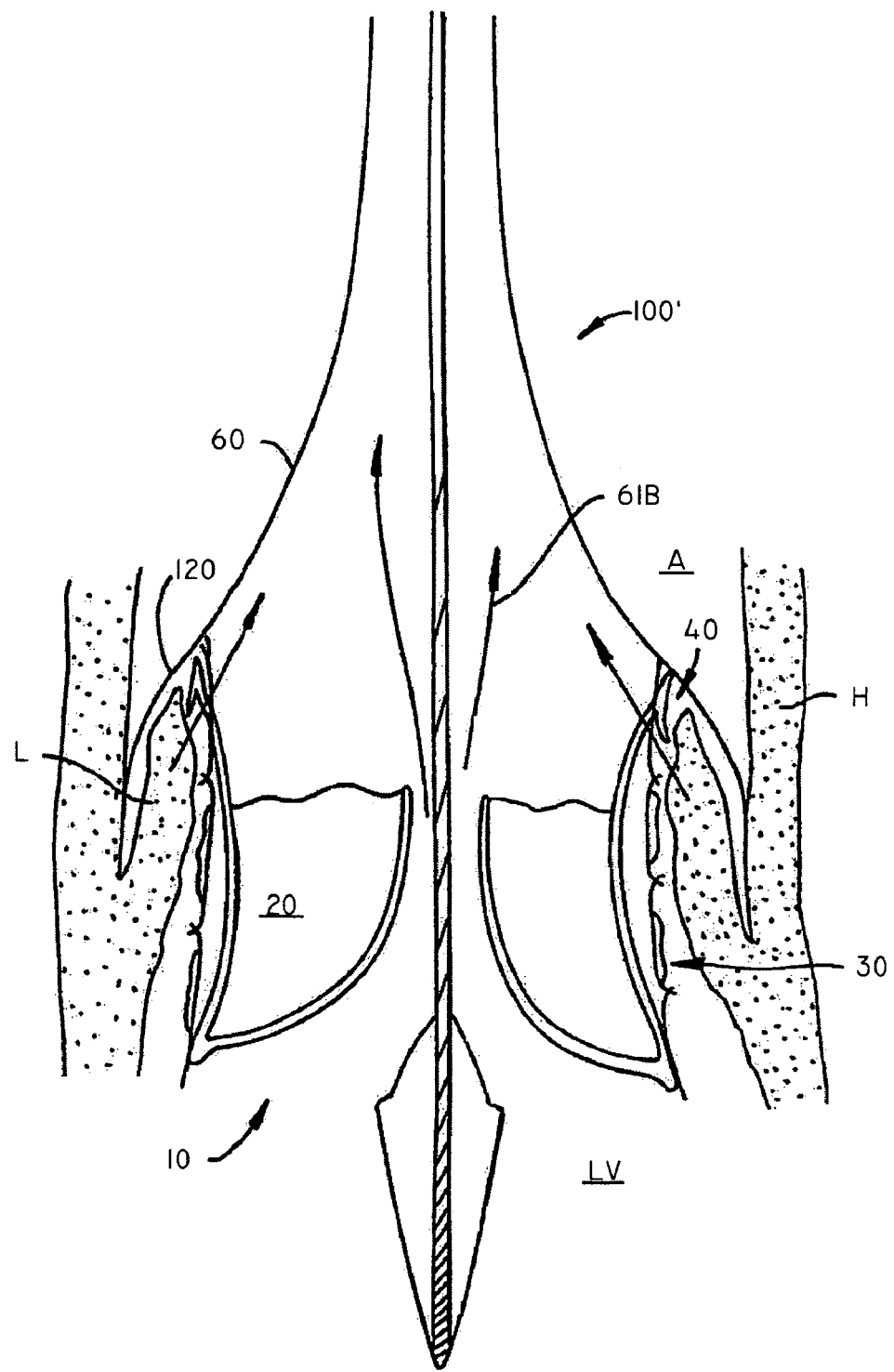

Active foreshortening may be imposed upon anchor 30 while element 120 is disposed proximal of the leaflets, as is illustrated in FIG. 6D. Active foreshortening can be accomplished by actuating distal anchor actuation elements (e.g., wires 50) and/or proximal anchor actuation elements (e.g., tubes 60). Upon positive registration of element 120 against leaflets L, element 120 precludes further distal migration of apparatus 10 during additional foreshortening, thereby reducing a risk of improperly positioning the apparatus. FIG. 6E details engagement of element 120 against the native leaflets.

Figure 6F:
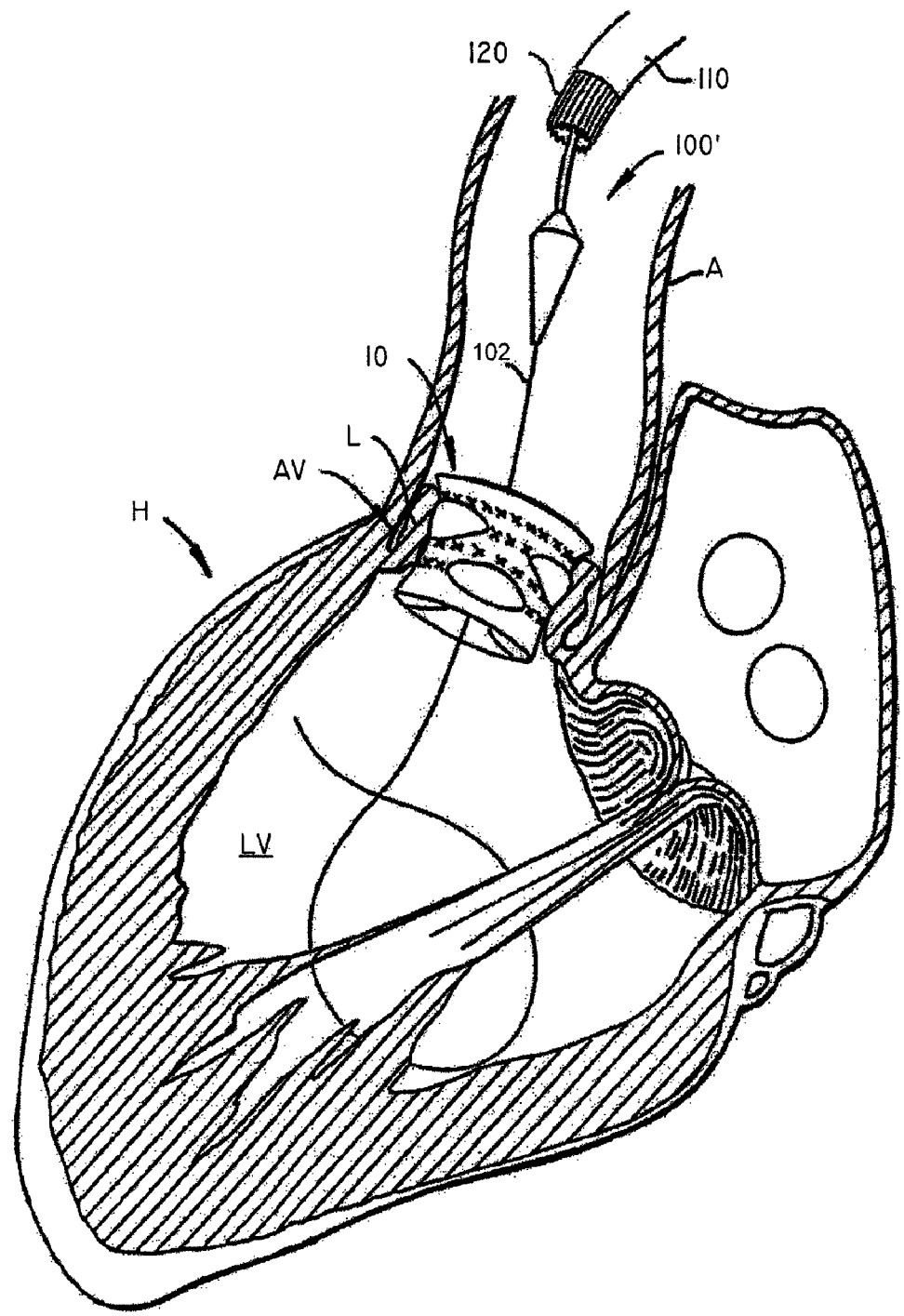

As seen in FIG. 6F, once apparatus 10 is fully deployed, anchor 30 may be locked (reversibly or irreversibly). Subsequently, structure 61A leaflet engagement, elements 120, wires 50 and/or tubes 60 may be decoupled from the apparatus, and delivery system 100' may be removed from the patient, thereby completing the procedure.

FIG. 7 illustrates an alternative embodiment of the apparatus of FIGS. 6A-F described above, wherein leaflet engagement elements 120 are coupled to anchor 30 of apparatus 10' rather than to delivery system 100. In the embodiment illustrated in FIG. 7, leaflet engagement elements 120 remain implanted near the patient's native heart valve after the deployment of apparatus 10' and removal of delivery system 100. Leaflets L may be sandwiched between the proximal region of anchor 30 and leaflet engagement element 120 in the fully deployed configuration. In this manner, element 120 positively registers apparatus 10' relative to the leaflets L and precludes distal migration of the apparatus over time.

Figure 8A:
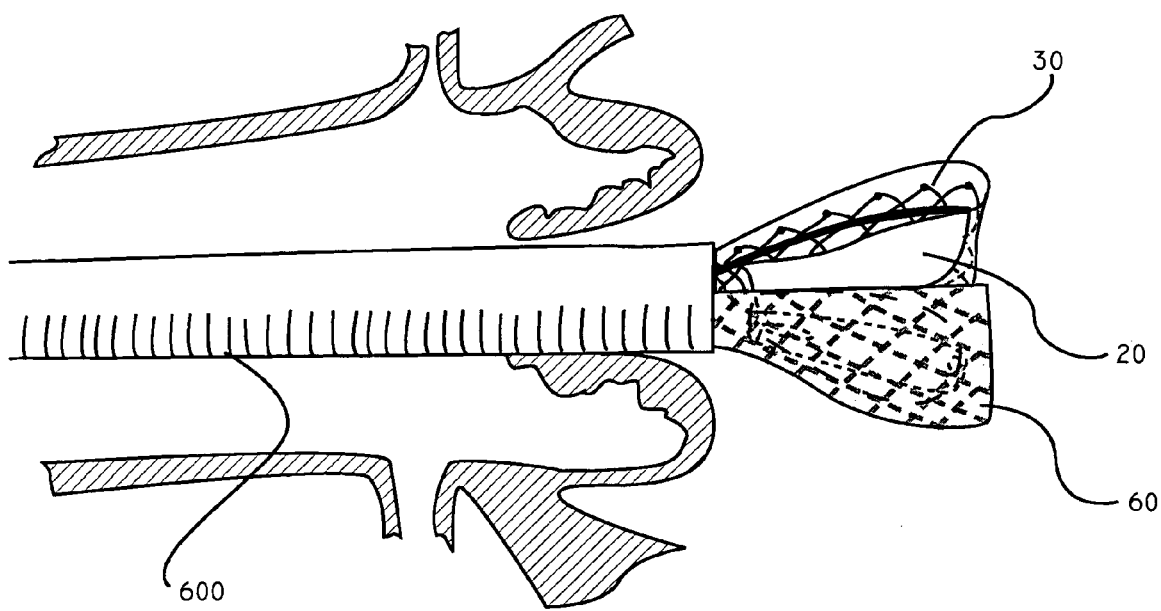
FIGS. 8A-8C illustrate deployment of an anchor with anchor registration elements and a seal.
Figure 8B:
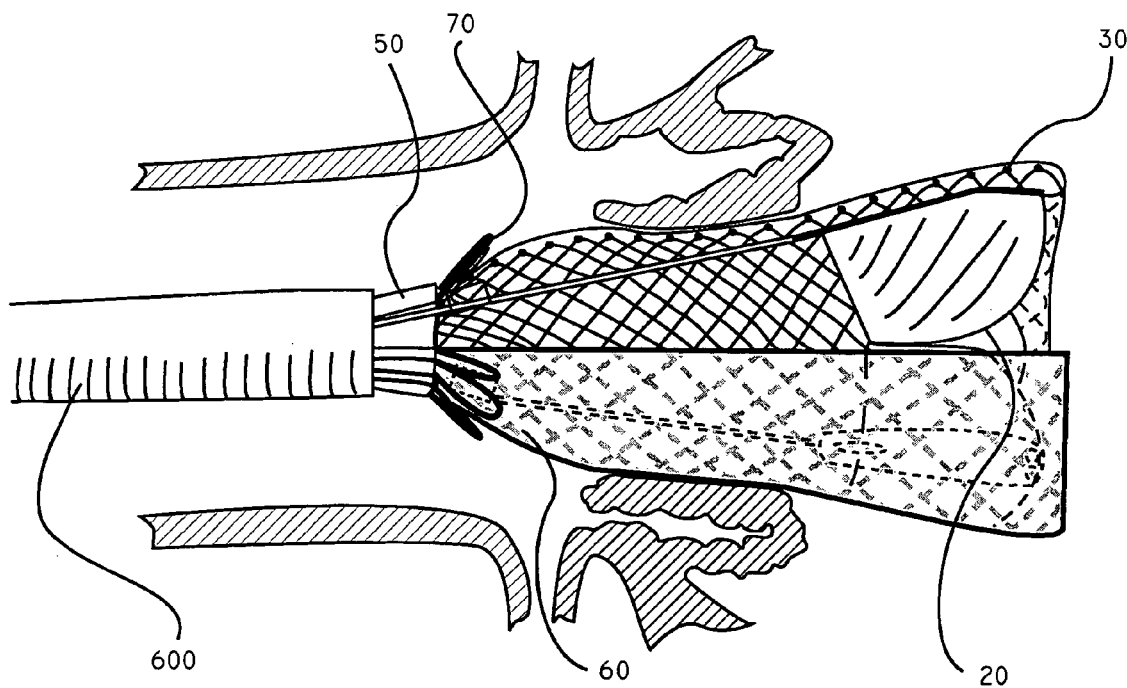
Figure 8C:
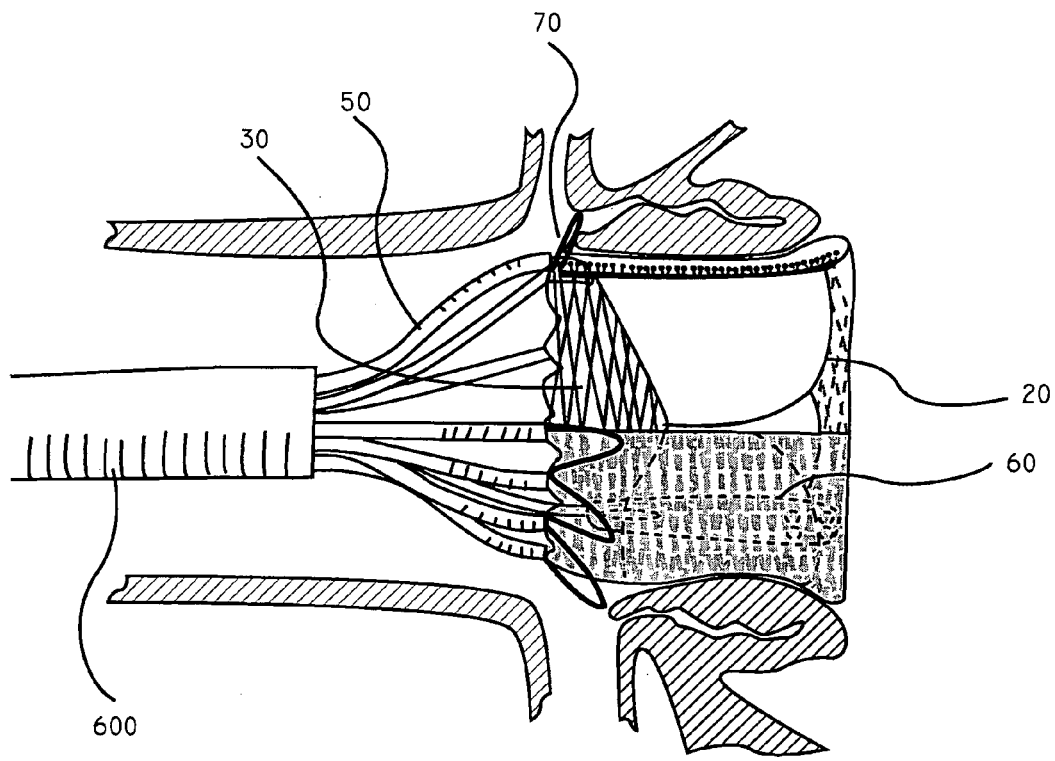

FIGS. 8A-8C illustrate another embodiment for endovascularly delivering an apparatus of the present invention. In FIG. 8A, a catheter 600 is delivered percutaneously in a retrograde fashion to the aortic valve. The catheter passes through the native aortic valve before an operator actuates the unseathing of the anchor/valve apparatus. As the sheathing catheter is pulled proximally out of the native valve, anchor 30 and replacement valve 20 become unsheathed. Immediately the portion of the unsheathed anchor 30 dynamically self-expands to its "at rest" position, and replacement valve 20 within the anchor regains an uncollapsed structure, allowing it to begin to function. In preferred embodiments in its "at rest" position, anchor 30 presses against the native leaflets limiting blood from flowing in between the anchor and leaflet. Also, in preferred embodiments, anchor 30 portions relatively adjacent to the valve is externally covered by a seal 60, more preferably the entire exterior contour of anchor 30 excluding the leaflet engagement elements is externally covered by a seal, or more preferably the entire contour of anchor 30 including the external face of the leaflet engagement elements is externally covered by a seal. A seal can be composed of any material that prevents or limits the flow of blood through the anchor. In preferred embodiments, a seal is composed of a thin, elastic polymer or any other type of fabric. The seal can be attached by any means known in the art to the anchor and, in some embodiments, to the distal end of the valve. In preferred embodiments, a seal is attached to the anchor by suturing.

In FIG. 8B, as the catheter is further pulled proximally, the proximal end of anchor 30 and fingers 50 are unsheathed. In this embodiment, it is possible to visualize that the seal covers the entire contour of the anchor including the external face of the leaflet engagement element 70. As soon as the proximal end of the anchor is exposed, it also dynamically expands. Furthermore, when fingers 50 become exposed, replacement valve 20 begins to function permitting blood to flow through replacement valve 20, between fingers 50, and around the catheter 600. This also permits blood to flow into the coronary ostias. In other embodiments where the seal does not cover the proximal end of the anchor, the replacement valve can begin to function as soon as the unsealed portion of the anchor is unsheathed. This causes the leaflet engagement elements 70 to radially expand to their heat set position and engage with the native heart leaflets.

Next, FIG. 8C, as the apparatus is actively foreshortened using proximal (e.g., fingers) and/or distal actuators (e.g., wires 50), the leaflet engagement elements positively register with the native valve leaflets. Foreshortening can cause seal 60 to bunch up and create pleats. These pleats can then fill pockets thereby improving the paravalvular seal. In preferred embodiments, wherein the leaflet engagement elements are covered with a seal, at least a portion of the seal is also positioned between the native valve leaflets and the aortic wall. Once the anchor is fully compressed within the aortic valve, the anchor is locked, the fingers and post mandrels are disengaged, and the seal is adapted to further limit blood flow around the replacement valve. The catheter is subsequently withdrawn, leaving behind valve 20, seal 60 and anchor 70. When ftilly deployed, the anchor is substantially distal to the coronary ostia of the patient such that it will not interfere with blood flow through the ostia.

Figure 9A:
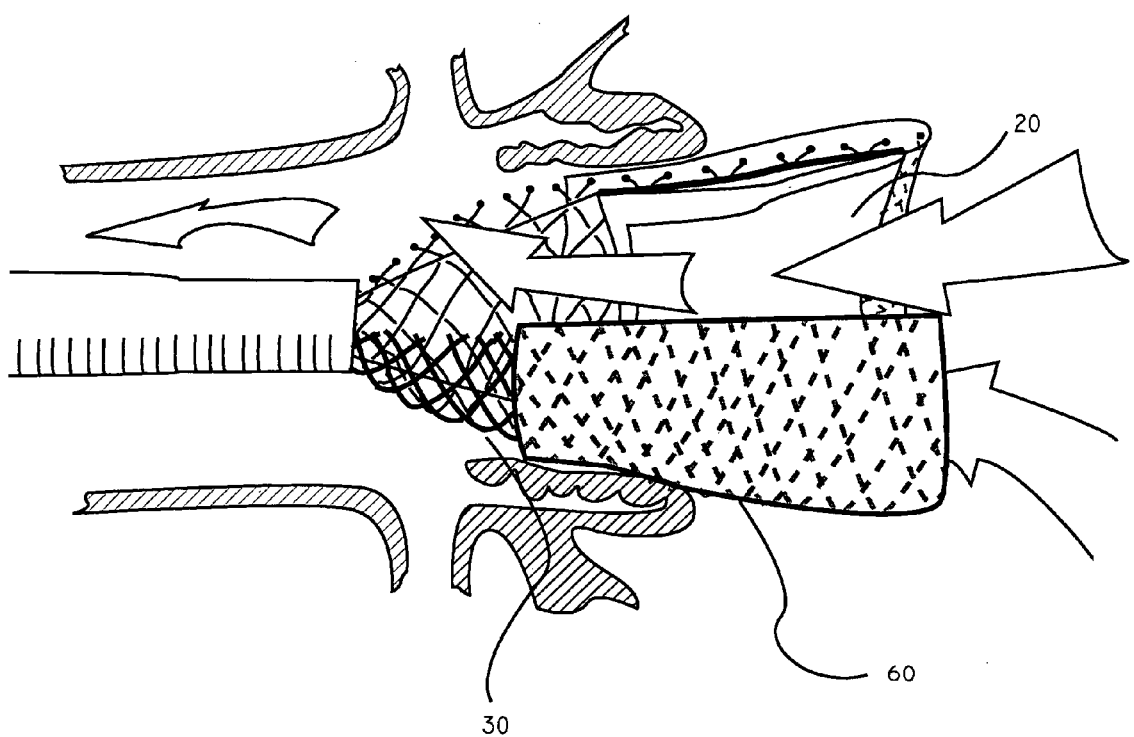
FIGS. 9A-9B illustrate an embodiment of the apparatus with a seal that does not reach the proximal end of the anchor during both systole and diastole.
Figure 9B:
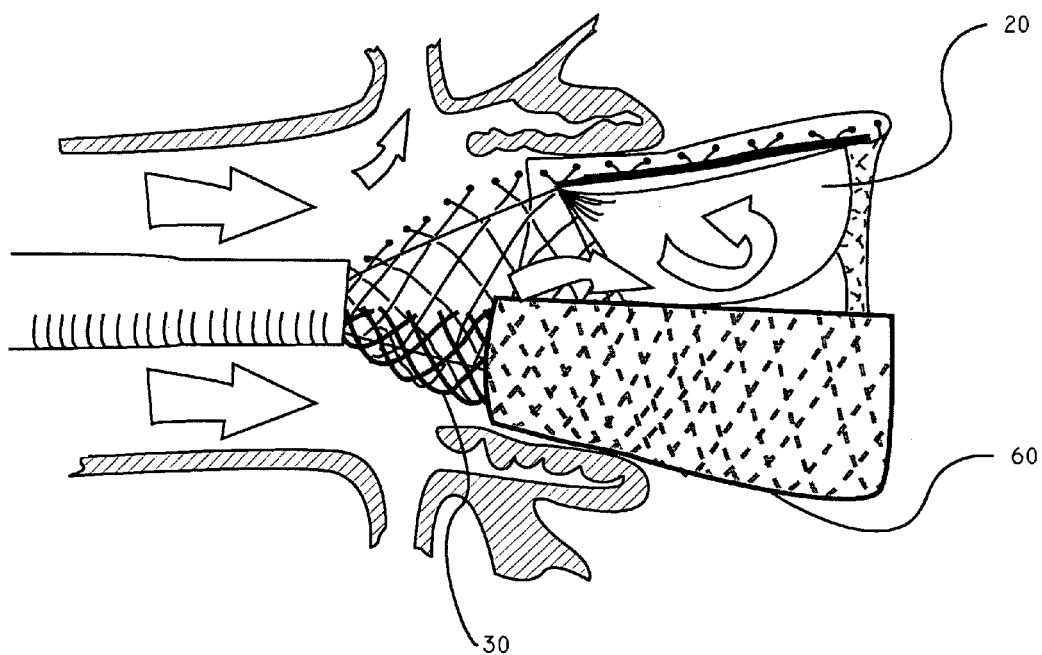

FIGS. 9A-9B illustrate an embodiment wherein only a distal portion anchor 30 is covered by seal 60 and wherein anchor 30 is only partially deployed since the blood can escape through the proximal end of the anchor braid. As anchor 30 in this embodiment is unsheathed, it presses against the native valve leaflets. At this point replacement valve 20 is functional even though anchor 30 is not fully deployed since blood can escape through the proximal end of the anchor braid. This allows blood to flow through replacement valve 20 and out of holes in the distal end of anchor 30 during systole (FIG. 9A) while preventing backflow during diastole (FIG. 9B).

Figure 10A:
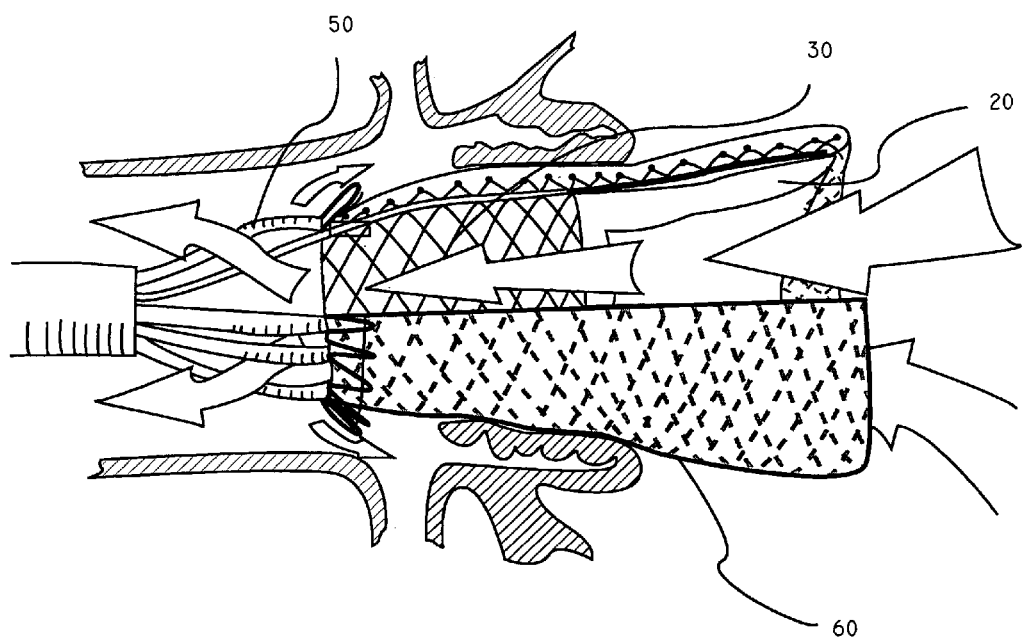
FIGS. 10A-10B illustrate an embodiment of the apparatus with a seal that reaches the proximal end of the anchor during both systole and diastole.
Figure 10B:
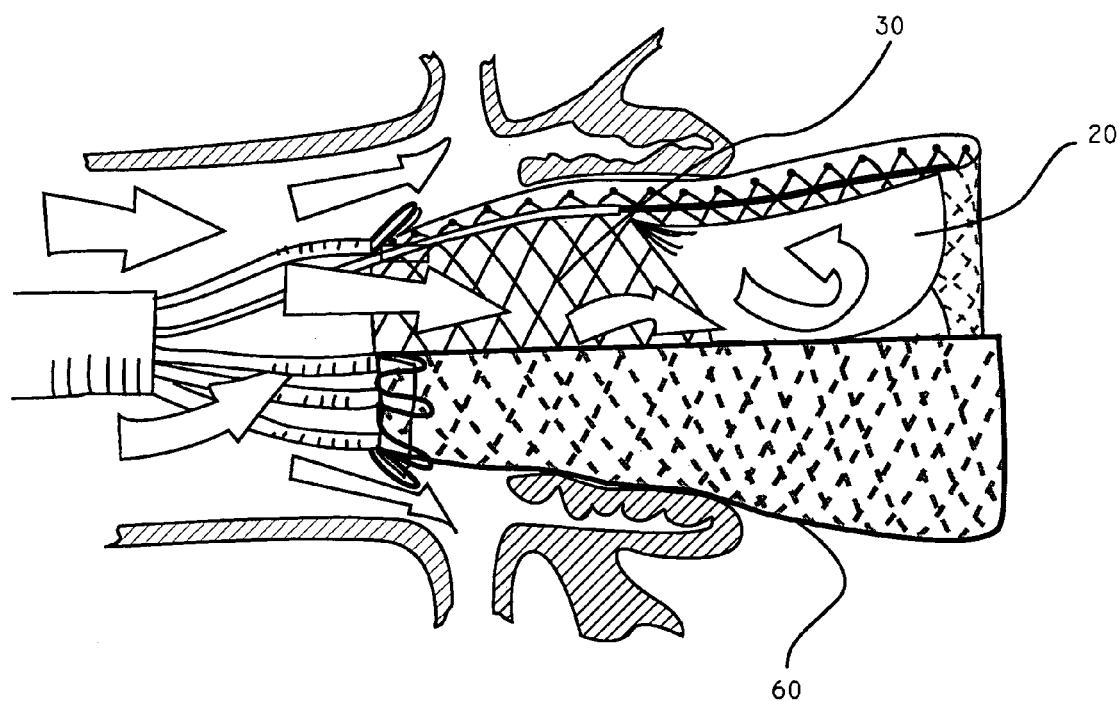

FIGS. 10A-10B illustrate a similar embodiment wherein seal 60 around anchor 30 surrounds the entire contour of anchor 30. In this embodiment, valve 20 does not become functional until both anchor 30 and a portion of fingers 50 are unsheathed. As soon as a portion of fingers 50 is unsheathed, replacement valve 20 is fully functional. This allows blood to flow through replacement valve 20 and anchor 30, out of fingers 50, and around catheter 60 into the aorta and coronary ostias during systole. Similarly, during diastole, replacement valve 20 closes preventing blood backflow from entering the chamber.

In any of the embodiments herein the anchor is preferably a self-expanding anchor braid. Anchor braid of the present invention can be made from one or more wires, more preferably 2-20 wires, more preferably 3-15 wires, or more preferably 4-10 wires. Moreover, the density of the braid can be modified by various forms of weave used.

FIGS. 11A-11D illustrate various anchor braid embodiments contemplated by the present invention.

FIG. 11A illustrates two groups of cells or two braids interwoven in the center. The top group of cells forms a more open weave than the bottom group of cells, which forms a denser weave.

FIG. 11B illustrates another embodiment of an anchor braid having three groups of cells. The top and bottom (proximal and distal) edges of the anchor braid have denser cells than the central portion of the anchor. Also, the edges of the anchor are woven from a thinner filament than the central portion.

In another embodiment illustrated by FIG. 11C, all three sections of an anchor valve are woven by more than one wire. The wires of each section are made of a different material and/or thickness. Wires at the sectional boundaries may or may not interconnect with wires from a different section. Each of the sections of the braid anchor may be composed of a different number of wires.

FIG. 11D illustrates another embodiment of a braided anchor having three sections. In this embodiment, all sections are composed of a single wire. The proximal and distal sections/edges of the braided anchor have the same pitch. The central region of the braided anchor has a different pitch than the edge sections.

FIGS. 12A-12E illustrate side views of braided anchor having more than one braid pitch. Varying pitch within the anchor allows localized variations in foreshortening across the anchor, as greater foreshortening is achieved by higher pitch of the braid. Moreover, the localized foreshortening features allow for the design of a braid which incorporates various diameters depending upon the amount of foreshortening. (The greater the foreshortening, the greater the diameter increase upon deployment.)

Figure 12A:
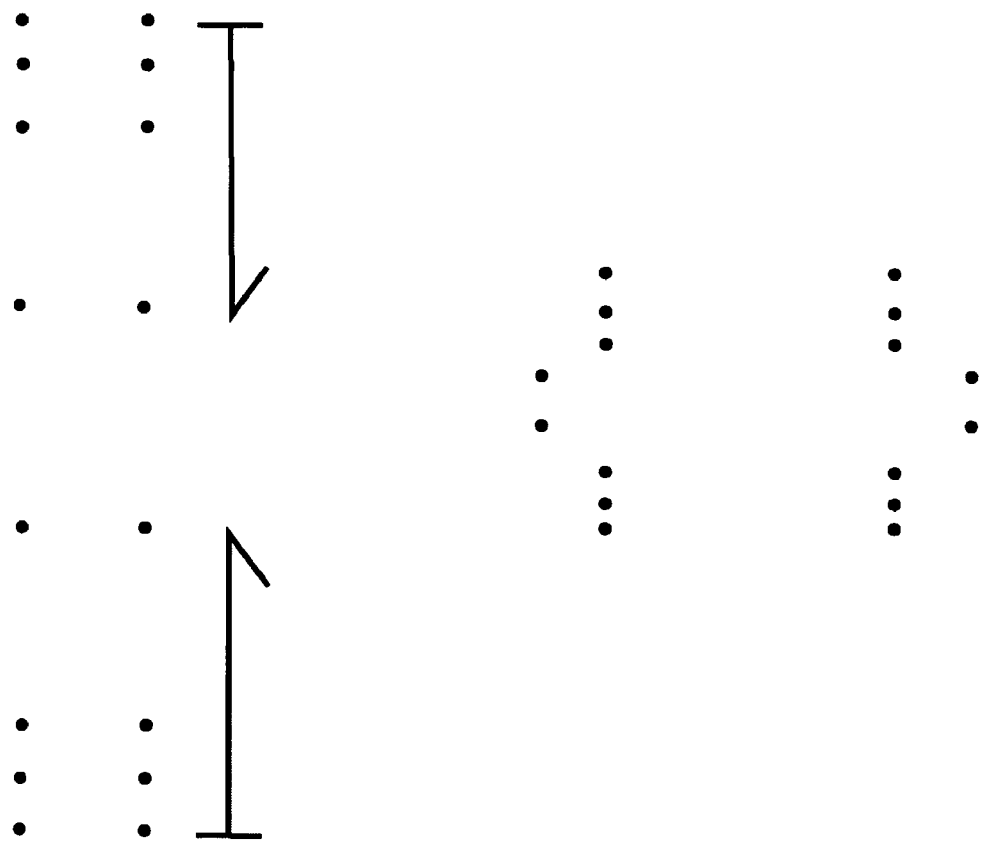
FIGS. 12A-12E are schematic side views of a deployment process for an anchor braid.

FIG. 12A, is a side view representation of the braided anchor of FIG. 11D. On the left side of the figure, the expanded anchor is illustrated having a denser weave (shorter pitch) at the distal and proximal ends; hence the dots are located closer to each other. The middle section of the anchor is composed of a looser weave that is generated by a higher pitch braid and is represented by dots that are farther away from each other. On the right side of the figure, the braided anchor is foreshortened and the dots are collapsed closer to each other. In this case, the central portion of the anchor foreshortened more than the proximal and distal edges.

Figure 12B:

FIG. 12B illustrates a side view of a foreshortened braided anchor that is created by low pitch at the edges and high pitch in the middle.

Figure 12C:

FIG. 12C illustrates a side view of a foreshortened braided anchor that is created by high pitch edges and low pitch middle section.

Figure 12D:

FIG. 12D illustrates a side view of a foreshortened braided anchor that includes a sealing feature or space filling feature at both ends. This type of anchor can be created by a high pitch braid at edges, low pitch braid in the middle and heat setting the edges to curl upon unsheathing. These end features can be useful in facilitating anchoring by functioning as a locator and/or sealing. In preferred embodiment the curled ends of the anchor in FIG. 12D can be used as leaflet engagement elements.

Figure 12E:

FIG. 12E illustrates a side view of a foreshortened braided anchor that is associated with an everting valve or locational features. In preferred embodiments, the middle section of the anchor may be composed of thicker wire(s) than edge section (s). The everting feature at the proximal end can function as a leaflet engagement element as disclosed herein.

FIGS. 13A-13E illustrate an example of the process of deploying an anchor, such as the one illustrated in FIG. 12B above.

Figure 13A:
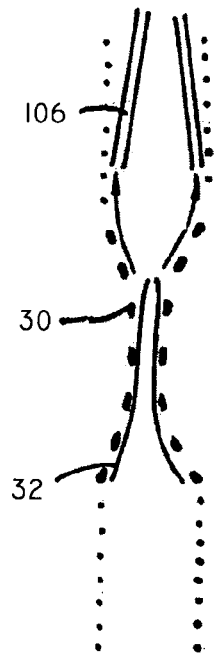
FIGS. 13A-13E are schematic views of different weave configurations for an anchor braid.

FIG. 13A illustrates a braided anchor 30 in its expanded or elongated configuration. The anchor is composed of three sections. The distal and proximal sections of the anchor are made of a fine weave, low pitch braid and the middle section of the anchor is made of a thicker thread and higher pitch braid. The distal and proximal section are preferably heat set to roll upon unsheathing, though some rolling may occur simply from active for shortening of the fine weave braid. In preferred embodiments, the filaments of the fine weave braid are less than 0.01 cm, or more preferably less than 0.005 cm in thickness. On the other hand, thicker filaments of the middle section are preferably 0.01 cm or greater in thickness or more preferably 0.015 cm or greater in thickness. Posts 32 are coupled to the middle section of the anchor. For deployment, tubes (or fingers) 106 are coupled to the anchor's middle section.

Figure 13B:
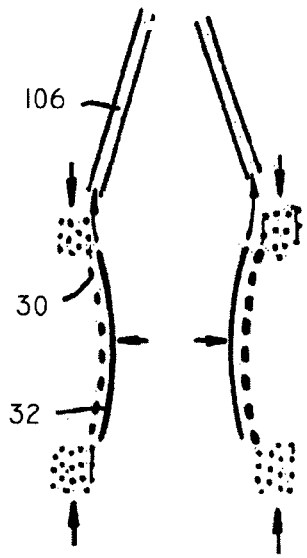

FIG. 13B illustrates an anchor during the process of deployment after the anchor is unsheathed. The anchor is pushed distally by tubes and pulled proximally by wires and begins foreshortening. In some embodiment the distal section rolls up and can act as a locator, assisting the operator in locating the aortic valve, or as a seal preventing leakage. In some embodiments, the proximal section may roll down and be used as a leaflet engagement element to prevent distal migration or as a proximal seal.

Figure 13C:
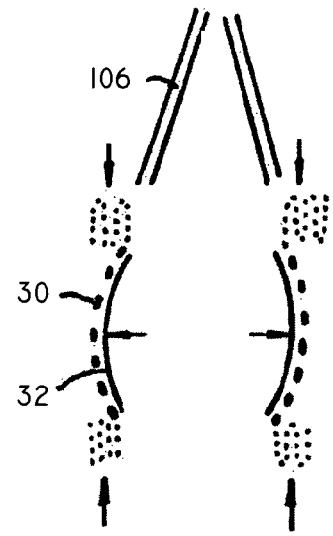

In FIG. 13C, the device may be configured such that the middle section of the valve may form an hour glass shape or a round shape. The tubes may subsequently be removed as described before.

Figure 13D:

FIG. 13D is another illustration of the braided anchor in its elongated configuration.

Figure 13E:
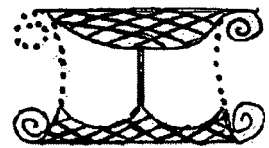

FIG. 13E is another illustration of the braided anchor in its foreshortened configuration.

FIGS. 14A-14C illustrate the process of forming a pleated seal around a replacement valve to prevent leakage. FIG. 14A illustrates a fabric seal 380 prior to deployment and foreshortening of the anchor/valve apparatus. In FIG. 14A, the fabric seal 380 extends from the distal end of valve 20 proximally over anchor 30 during delivery. During deployment, as illustrated in FIG. 14B, anchor 30 foreshortens and the fabric seal 380 bunches up to create fabric flaps and pockets that extend into spaces formed by the native valve leaflets 382. The bunched up fabric or pleats occur, in particular, when the pockets are filled with blood in response to backflow blood pressure. The pleating can create a seal around the replacement valve. FIG. 14C illustrates anchor 30, surrounded by fabric seal 380 in between native valve leaflets 382. In preferred embodiments, at least a portion of a seal is captured between the leaflets and the wall of the heart when the anchor is fully deployed.

FIGS. 15A-H show another embodiment of a replacement heart valve apparatus in accordance with the present invention. Apparatus 450 comprises replacement valve 460 (see FIGS. 17B and 18C) disposed within and coupled to anchor 470. Replacement valve 460 is preferably biologic, e.g. porcine, but alternatively may be synthetic. Anchor 470 preferably is fabricated from self-expanding materials, such as a stainless steel wire mesh or a nickel-titanium alloy ("Nitinol"), and comprises lip region 472, skirt region 474, and body regions 476a, 476b and 476c. Replacement valve 460 preferably is coupled to skirt region 474, but alternatively may be coupled to other regions of the anchor. As described hereinbelow, lip region 472 and skirt region 474 are configured to expand and engage/capture a patient's native valve leaflets, thereby providing positive registration, reducing paravalvular regurgitation, reducing device migration, etc.

Figure 15A:
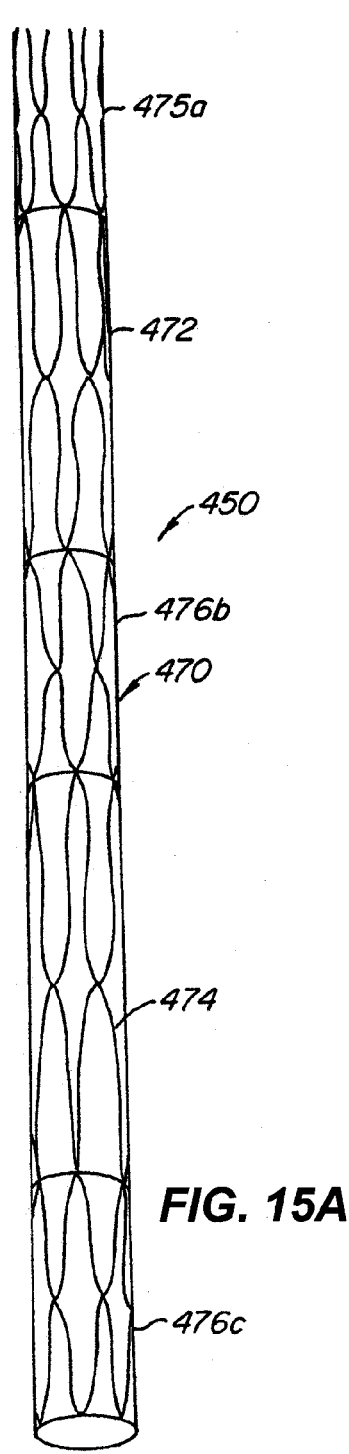

As seen in FIG. 15A, apparatus 450 is collapsible to a delivery configuration, wherein the apparatus may be delivered via delivery system 410. Delivery system 410 comprises sheath 420 having lumen 422, as well as wires 424a and 424b seen in FIGS. 15D-15G. Wires 424a are configured to expand skirt region 474 of anchor 470, as well as replacement valve 460 coupled thereto, while wires 424b are configured to expand lip region 472.

Figure 15B:
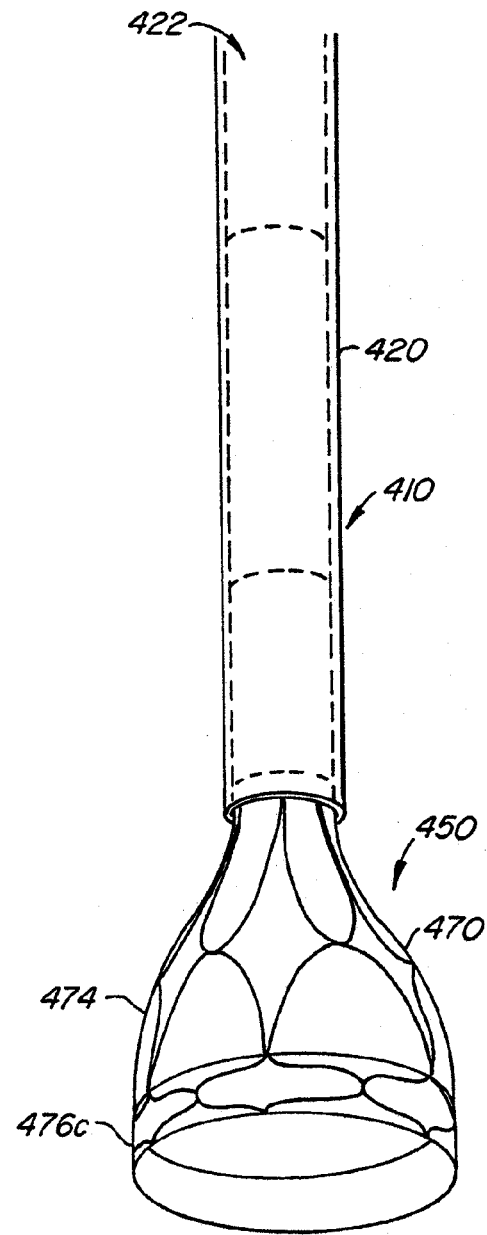

As seen in FIG. 15B, apparatus 450 may be delivered and deployed from lumen 422 of catheter 420 while the apparatus is disposed in the collapsed delivery configuration. As seen in FIGS. 15B-15D, catheter 420 is retracted relative to apparatus 450, which causes anchor 470 to dynamically self-expand to a partially deployed configuration. Wires 424a are then retracted to expand skirt region 474, as seen in FIGS. 15E and 15F. Preferably, such expansion may be maintained via locking features described hereinafter.

Figure 15G:
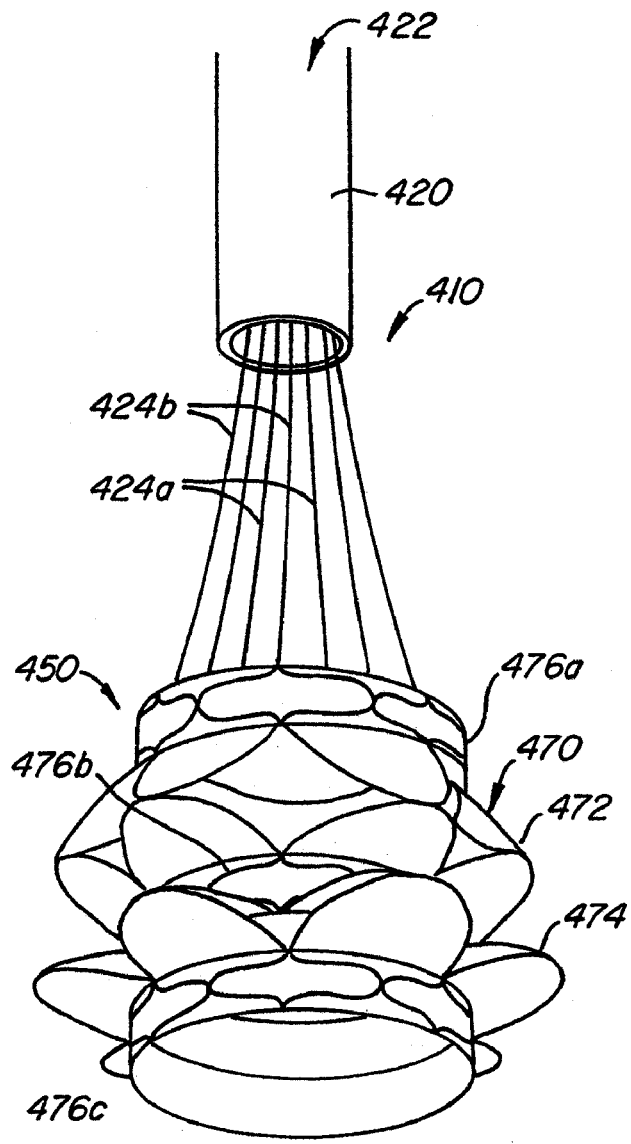
Figure 15H:
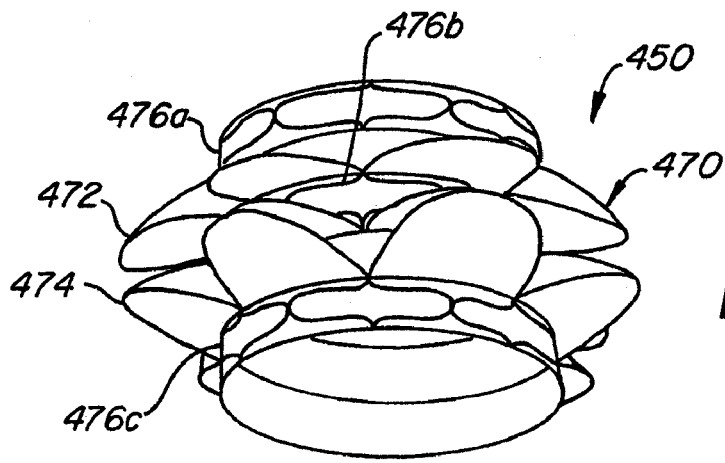

In FIG. 15G, wires 424b are retracted to expand lip region 472 and fully deploy apparatus 450. As with skirt region 474, expansion of lip region 472 preferably may be maintained via locking features. After both lip region 472 and skirt region 474 have been expanded, wires 424 may be removed from apparatus 450, thereby separating delivery system 410 from the apparatus. Delivery system 410 then may be removed, as seen in FIG. 15H.

As will be apparent to those of skill in the art, lip region 472 optionally may be expanded prior to expansion of skirt region 474. As yet another alternative, lip region 472 and skirt region 474 optionally may be expanded simultaneously, in parallel, in a step-wise fashion or sequentially. Advantageously, delivery of apparatus 450 is fully reversible until lip region 472 or skirt region 474 has been locked in the expanded configuration.

Figures 16A, 16B:
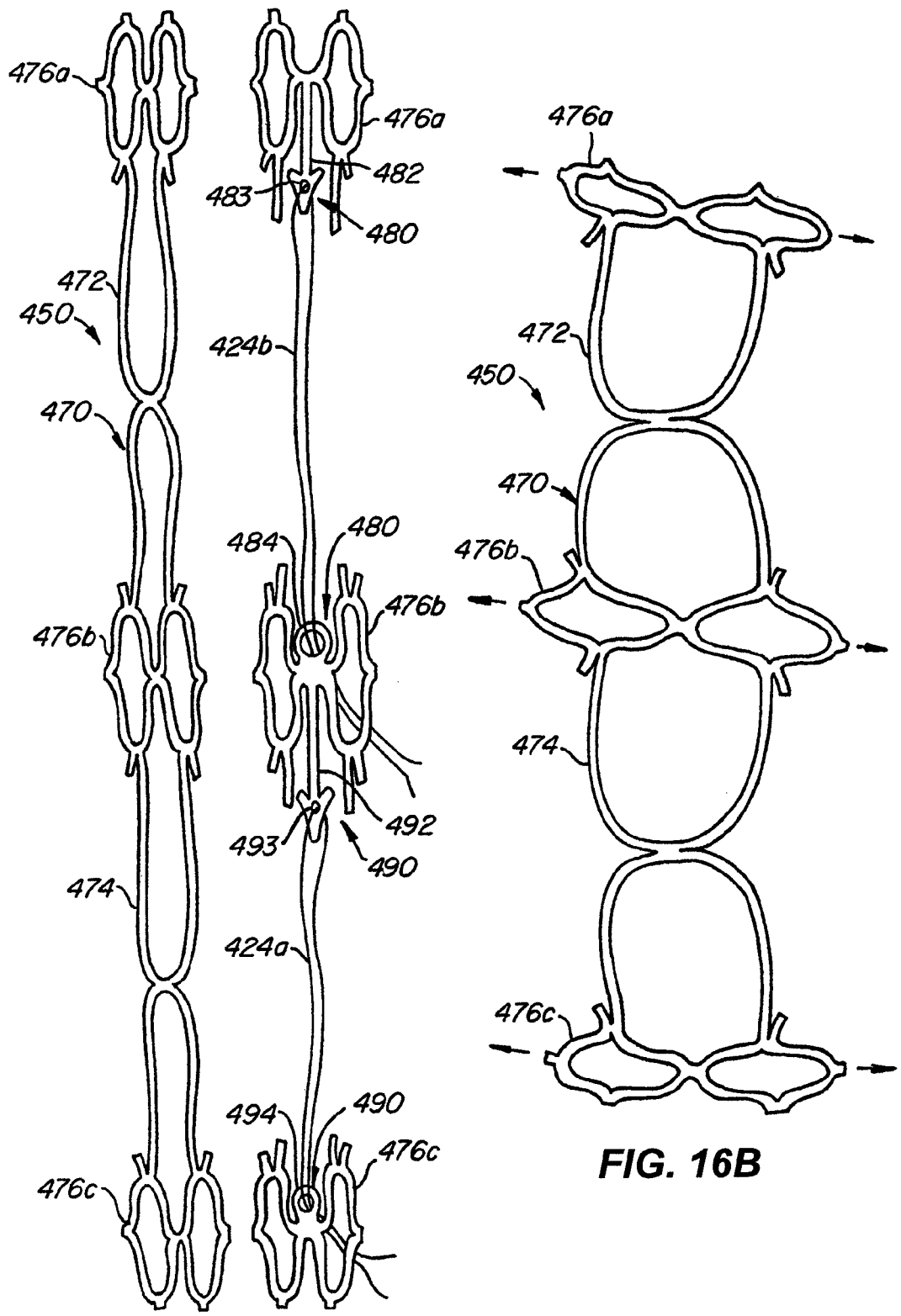
FIGS. 16A-E show more detail of the anchor of the embodiment shown in FIGS. 15A-H.

With reference now to FIGS. 16A-E, individual cells of anchor 470 of apparatus 450 are described to detail deployment and expansion of the apparatus. In FIG. 16A, individual cells of lip region 472, skirt region 474 and body regions 476a, 476b and 476c are shown in the collapsed delivery configuration, as they would appear while disposed within lumen 422 of sheath 420 of delivery system 410 of FIG. 15. A portion of the cells forming body regions 476, for example, every 'nth' row of cells, comprises locking features.

Body region 476a comprises male interlocking element 482 of lip lock 480, while body region 476b comprises female interlocking element 484 of lip lock 480. Male element 482 comprises eyelet 483. Wire 424b passes from female interlocking element 484 through eyelet 483 and back through female interlocking element 484, such that there is a double strand of wire 424b that passes through lumen 422 of catheter 420 for manipulation by a medical practitioner external to the patient. Body region 476b further comprises male interlocking element 492 of skirt lock 490, while body region 476c comprises female interlocking element 494 of the skirt lock. Wire 424a passes from female interlocking element 494 through eyelet 493 of male interlocking element 492, and back through female interlocking element 494. Lip lock 480 is configured to maintain expansion of lip region 472, while skirt lock 490 is configured to maintain expansion of skirt region 474.

Figure 16C:
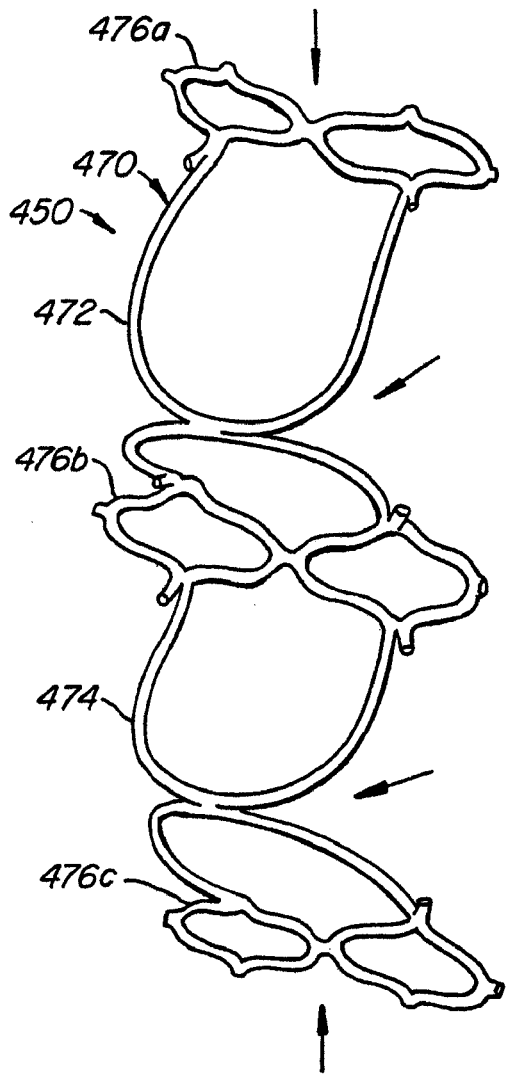
Figure 16D:
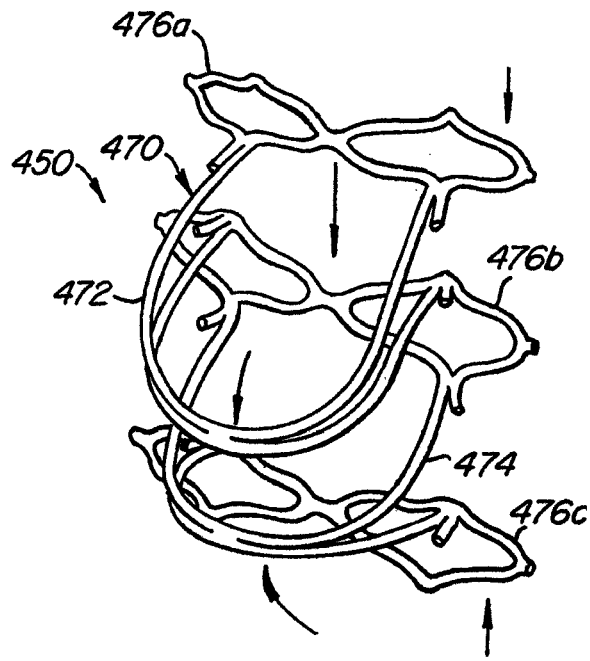
Figure 16E:
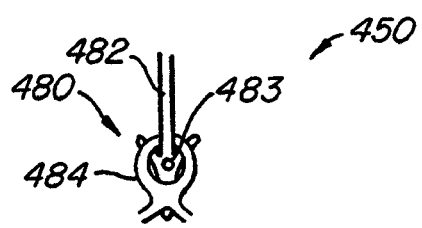

In FIG. 16B, anchor 470 is shown in the partially deployed configuration, e.g., after deployment from lumen 422 of sheath 420. Body regions 476, as well as lip region 472 and skirt region 474, self-expand to the partially deployed configuration. Full deployment is then achieved by retracting wires 424 relative to anchor 470, and expanding lip region 472 and skirt region 474 outward, as seen in FIGS. 16C and 16D. As seen in FIG. 16E, expansion continues until the male elements engage the female interlocking elements of lip lock 480 and skirt lock 490, thereby maintaining such expansion (lip lock 480 shown in FIG. 16E). Advantageously, deployment of apparatus 450 is fully reversible until lip lock 480 and/or skirt lock 490 has been actuated.

Figure 17A:
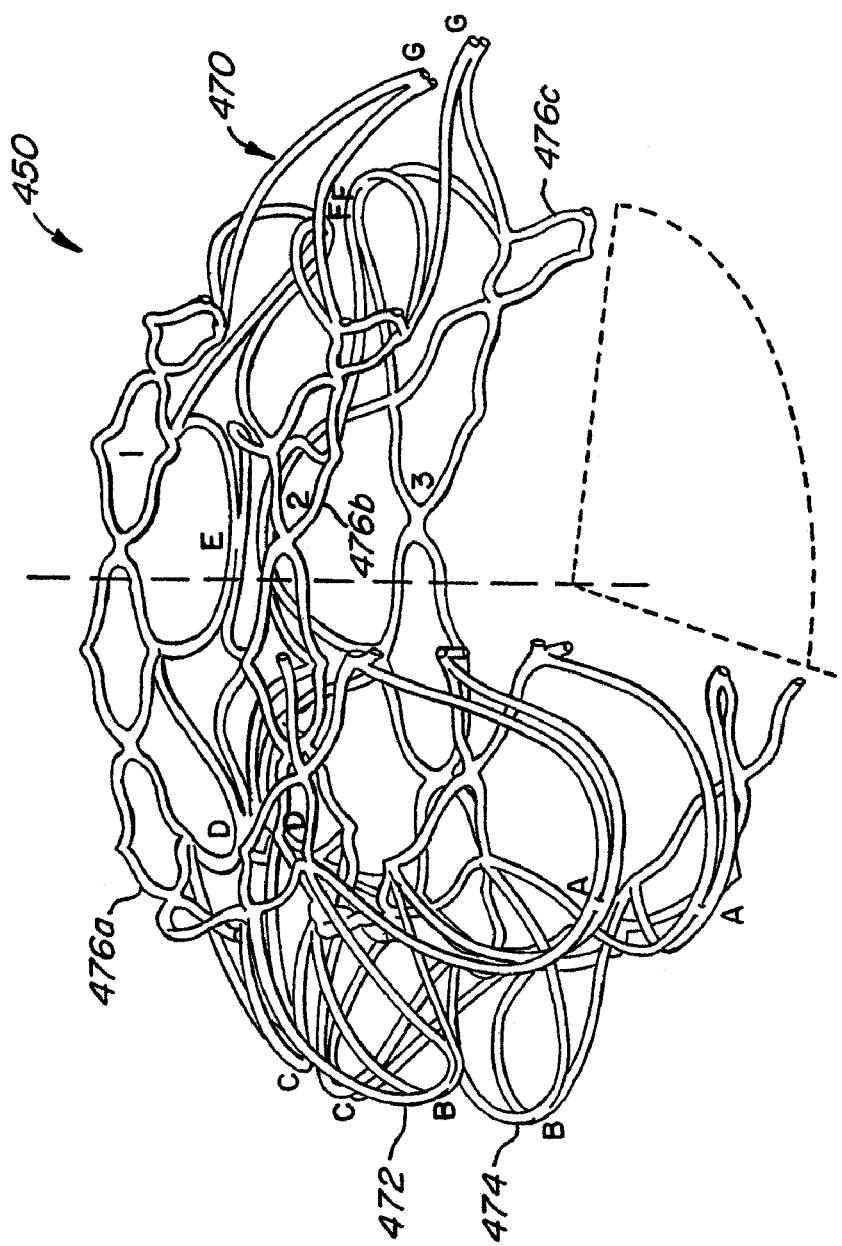
FIGS. 17A-B show other embodiments of the replacement heart valve and anchor of the invention.
Figure 17B:
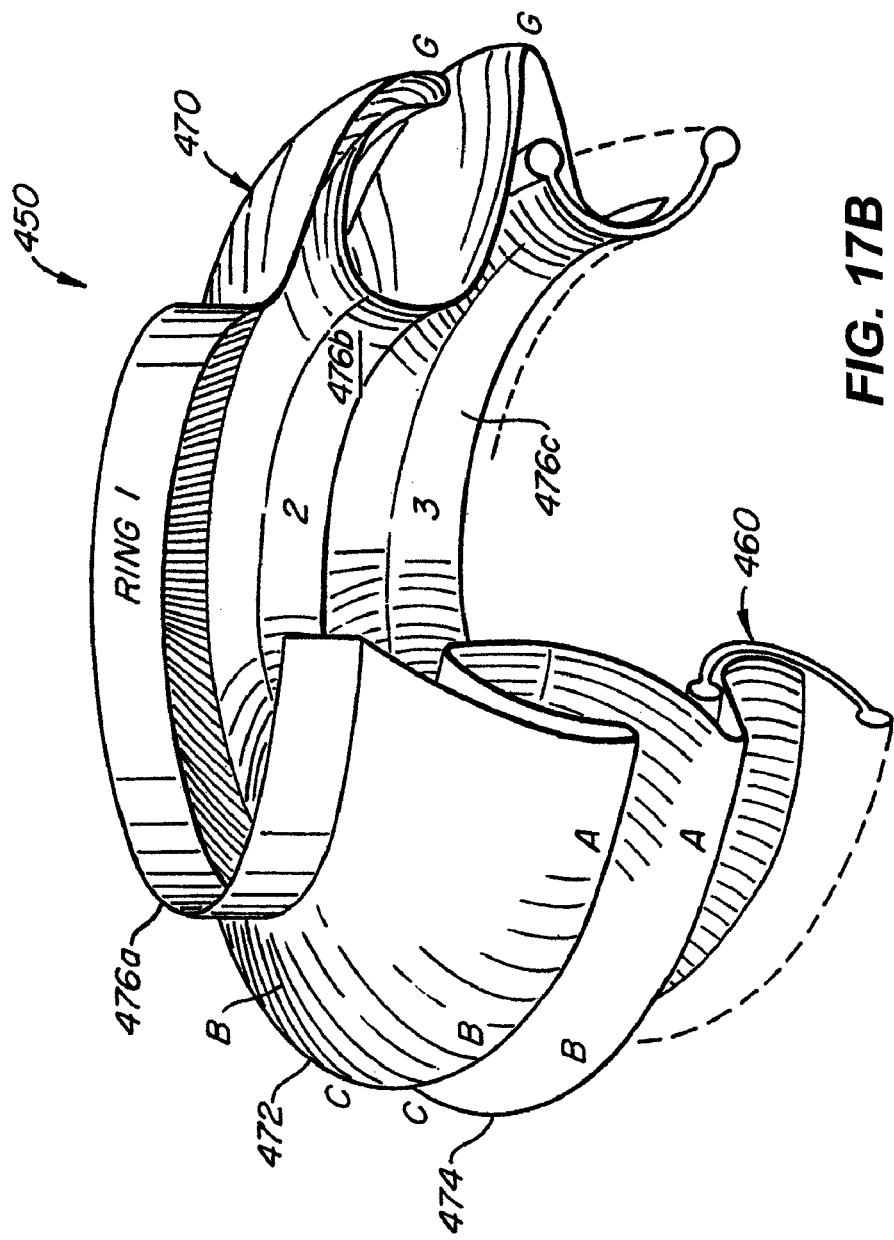

With reference to FIGS. 17A-B, isometric views, partially in section, further illustrate apparatus 450 in the fully deployed and expanded configuration. FIG. 17A illustrates the wireframe structure of anchor 470, while FIG. 17B illustrates an embodiment of anchor 470 covered in a biocompatible material B. Placement of replacement valve 460 within apparatus 450 may be seen in FIG. 17B. The patient's native valve is captured between lip region 472 and skirt region 474 of anchor 470 in the frilly deployed configuration (see FIG. 18B).

Figure 18A:
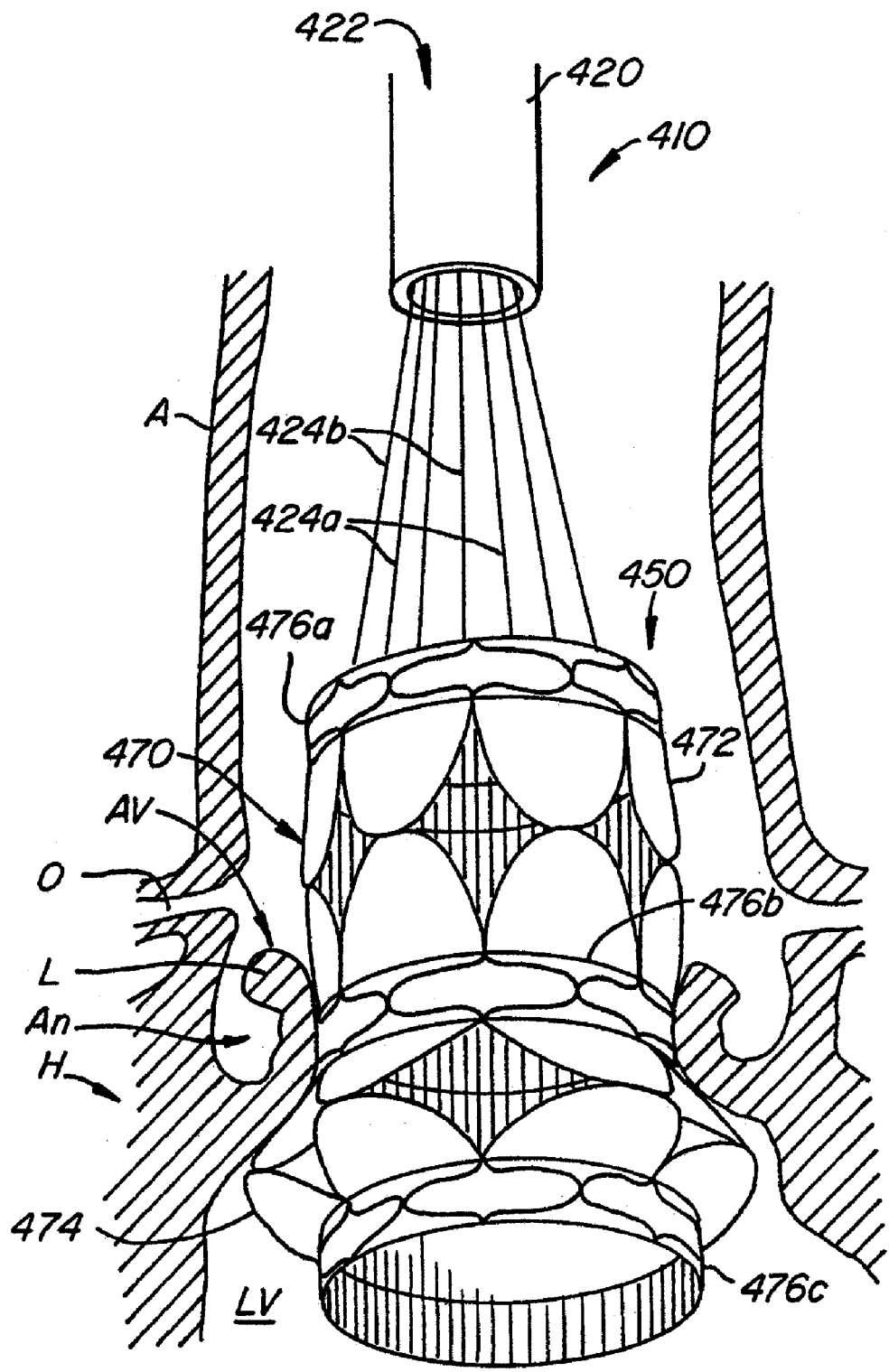
FIGS. 18A-C illustrate a method for endovascularly replacing a patient's diseased heart valve.
Figure 18B:
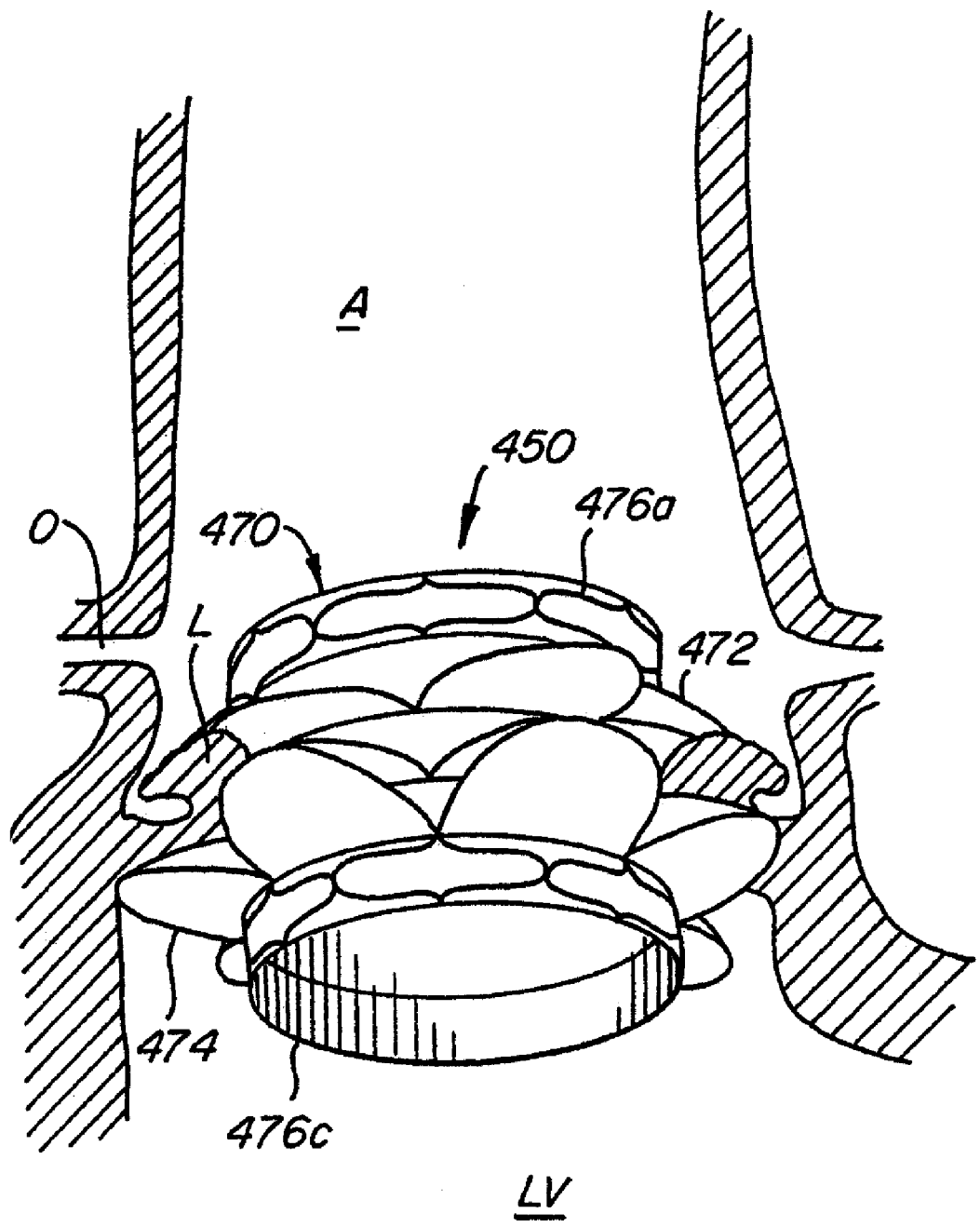
Figure 18C:
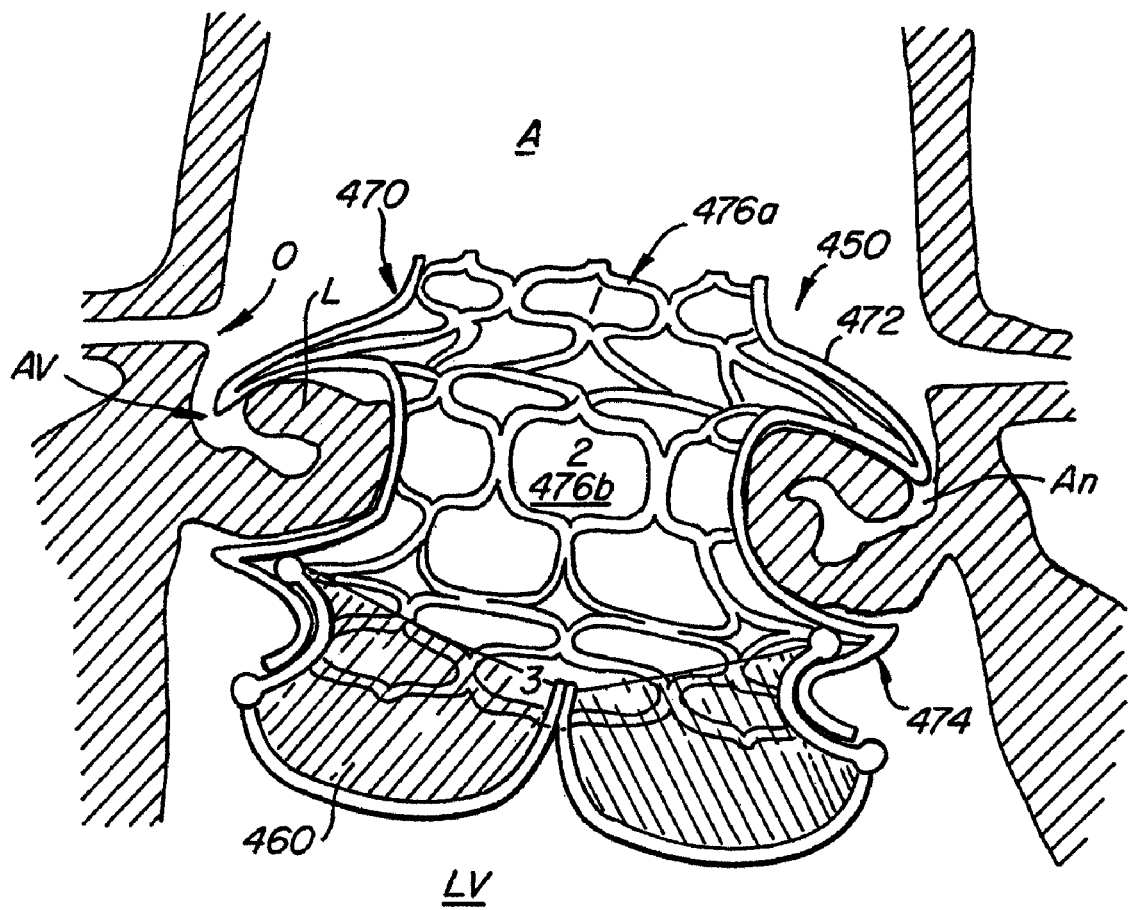

Referring to FIGS. 18A-C, in conjunction with FIGS. 15 and 16, a method for endovascularly replacing a patient's diseased aortic valve with apparatus 450 is described. Delivery system 410, having apparatus 450 disposed therein, is endovascularly advanced, preferably in a retrograde fashion, through a patient's aorta A to the patient's diseased aortic valve AV. Sheath 420 is positioned such that its distal end is disposed within left ventricle LV of the patient's heart H. As described with respect to FIG. 15, apparatus 450 is deployed from lumen 422 of sheath 420, for example, under fluoroscopic guidance, such that skirt section 474 is disposed within left ventricle LV, body section 476b is disposed across the patient's native valve leaflets L, and lip section 472 is disposed within the patient's aorta A. Advantageously, apparatus 450 may be dynamically repositioned to obtain proper alignment with the anatomical landmarks. Furthermore, apparatus 450 may be retracted within lumen 422 of sheath 420 via wires 424, even after anchor 470 has dynamically expanded to the partially deployed configuration, for example, to abort the procedure or to reposition sheath 420.

Once properly positioned, wires 424a are retracted to expand skirt region 474 of anchor 470 within left ventricle LV. Skirt region 474 is locked in the expanded configuration via skirt lock 490, as previously described with respect to FIG. 16. In FIG. 18A, skirt region 474 is maneuvered such that it engages the patient's valve annulus An and/or native valve leaflets L, thereby providing positive registration of apparatus 450 relative to the anatomical landmarks.

Wires 424b are then actuated external to the patient in order to expand lip region 472, as previously described in FIG. 15. Lip region 472 is locked in the expanded configuration via lip lock 480. Advantageously, deployment of apparatus 450 is fully reversible until lip lock 480 and/or skirt lock 490 has been actuated. Wires 424 are pulled from eyelets 483 and 493, and delivery system 410 is removed from the patient. As will be apparent, the order of expansion of lip region 472 and skirt region 474 may be reversed, concurrent, etc.

As seen in FIG. 18B, lip region 472 engages the patient's native valve leaflets L, thereby providing additional positive registration and reducing a risk of lip region 472 blocking the patient's coronary ostia O. FIG. 18C illustrates the same in cross-sectional view, while also showing the position of replacement valve 460. The patient's native leaflets are engaged and/or captured between lip region 472 and skirt region 474. Advantageously, lip region 472 precludes distal migration of apparatus 450, while skirt region 474 precludes proximal migration. It is expected that lip region 472 and skirt region 474 also will reduce paravalvular regurgitation.

With reference to FIGS. 19-21, a first embodiment of two-piece apparatus of the present invention adapted for percutaneous replacement of a patient's heart valve is described. As seen in FIG. 21, apparatus 510 comprises a two-piece device having custom-designed expandable anchor piece 550 of FIG. 19 and expandable replacement valve piece 600 of FIG. 20. Both anchor piece 550 and valve piece 600 have reduced delivery configurations and expanded deployed configurations. Both may be either balloon expandable (e.g. fabricated from a stainless steel) or self-expanding (e.g. fabricated from a nickel-titanium alloy ("Nitinol") or from a wire mesh) from the delivery to the deployed configurations.

When replacing a patient's aortic valve, apparatus 510 preferably may be delivered through the patient's aorta without requiring a transseptal approach, thereby reducing patient trauma, complications and recovery time. Furthermore, apparatus 510 enables dynamic repositioning of anchor piece 550 during delivery and facilitates positive registration of apparatus 510 relative to the native position of the patient's valve, thereby reducing a risk of device migration and reducing a risk of blocking or impeding flow to the patient's coronary ostia. Furthermore, the expanded deployed configuration of apparatus 510, as seen in FIG. 21D, is adapted to reduce paravalvular regurgitation, as well as to facilitate proper seating of valve piece 600 within anchor piece 550.

As seen in FIG. 19, anchor piece 550 preferably comprises three sections. Lip section 560 is adapted to engage the patient's native valve leaflets to provide positive registration and ensure accurate placement of the anchor relative to the patient's valve annulus during deployment, while allowing for dynamic repositioning of the anchor during deployment. Lip section 560 also maintains proper positioning of composite anchor/valve apparatus 510 post-deployment to preclude distal migration. Lip section 560 optionally may be covered or coated with biocompatible film B (see FIG. 21) to ensure engagement of the native valve leaflets. It is expected that covering lip section 560 with film B especially would be indicated when the native leaflets are stenosed and/or fused together Groove section 570 of anchor piece 550 is adapted to engage an expandable frame portion, described hereinbelow, of valve piece 600 to couple anchor piece 550 to valve piece 600. As compared to previously known apparatus, groove section 570 comprises additional material and reduced openings or gaps G, which is expected to reduce tissue protrusion through the gaps upon deployment, thereby facilitating proper seating of the valve within the anchor. Groove section 570 optionally may be covered or coated with biocompatible film B (see FIG. 21) to further reduce native valve tissue protrusion through gaps G.

Finally, skirt section 580 of anchor piece 550 maintains proper positioning of composite anchor/valve apparatus 510 post-deployment by precluding proximal migration. When replacing a patient's aortic valve, skirt section 580 is deployed within the patient's left ventricle. As with lip section 560 and groove section 570, skirt section 580 optionally may be covered or coated with biocompatible film B (see FIG. 21) to reduce paravalvular regurgitation. As will be apparent to those of skill in the art, all, a portion of, or none of anchor piece 50 may be covered or coated with biocompatible film B.

Figure 19A:
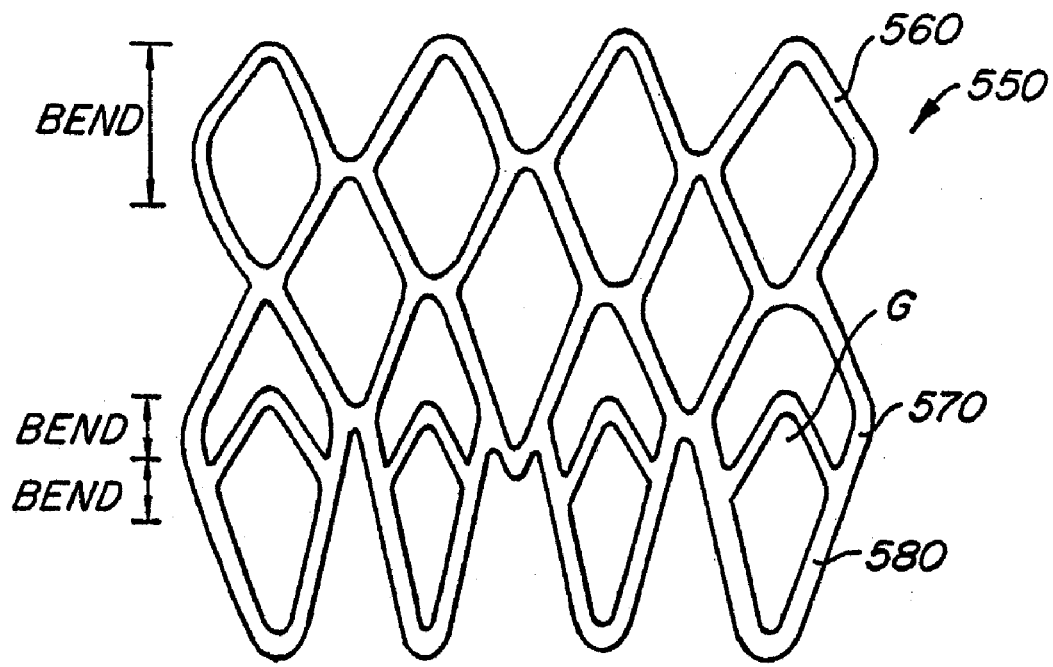
FIGS. 19A-B show an anchor for use in a two-piece replacement heart valve and anchor embodiment of the invention.
Figure 19B:
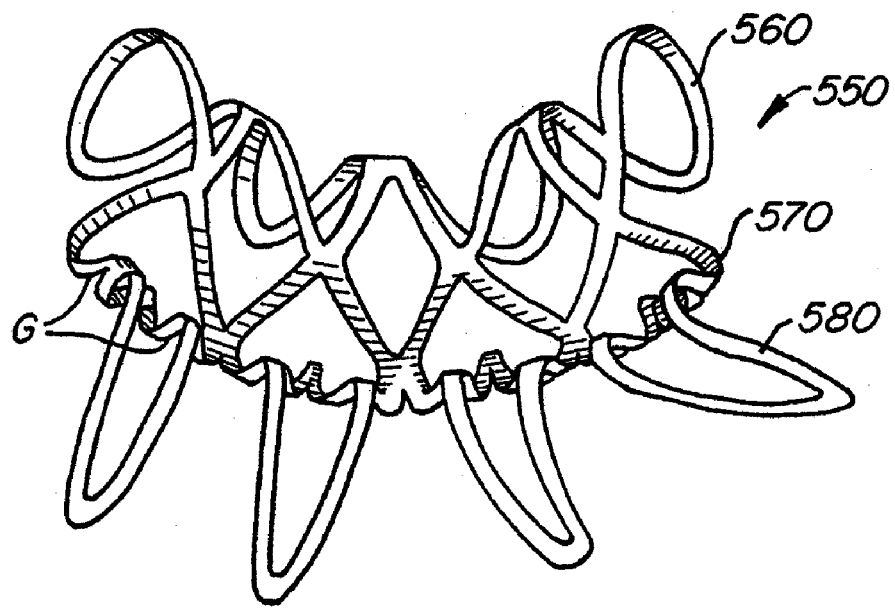

In FIG. 19A, a portion of anchor piece 550 has been flattened out to illustrate the basic anchor cell structure, as well as to illustrate techniques for manufacturing anchor piece 550. In order to form the entire anchor, anchor 550 would be bent at the locations indicated in FIG. 19A, and the basic anchor cell structure would be revolved to form a joined 360° structure. Lip section 560 would be bent back into the page to form a lip that doubles over the groove section, groove section 570 would be bent out of the page into a 'C'- or 'U'-shaped groove, while skirt section 580 would be bent back into the page. FIG. 19B shows the anchor portion after bending and in an expanded deployed configuration.

The basic anchor cell structure seen in FIG. 19A is preferably formed through laser cutting of a flat sheet or of a hollow tube placed on a mandrel. When formed from a flat sheet, the sheet would be cut to the required number of anchor cells, bent to the proper shape, and revolved to form a cylinder. The ends of the cylinder would then be joined together, for example, by heat welding.

If balloon expandable, anchor piece 550 would be formed from an appropriate material, such as stainless steel, and then crimped onto a balloon delivery catheter in a collapsed delivery configuration. If self-expanding and formed from a shape-memory material, such as a nickel-titanium alloy ("Nitinol"), the anchor piece would be heat-set such that it could be constrained within a sheath in the collapsed delivery configuration, and then would dynamically self-expand to the expanded deployed configuration upon removal of the sheath. Likewise, if anchor piece 550 were formed from a wire mesh or braid, such as a spring steel braid, the anchor would be constrained within a sheath in the delivery configuration and dynamically expanded to the deployed configuration upon removal of the sheath.

In FIG. 20, valve piece 600 is described in greater detail. FIG. 20A illustrates valve piece 600 in a collapsed delivery configuration, while FIG. 20B illustrates the valve piece in an expanded deployed configuration. Valve piece 600 comprises replacement valve 610 coupled to expandable frame 620. Replacement valve 610 is preferably biologic, although synthetic valves may also be used. Replacement valve 610 preferably comprises three leaflets 611 coupled to three posts 621 of expandable frame 620. Expandable frame 620 is preferably formed from a continuous piece of material and may comprise tips 622 in the collapsed delivery configuration, which expand to form hoop 624 in the deployed configuration. Hoop 624 is adapted to engage groove section 570 of anchor piece 550 for coupling anchor piece 550 to valve piece 600. As with anchor piece 550, valve piece 600 may be balloon expandable and coupled to a balloon delivery catheter in the delivery configuration. Alternatively, anchor piece 550 may be self-expanding, e.g. Nitinol or wire mesh, and constrained within a sheath in the delivery configuration.

Referring again to FIG. 21, a method for deploying valve piece 600 and coupling it to deployed anchor piece 550 to form two-piece apparatus 510 is described. In FIG. 21A, valve piece 600 is advanced within anchor piece 550 in an at least partially compressed delivery configuration. In FIG. 21B, tips 622 of frame 620 are expanded such that they engage groove section 570 of anchor piece 550. In FIG. 21C, frame 620 continues to expand and form hoop 624. Hoop 624 flares out from the remainder of valve piece 600 and acts to properly locate the hoop within groove section 570. FIG. 21D shows valve piece 600 in a fully deployed configuration, properly seated and friction locked within groove section 570 to form composite anchor/valve apparatus 510.

Figure 22:
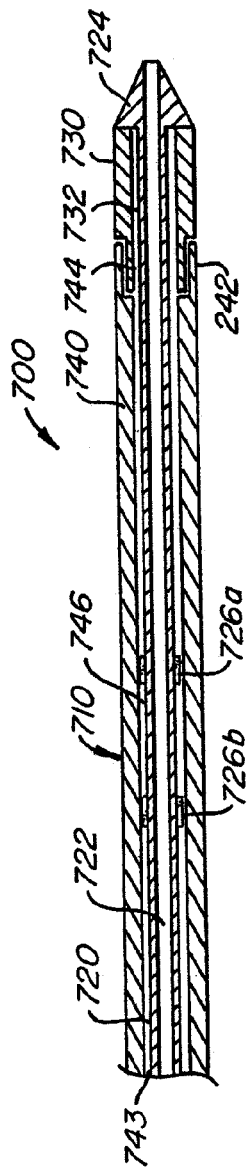
FIG. 22 shows a delivery system for use with the apparatus shown in FIGS. 19-21.

Anchor piece 550 and valve piece 600 of apparatus 510 preferably are spaced apart and releasably coupled to a single delivery catheter while disposed in their reduced delivery configurations. Spacing the anchor and valve apart reduces a delivery profile of the device, thereby enabling delivery through a patient's aorta without requiring a transseptal approach. With reference to FIG. 22, a first embodiment of single catheter delivery system 700 for use with apparatus 510 is described. Delivery system 700 is adapted for use with a preferred self-expanding embodiment of apparatus 510.

Delivery system 700 comprises delivery catheter 710 having inner tube 720, middle distal tube 730, and outer tube 740. Inner tube 720 comprises lumen 722 adapted for advancement over a standard guide wire, per se known. Middle distal tube 730 is coaxially disposed about a distal region of inner tube 720 and is coupled to a distal end 724 of the inner tube, thereby forming proximally-oriented annular bore 732 between inner tube 720 and middle tube 730 at a distal region of delivery catheter 710. Outer tube 740 is coaxially disposed about inner tube 720 and extends from a proximal region of the inner tube to a position at least partially coaxially overlapping middle distal tube 730. Outer tube 740 preferably comprises distal step 742, wherein lumen 743 of outer tube 740 is of increased diameter. Distal step 742 may overlap middle distal tube 730 and may also facilitate deployment of valve piece 600, as described hereinbelow with respect to FIG. 25.

Proximally-oriented annular bore 732 between inner tube 720 and middle distal tube 730 is adapted to receive skirt section 580 and groove section 570 of anchor piece 550 in the reduced delivery configuration. Annular space 744 formed at the overlap between middle distal tube 730 and outer tube 740 is adapted to receive lip section 560 of anchor piece 550 in the reduced delivery configuration. More proximal annular space 746 between inner tube 720 and outer tube 740 may be adapted to receive replacement valve 610 and expandable frame 620 of valve piece 600 in the reduced delivery configuration.

Inner tube 720 optionally may comprise retainer elements 726a and 726b to reduce migration of valve piece 600. Retainer elements 726 preferably are fabricated from a radiopaque material, such as platinum-iridium or gold, to facilitate deployment of valve piece 600, as well as coupling of the valve piece to anchor piece 550. Additional or alternative radiopaque elements may be disposed at other locations about delivery system 700 or apparatus 510, for example, in the vicinity of anchor piece 550.

Figure 23:
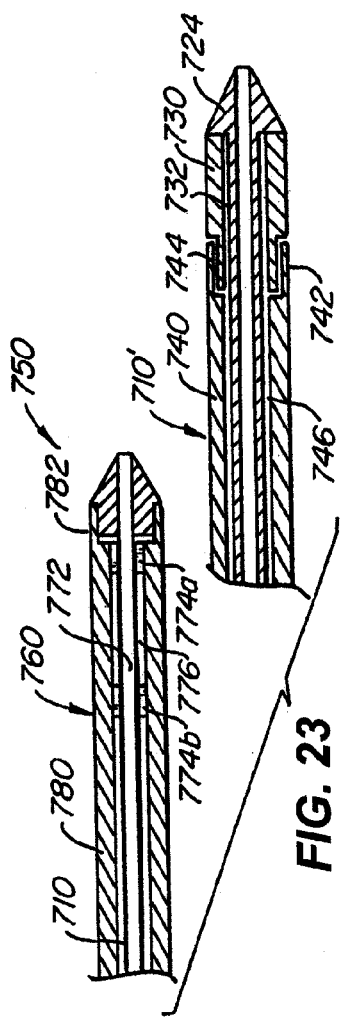
FIG. 23 shows an alternative embodiment of a delivery system for use with the apparatus shown in FIGS. 19-21.

With reference now to FIG. 23, an alternative delivery system for use with apparatus of the present invention is described. Delivery system 750 comprises two distinct catheters adapted to deliver the anchor and valve pieces, respectively: anchor delivery catheter 710' and valve delivery catheter 760. In use, catheters 710' and 760 may be advanced sequentially to a patient's diseased heart valve for sequential deployment and coupling of anchor piece 550 to valve piece 600 to form composite two-piece apparatus 510.

Delivery catheter 710' is substantially equivalent to catheter 710 described hereinabove, except that catheter 710' does not comprise retainer elements 726, and annular space 746 does not receive valve piece 600. Rather, valve piece 600 is received within catheter 760 in the collapsed delivery configuration. Catheter 760 comprises inner tube 770 and outer tube 780. Inner tube 770 comprises lumen 772 for advancement of catheter 760 over a guide wire. The inner tube optionally may also comprise retainer elements 774a and 774b, e.g. radiopaque retainer elements 774, to reduce migration of valve piece 600. Outer tube 780 is coaxially disposed about inner tuber 770 and preferably comprises distal step 782 to facilitate deployment and coupling of valve piece 600 to anchor piece 550, as described hereinbelow. Valve piece 600 may be received in annular space 776 between inner tube 770 and outer tube 780, and more preferably may be received within annular space 776 between retainer elements 774.

Figure 24:
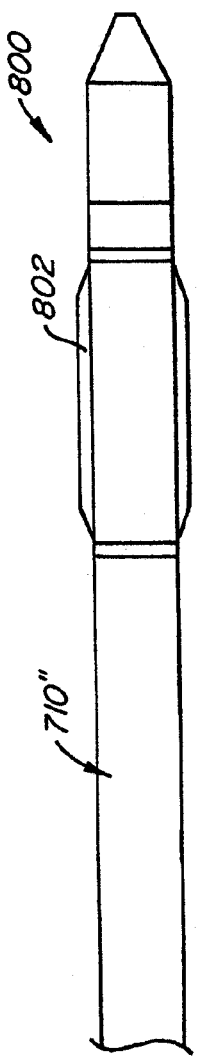
FIG. 24 shows yet another alternative embodiment of a delivery system for use with the apparatus shown in FIGS. 19-21.

Referring now to FIG. 24, another alternative delivery system is described. As discussed previously, either anchor piece 550 or valve piece 600 (or portions thereof or both) may be balloon expandable from the delivery configuration to the deployed configuration. Delivery system 800 is adapted for delivery of an embodiment of apparatus 510 wherein the valve piece is balloon expandable. Additional delivery systems—both single and multi-catheter—for deployment of alternative combinations of balloon and self-expandable elements of apparatus of the present invention will be apparent to those of skill in the art in view of the illustrative delivery systems provided in FIGS. 22-24.

In FIG. 24, delivery system 800 comprises delivery catheter 710". Delivery catheter 710" is substantially equivalent to delivery catheter 710 of delivery system 700, except that catheter 710" does not comprise retainer elements 726, and annular space 746 does not receive the valve piece. Additionally, catheter 710" comprises inflatable balloon 802 coupled to the exterior of outer tube 740", as well as an inflation lumen (not shown) for reversibly delivering an inflation medium from a proximal region of catheter 710" into the interior of inflatable balloon 802 for expanding the balloon from a delivery configuration to a deployed configuration. Valve piece 600 may be crimped to the exterior of balloon 802 in the delivery configuration, then deployed and coupled to anchor piece 550 in vivo. Delivery catheter 710" preferably comprises radiopaque marker bands 804a and 804b disposed on either side of balloon 802 to facilitate proper positioning of valve piece 600 during deployment of the valve piece, for example, under fluoroscopic guidance.

With reference now to FIG. 25, in conjunction with FIGS. 19-22, an illustrative method of endovascularly replacing a patient's diseased heart valve using apparatus of the present invention is described. In FIG. 25A, a distal region of delivery system 700 of FIG. 22 has been delivered through a patient's aorta A, e.g., over a guide wire and under fluoroscopic guidance using well-known percutaneous techniques, to a vicinity of diseased aortic valve AV of heart H. Apparatus 510 of FIGS. 19-21 is disposed in the collapsed delivery configuration within delivery catheter 710 with groove section 570 and skirt section 580 of anchor piece 550 collapsed within annular bore 732, and lip section 560 of anchor piece 550 collapsed within annular space 744. Valve piece 600 is disposed in the collapsed delivery configuration between retainer elements 726 within more proximal annular space 746. Separation of anchor piece 550 and valve piece 600 of apparatus 510 along the longitudinal axis of delivery catheter 710 enables percutaneous aortic delivery of apparatus 510 without requiring a transseptal approach.

Aortic valve AV comprises native valve leaflets L attached to valve annulus An. Coronary ostia O are disposed just proximal of diseased aortic valve AV. Coronary ostia O connect the patient's coronary arteries to aorta A and are the conduits through which the patient's heart muscle receives oxygenated blood. As such, it is critical that the ostia remain unobstructed post-deployment of apparatus 510.

Figure 25A:
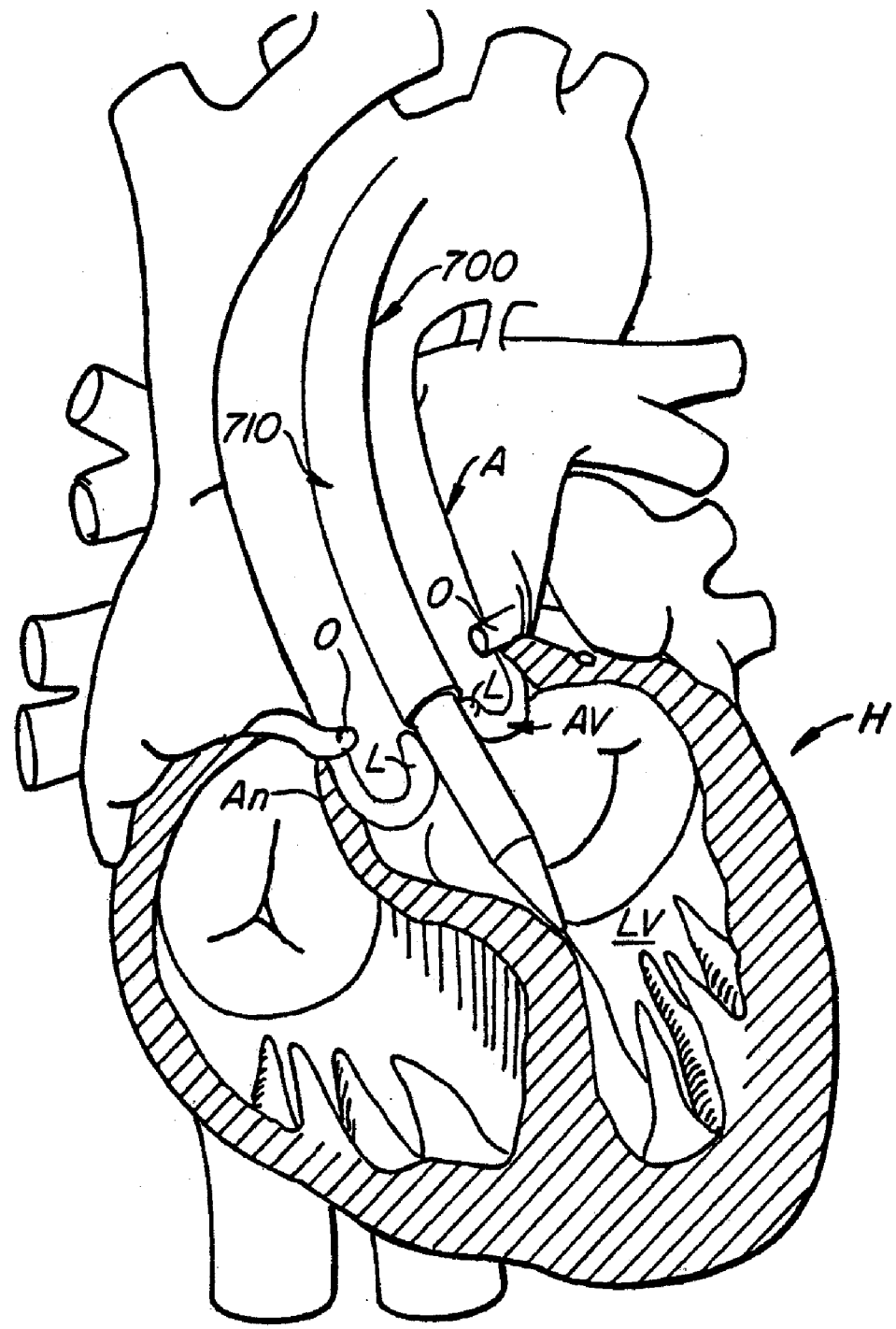
FIGS. 25A-I illustrate a method of delivering and deploying a two-piece replacement heart valve and anchor.
Figure 25B:
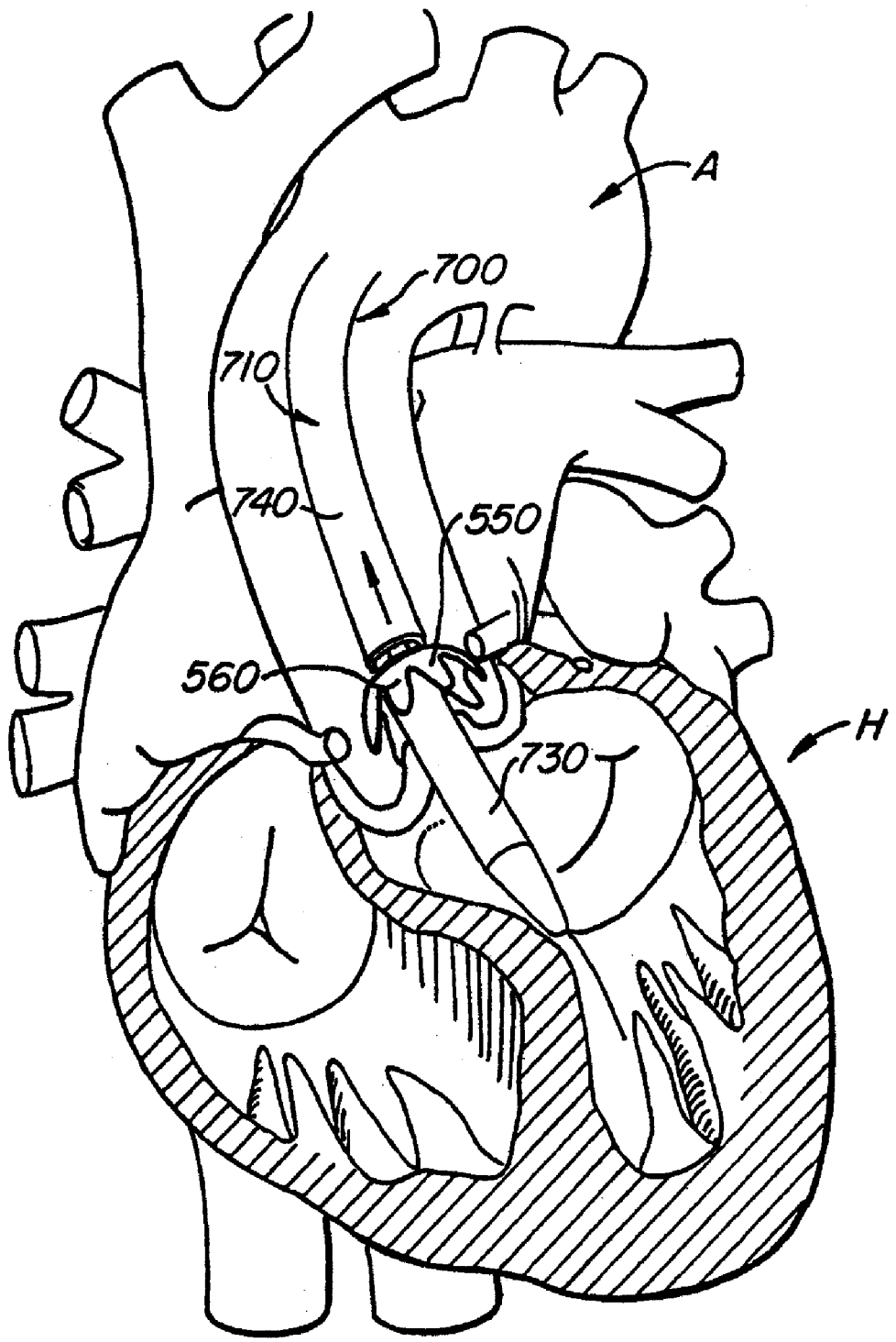
Figure 25C:
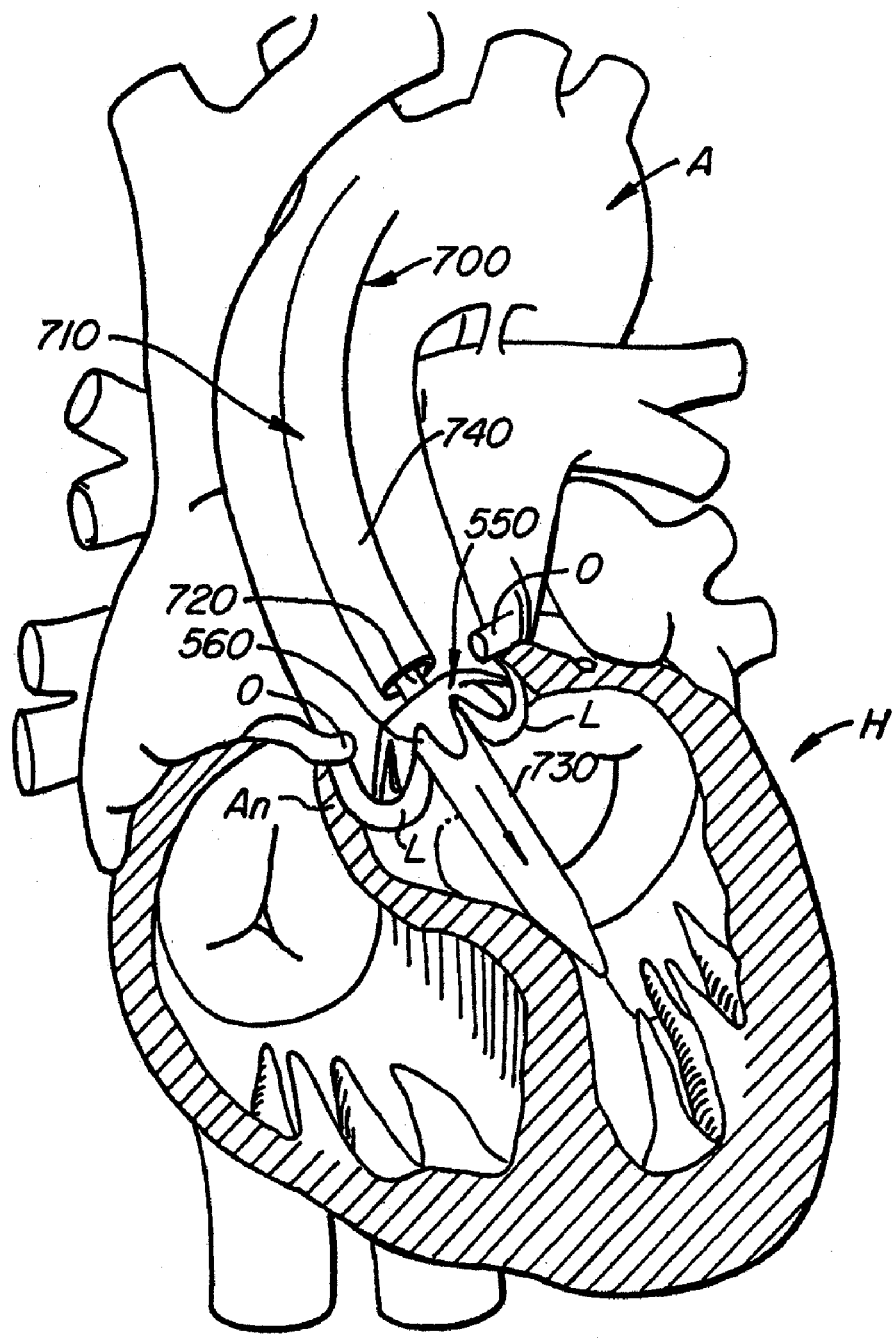

In FIG. 25A, a distal end of delivery catheter 710 has been delivered across diseased aortic valve AV into the patient's left ventricle LV. As seen in FIG. 25B, outer tube 740 is then retracted proximally relative to inner tube 720 and middle distal tube 730. Outer tube 740 no longer coaxially overlaps middle distal tube 730, and lip section 560 of anchor piece 550 is removed from annular space 744. Lip section 560 self-expands to the deployed configuration. As seen in FIG. 25C, inner tube 720 and middle tube 730 (or all of delivery catheter 710) are then distally advanced until lip section 560 engages the patient's native valve leaflets L, thereby providing positive registration of anchor piece 550 to leaflets L. Registration may be confirmed, for example, via fluoroscopic imaging of radiopaque features coupled to apparatus 510 or delivery system 700 and/or via resistance encountered by the medical practitioner distally advancing anchor piece 550.

Lip section 560 may be dynamically repositioned until it properly engages the valve leaflets, thereby ensuring proper positioning of anchor piece 550 relative to the native coronary ostia O, as well as the valve annulus An, prior to deployment of groove section 570 and skirt section 580. Such multi-step deployment of anchor piece 550 enables positive registration and dynamic repositioning of the anchor piece. This is in contrast to previously known percutaneous valve replacement apparatus.

Figure 25D:
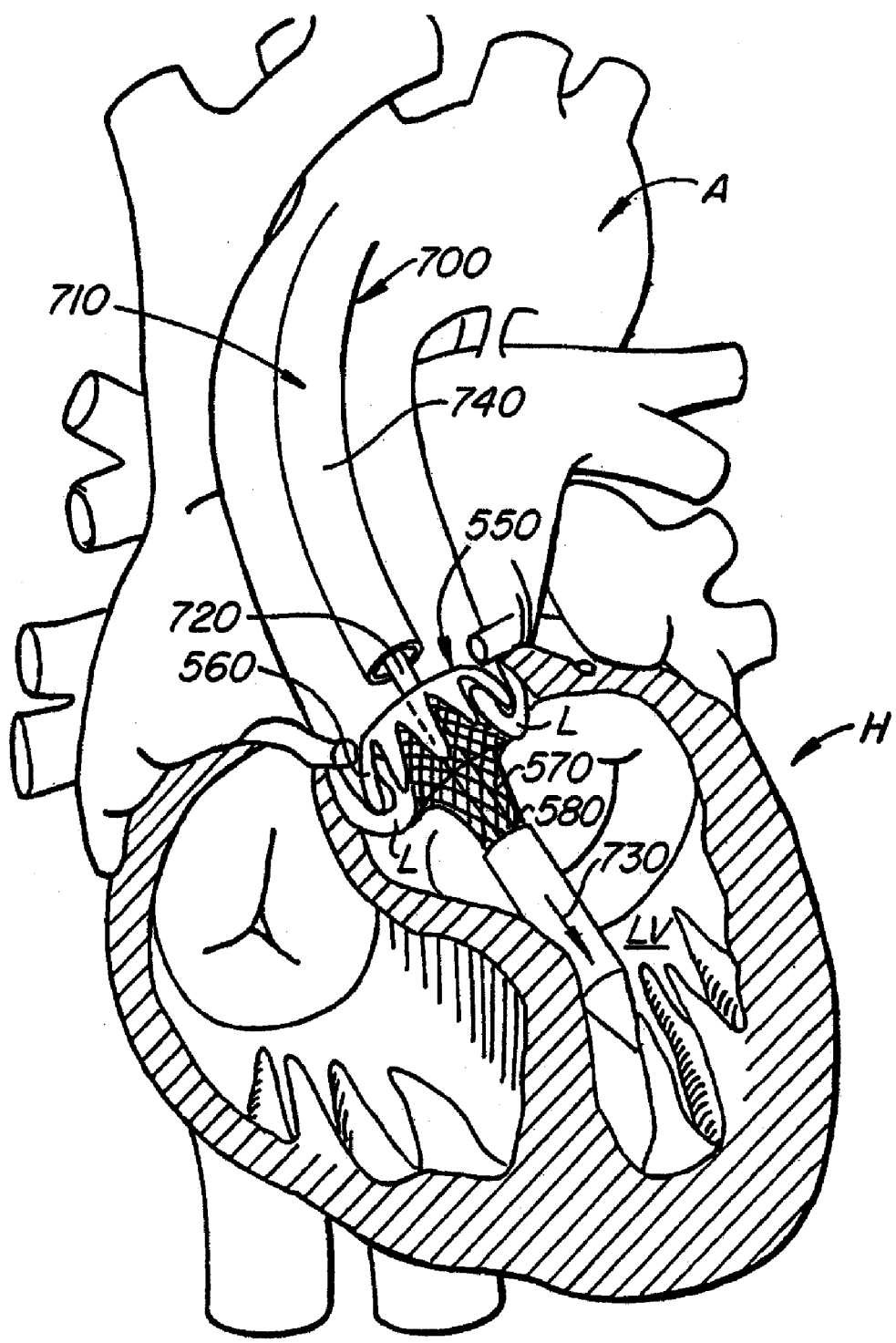
Figure 25E:
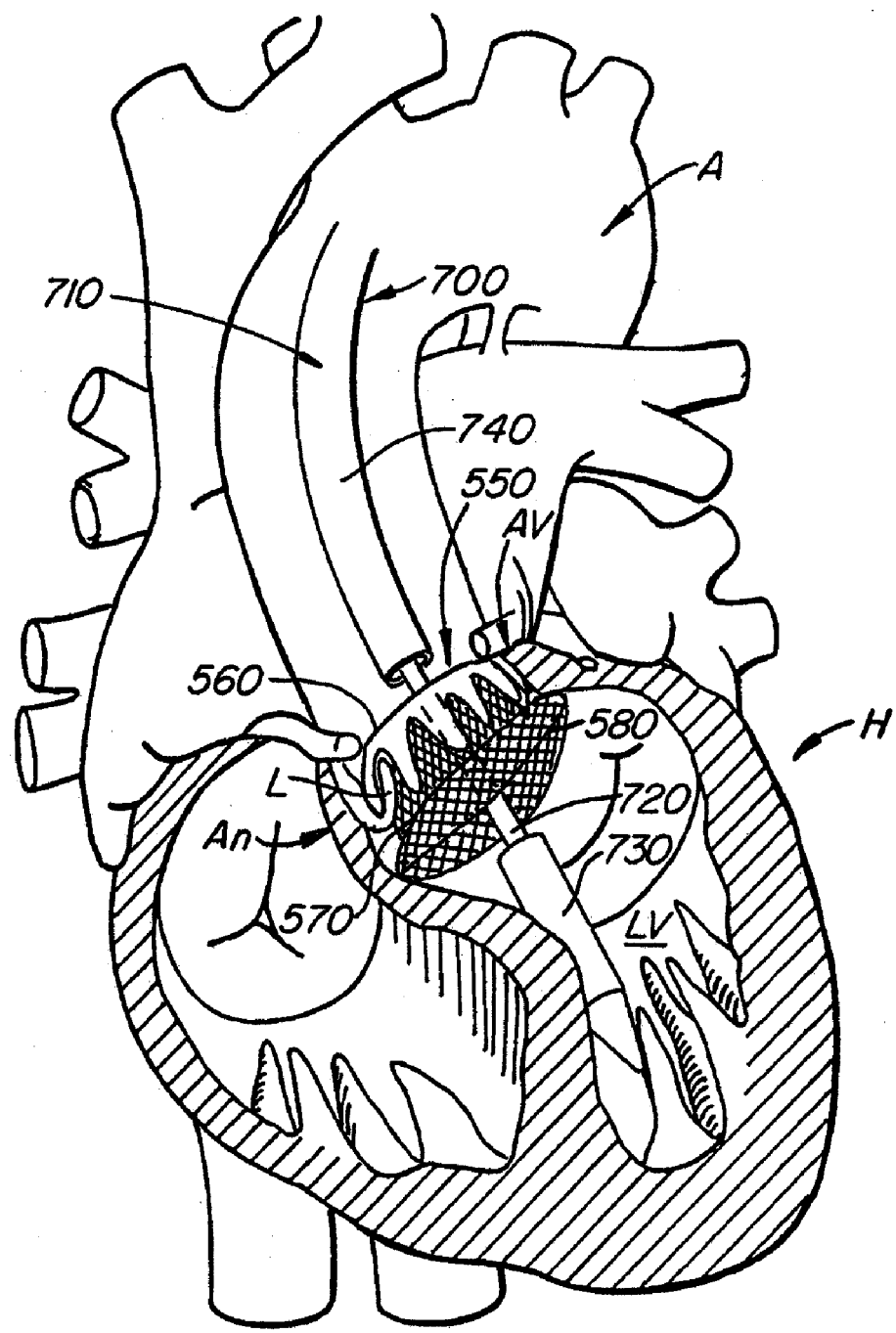

As seen in FIG. 25D, once leaflets L have been engaged by lip section 560 of anchor piece 550, inner tube 720 and middle distal tube 730 are further distally advanced within left ventricle LV, while outer tube 740 remains substantially stationary. Lip section 560, engaged by leaflets L, precludes further distal advancement/migration of anchor piece 550. As such, groove section 570 and skirt section 580 are pulled out of proximally-oriented annular bore 732 between inner tube 720 and middle distal tube 730 when the tubes are distally advanced. The groove and skirt sections self-expand to the deployed configuration, as seen in FIG. 25E. Groove section 570 pushes native valve leaflets L and lip section 560 against valve annulus An, while skirt section 580 seals against an interior wall of left ventricle LV, thereby reducing paravalvular regurgitation across aortic valve AV and precluding proximal migration of anchor piece 550.

Figure 25F:
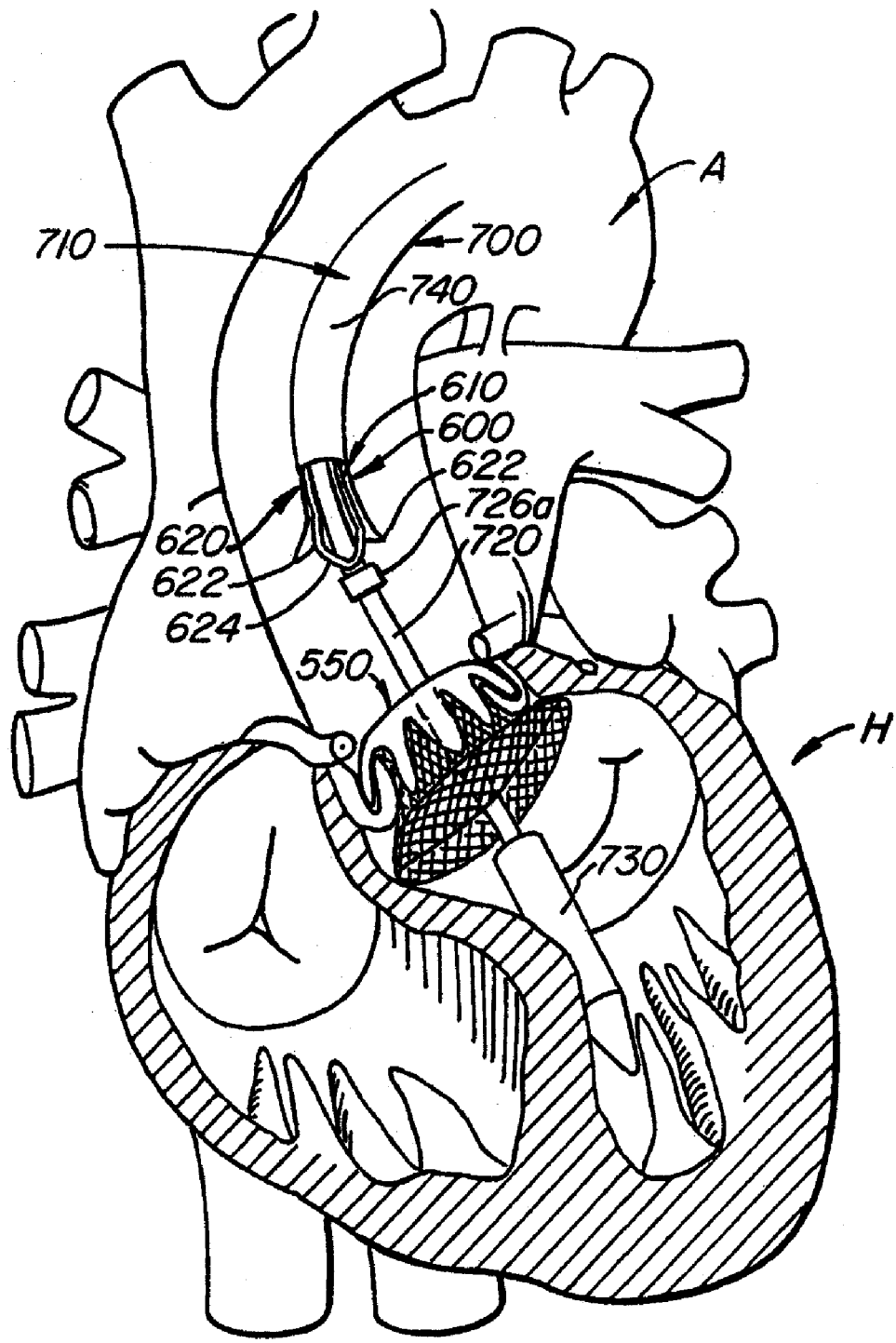

With anchor piece 550 deployed and native aortic valve AV displaced, valve piece 600 may be deployed and coupled to the anchor piece to achieve percutaneous aortic valve replacement. Outer tube 740 is further proximally retracted relative to inner tube 720 such that valve piece 600 is partially deployed from annular space 746 between inner tube 720 and outer tube 740, as seen in FIG. 25F. Expandable frame 620 coupled to replacement valve 610 partially self-expands such that tips 622 partially form hoop 624 for engagement of groove section 570 of anchor piece 550 (see FIG. 21B). A proximal end of expandable frame 620 is engaged by distal step 742 of outer tube 740.

Figure 25G:
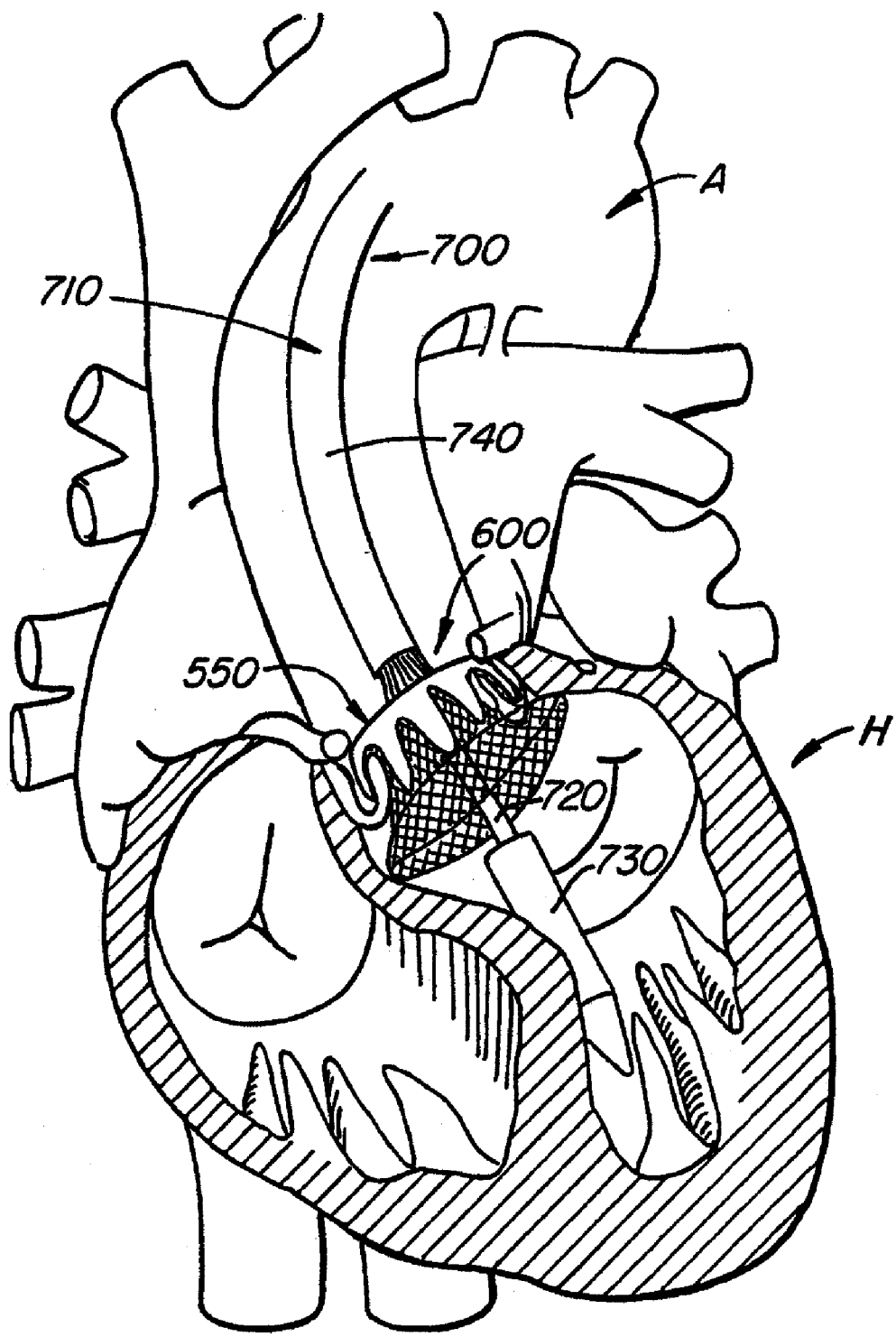
Figure 25H:
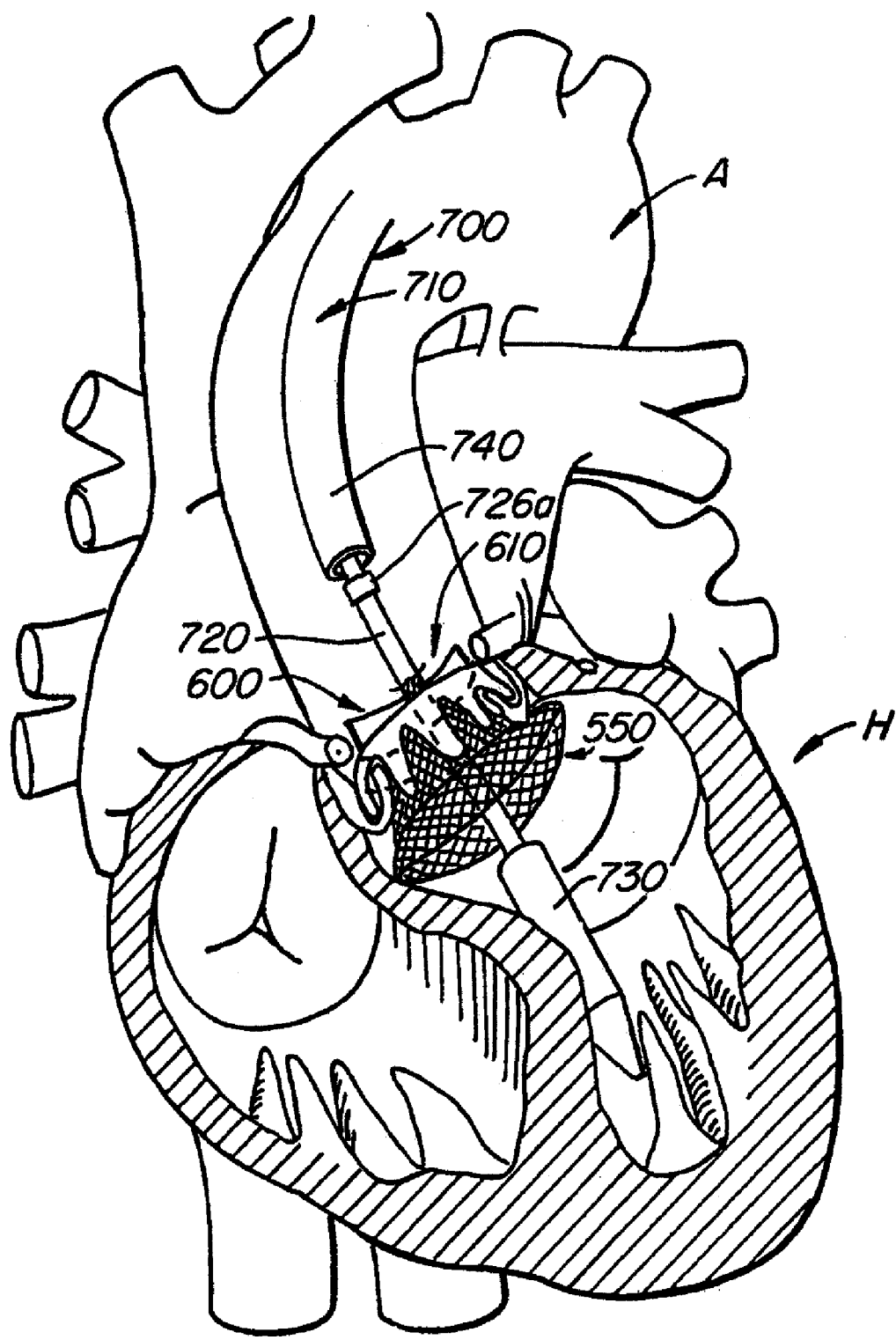

Subsequent re-advancement of outer tube 740 relative to inner tube 720 causes distal step 742 to distally advance valve piece 600 within anchor piece 550 until tips 622 of expandable frame 620 engage groove section 570 of anchor piece 550, as seen in FIG. 25G. As discussed previously, groove section 570 comprises additional material and reduced openings or gaps G, as compared to previously known apparatus, which is expected to reduce native valve tissue protrusion through the gaps and facilitate engagement of tips 622 with the groove section. Outer tube 740 then is proximally retracted again relative to inner tube 720, and valve piece 600 is completely freed from annular space 746. Frame 620 of valve piece 600 fully expands to form hoop 624, as seen in FIG. 25H.

Figure 25I:
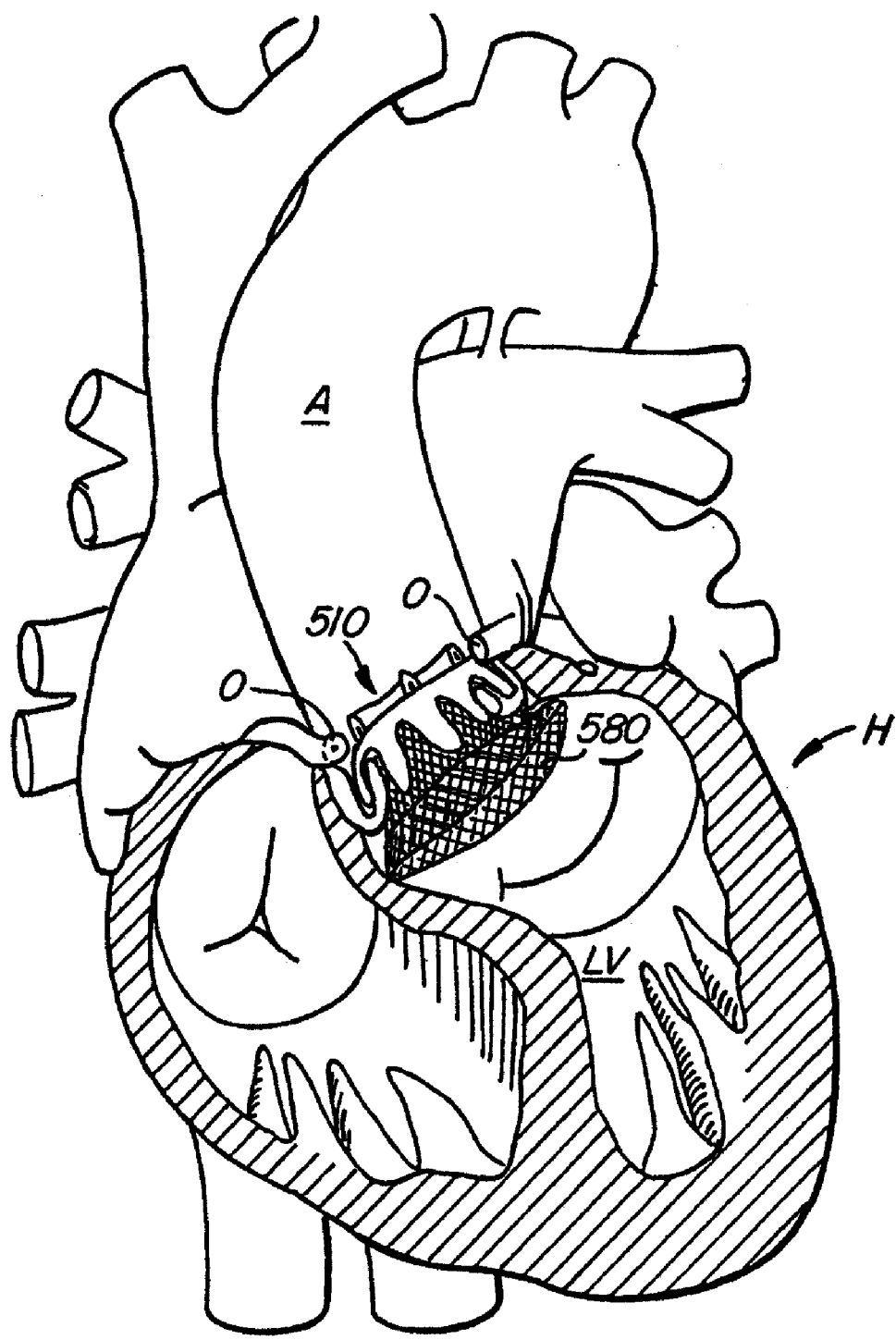

Hoop 624 friction locks within groove section 570 of anchor piece 550, thereby coupling the anchor piece to the valve piece and forming composite two-piece apparatus 510, which provides a percutaneous valve replacement. As seen in FIG. 25I, delivery catheter 710 may then be removed from the patient, completing the procedure. Blood may freely flow from left ventricle LV through replacement valve 610 into aorta A. Coronary ostia O are unobstructed, and paravalvular regurgitation is reduced by skirt section 580 of anchor piece 550.

Referring now to FIG. 26, an alternative embodiment of two-piece apparatus 510 is described comprising an alignment/locking mechanism. Such a mechanism may be provided in order to ensure proper radial alignment of the expandable frame of the valve piece with the groove section of the anchor piece, as well as to ensure proper longitudinal positioning of the frame within the hoop. Additionally, the alignment/locking mechanism may provide a secondary lock to further reduce a risk of the anchor piece and the valve piece becoming separated post-deployment and coupling of the two pieces to achieve percutaneous valve replacement.

In FIG. 26, apparatus 510' comprises valve piece 600' of FIG. 26A and anchor piece 550' of FIG. 26B. Anchor piece 550' and valve piece 600' are substantially the same as anchor piece 550 and valve piece 600 described hereinabove, except that anchor piece 550' comprises first portion 652 of illustrative alignment/locking mechanism 650, while valve piece 600' comprises second portion 654 of the alignment/locking mechanism for coupling to the first portion. First portion 652 illustratively comprises three guideposts 653 coupled to skirt section 580' of anchor piece 550' (only one guidepost shown in the partial view of FIG. 26B), while second portion 654 comprises three sleeves 655 coupled to posts 621' of expandable frame 620' of valve piece 600'.

When anchor piece 550' is self-expanding and collapsed in the delivery configuration, guideposts 653 may be deployed with skirt section 580', in which case guideposts 653 would rotate upward with respect to anchor piece 550' into the deployed configuration of FIG. 26B. Alternatively, when anchor piece 550' is either balloon or self-expanding and is collapsed in the delivery configuration, guideposts 653 may be collapsed against groove section 570' of the anchor piece and may be deployed with the groove section. Deploying guideposts 653 with skirt section 580' has the advantages of reduced delivery profile and ease of manufacturing, but has the disadvantage of significant dynamic motion during deployment. Conversely, deploying guideposts 653 with groove section 570' has the advantage of minimal dynamic motion during deployment, but has the disadvantage of increased delivery profile. Additional deployment configurations will be apparent to those of skill in the art. As will also be apparent, first portion 652 of alignment/locking mechanism 650 may be coupled to alternative sections of anchor piece 550' other than skirt section 580'.

Sleeves 655 of second portion 654 of alignment/locking mechanism 650 comprise lumens 656 sized for coaxial disposal of sleeves 655 about guideposts 653 of first portion 652. Upon deployment, sleeves 655 may friction lock to guideposts 653 to ensure proper radial and longitudinal alignment of anchor piece 550' with valve piece 600', as well as to provide a secondary lock of the anchor piece to the valve piece. The secondary lock enhances the primary friction lock formed by groove section 570' of the anchor piece with hoop 624' of expandable frame 620' of the valve piece.

To facilitate coupling of the anchor piece to the valve piece, suture or thread may pass from optional eyelets 651a of guideposts 653 through lumens 656 of sleeves 655 to a proximal end of the delivery catheter (see FIG. 27). In this manner, second portion 654 of mechanism 650 may be urged into alignment with first portion 652, and optional suture knots (not shown), e.g. pre-tied suture knots, may be advanced on top of the mechanism post-coupling of the two portions to lock the two portions together. Alternatively, guideposts 653 may comprise optional one-way valves 651b to facilitate coupling of the first portion to the second portion. Specifically, sleeves 655 may be adapted for coaxial advancement over one-way valves 651b in a first direction that couples the sleeves to guideposts 653, but not in a reverse direction that would uncouple the sleeves from the guideposts.

Referring now to FIG. 27, an alternative embodiment of apparatus 510' comprising an alternative alignment/locking mechanism is described. Apparatus 510" is illustratively shown in conjunction with delivery system 700 described hereinabove with respect to FIG. 22. Valve piece 600" is shown partially deployed from outer tube 740 of catheter 710. For the sake of illustration, replacement valve 610" of valve piece 600", as well as inner tube 720 and middle distal tube 730 of delivery catheter 710, are not shown in FIG. 27.

In FIG. 27, anchor piece 550" of apparatus 510" comprises first portion 652' of alignment/locking mechanism 650', while valve piece 600" comprises second portion 654' of the alternative alignment/locking mechanism. First portion 652' comprises eyelets 660 coupled to groove section 570" of anchor piece 550". Second portion 654' comprises knotted loops of suture 662 coupled to tips 622" of expandable frame 620" of valve piece 600". Suture 661 extends from knotted loops of suture 662 through eyelets 660 and out through annular space 746 between outer tube 740 and inner tube 720 (see FIG. 22) of catheter 710 to a proximal end of delivery system 700. In this manner, a medical practitioner may radially and longitudinally align valve piece 600" with anchor piece 550" by proximally retracting sutures 661 (as shown by arrows in FIG. 27) while distally advancing distal step 742 of outer tube 740 against valve piece 600" until tips 622" of the valve piece engage groove section 570" of anchor piece 550". Proximal retraction of outer tube 740 then causes expandable frame 620" to further expand and form hoop 624" that friction locks with groove section 570" of anchor piece 550", thereby forming apparatus 510" as described hereinabove with respect to apparatus 510. A secondary lock may be achieved by advancing optional suture knots (not shown) to the overlap of eyelets 660 and knotted loops of suture 662. Such optional suture knots preferably are pre-tied.

With reference now to FIG. 28, yet another alternative embodiment of apparatus 510', comprising yet another alternative alignment/locking mechanism 650, is described. First portion 652" of alignment/locking mechanism 650" is coupled to anchor piece 550''' of apparatus 510''', while second portion 654" is coupled to valve piece 600'''. The first portion comprises male posts 670 having flared ends 671, while the second portion comprises female guides 672 coupled to tips 622''' of expandable frame 620''' of valve piece 600'''.

Female guides 672 are translatable about male posts 670, but are constrained by flared ends 671 of the male posts. In this manner, anchor piece 550''' and valve piece 600''' remain coupled and in radial alignment with one another at all times—including delivery—but may be longitudinally separated from one another during delivery. This facilitates percutaneous delivery without requiring a transseptal approach, while mitigating a risk of inadvertent deployment of the anchor and valve pieces in an uncoupled configuration. Additional alignment/locking mechanisms will be apparent in view of the mechanisms described with respect to FIGS. 26-28.

What is claimed is:

1. A method for endovascularly replacing a patient's native heart valve, the method comprising:
   delivering an expandable anchor and a replacement valve to a vicinity of the native heart valve, wherein leaflet engagement elements extend distally from a proximal region of the anchor;
   sandwiching native valve leaflets between the distally extending leaflet engagement elements and the anchor; and
   expanding the anchor from a collapsed delivery configuration to an expanded configuration;
   positioning a proximal end of the anchor further from a left ventricle than a distal end of the anchor,
   wherein the replacement valve allows the flow of blood through the replacement valve in a first configuration and prevents the flow of blood through the valve in a second configuration.

2. A method for endovascularly replacing a patient's native heart valve, the method comprising:
   delivering an expandable anchor and a replacement valve to a vicinity of the native heart valve, wherein leaflet engagement elements extend distally from a first end of the anchor;
   sandwiching native valve leaflets between the distally extending leaflet engagement elements and the anchor; and
   expanding the anchor from a collapsed delivery configuration to an expanded configuration;
   positioning the first end of the anchor further from a left ventricle than a second end of the anchor,
   wherein the replacement valve allows the flow of blood through the replacement valve in a first configuration and prevents the flow of blood through the valve in a second configuration.

3. A method for endovascularly replacing a patient's native heart valve, the method comprising:
   delivering an expandable anchor and a replacement valve to a vicinity of the native heart valve, wherein leaflet engagement elements extend distally from a proximal end of the anchor;
   sandwiching native valve leaflets between the distally extending leaflet engagement elements and the anchor; and
   expanding the anchor from a collapsed delivery configuration to an expanded configuration to secure the anchor within the native heart valve;

positioning the proximal end of the anchor further from a left ventricle than a distal end of the anchor, wherein the replacement valve allows the flow of blood through the replacement valve in a first configuration and prevents the flow of blood through the valve in a second configuration.

4. The method of claim 3 wherein expanding the anchor from a collapsed delivery configuration to an expanded configuration comprises allowing the anchor to self-expand to thereby sandwich the native valve leaflets between the distally extending leaflet engagement elements and the anchor.

5. The method of claim 3 wherein the leaflet engagement elements extend generally parallel to the longitudinal axis of the expandable anchor when the anchor is in the expanded configuration.

6. The method of claim 3 wherein the expandable anchor and the replacement valve are delivered as two separate elements, the method further comprising deploying the expandable anchor and the replacement valve in the vicinity of the native heart valve in two different steps.

7. The method of claim 6 further comprising engaging the expandable anchor and the replacement valve after they are deployed in the vicinity of the native heart valve to secure the replacement heart valve to the expandable anchor.

8. The method of claim 7 wherein the replacement heart valve comprises an expandable support structure and replacement valve leaflets, and wherein engaging the expandable anchor and the replacement valve in the vicinity of the native heart valve comprises coupling the expandable anchor and the expandable support structure to secure the replacement heart valve to the expandable anchor.

* * * * *